(12) United States Patent
Gant et al.

(10) Patent No.: US 7,772,248 B2
(45) Date of Patent: Aug. 10, 2010

(54) PREPARATION AND UTILITY OF SUBSTITUTED IMIDAZOPYRIDINE COMPOUNDS WITH HYPNOTIC EFFECTS

(75) Inventors: Thomas G. Gant, Carlsbad, CA (US); Sepehr Sarshar, Cardiff by the Sea, CA (US)

(73) Assignee: Auspex Pharmaceuticals, Inc., Vista, CA (US)

( * ) Notice: Subject to any disclaimer, the term of this patent is extended or adjusted under 35 U.S.C. 154(b) by 0 days.

(21) Appl. No.: 11/755,634

(22) Filed: May 30, 2007

(65) Prior Publication Data

US 2007/0281965 A1 Dec. 6, 2007

Related U.S. Application Data

(60) Provisional application No. 60/810,935, filed on Jun. 5, 2006.

(51) Int. Cl.
*A61K 31/4745* (2006.01)
*A61K 31/4184* (2006.01)
*C07D 235/02* (2006.01)
*C07D 471/02* (2006.01)

(52) U.S. Cl. .................. 514/303; 514/393; 546/120; 548/302.7

(58) Field of Classification Search .................. 514/303, 514/393; 546/120; 548/302.7
See application file for complete search history.

(56) References Cited

U.S. PATENT DOCUMENTS

| 4,382,938 | A | 5/1983 | Kaplan |
| 4,460,592 | A | 7/1984 | Kaplan |
| 6,514,531 | B1 | 2/2003 | Alaux |
| 2002/0013372 | A1 | 1/2002 | Ekins |
| 2007/0281965 | A1 | 12/2007 | Gant |
| 2008/0033011 | A1 | 2/2008 | Tung |
| 2008/0058351 | A1 | 3/2008 | Tung |
| 2008/0318964 | A1 | 12/2008 | Czarnik |
| 2009/0062312 | A1 | 3/2009 | Czarnik |
| 2009/0076066 | A1 | 3/2009 | Czarnik |
| 2009/0208413 | A1 | 8/2009 | Reis et al. |

FOREIGN PATENT DOCUMENTS

| WO | 9526325 | 10/1995 |
| WO | 2006091885 | 8/2006 |
| WO | WO 2006091885 A2 * | 8/2006 |
| WO | 2007143468 | 12/2007 |
| WO | 2008005471 | 1/2008 |
| WO | 2008024481 | 2/2008 |
| WO | 2008157564 | 12/2008 |

OTHER PUBLICATIONS

Abstract of Hays, Journal of Forensic Sciences (2005), 50(6), 1342-1360, and structures.*

Vippagunta et al., Advanced Drug Delivery Reviews, p. 1.*
Pharmacological uses and perspectives of heavy water and deuterated compounds, Kushner, D. J et al., Canadian Journal of Physiology and Pharmacology (1999), 77(2), 79-88.
"Drug Report for Zolpidem","Drug Report for Zolpidem, Thomson Investigational Drug Database (Jan. 25, 2009)".
Hays, Patrick A. et al.; Proton Nuclear Magnetic Resonance Spectroscopy (NMR) Methods for Determining the Purity of Reference Drug Standards and Illicit Forensic Drug Seizures; "(Journal of Forensic Sciences, (2005), 50(6), 1342-60)".
"Validation of a Liquid Chromatography Tandem Mass Spectrometry Method for the Simultaneous Determination of 26 Benzodiazepines and Metabolites, Zolpidem and Zopiclone, in Blood, Urine, and Hair","Laloup, Marleen et al. (Journal of Analytical Toxicology, (2005), 29(7), 616-26)".
Zolpidem-d6 (C19H15D6N3O); catalog No. Z650002; company, Toronto Research Chemicals, Inc. (TRC) website: http://www.trc-canada.com/show_cat.php?CatNum=Z&button=+Z+.
Bauer, L et al; "Influence of long-term infusions on lidocaine kinetics","Clin. Pharmacol. Ther. 31(4), 433-437 (1982)".
Borgstrom, L et al; "Comparative Pharmacokinetics of Unlabeled and Deuterium- Labeled Terbutaline: Demonstration of a Small Isotope Effect","J Pharm Sci, 77(11) 952-4 (1988)".
Browne, T; "Chapter 2. Isotope Effect: Implications for pharmaceutical investigations","Stable isotopes in pharmaceutical research; Elsevier; Amsterdam, 1997".
Browne, T et al; "Pharmacokinetic equivalence of stable-isotope-labeled and unlabeled drugs. Phenobarbital in man","J Clin Pharmacol, 22, 309-15 (1982)".

(Continued)

*Primary Examiner*—Yong Chu
(74) *Attorney, Agent, or Firm*—Dennis A. Bennett; Mike Sertic

(57) ABSTRACT

The present disclosure is directed to modulators of $GABA_A$ receptors and pharmaceutically acceptable salts and prodrugs thereof, the chemical synthesis thereof, and the medical use of such compounds for the treatment and/or management of sleep disorders and/or for providing a patient in need with a hypnotic, anxiolytic or anti-convulsive effect are described.

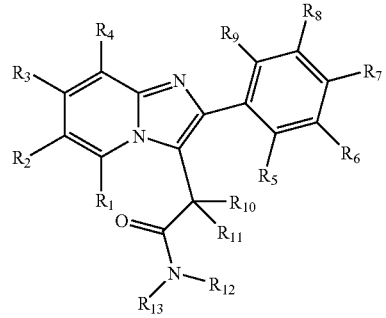

Formula 1

17 Claims, No Drawings

OTHER PUBLICATIONS

Burm, AGL et al; "Pharmacokinetics of Lidocaine and Bupivacaine and stbel isotope labelled analogues: a study in healthy volunteers","Biopharma & Drug Disp, 9 85-95 (1988)".

Elison, C et al; "Effect of deuteration of N-CH3 Group on Potency and enzymatic N-demethylation of morphine","Science, 134(3485) 1078-9 (1961)".

Farmer, PB et al; "Synthesis, metabolism, and antitumor activity of deuterated analogues of 1-(2-chloroethyl)-3-cyclohexyl-1-nitrosourea","J Med Chem, 21(6) 514-520 (1978)".

Fisher, MB et al; "The complexities inherent in attempts to decrease drug clearance by blocking sites of CYP-mediated metabolism","Curr Opin in Drug Disc & Develop 9(1) 101-109 (2006)".

Foster, AB; "Deuterium isotope effects in studies of drug metabolism","Trends in Pharma Sci, 524-527 (1984)".

Helfenbein, J et al; "Isotopic Effect Study of Propofol Deuteration on the Metabolism, Activity, and Toxicity of the Anesthetic","J Med Chem, 45, 5806-5808 (2002)".

Lee, H et al; "Deuterium magic angle spinning studies of substrates bound to cytochrome P450","Biochem. 38 10808-13 (1999)".

Mamada, K et al; "Pharmacokinetic equivalence of deuterium-labeled and unlabeled phenytoin","Drug Metab Disp. 14 (4) 509-11 (1986)".

Nelson, SD et al; "The use of deuterium isotope effects to probe the active site properties, mechanism, of cytochrome P450-catalyzed reactions, and mechanisms of metabolically dependent toxicity","Drug Metab Disp. 31(12) 1481-98 (2003)".

Nelson, SD et al; "Primary and B-Secondary Deuterium Isotope Effects in N-Deethylation reactions","J Med Chem. 18(11) 1062-1065 (1975)".

Pohl, LR et al; "Determination of Toxic Pathways of Metabolism by Deuterium Substitution","Drug Metab Rev. 15(7) 1335-51 (1984-5)".

Rampe, D et al; "Deuterated analogs of verapamil and nifedipine. Synthesis and biological activity","Eur J Med Chem. 28 259-263 (1993)".

Zolpidem-d6, http://www.synfine.com/products hd —1 details. cfm?autoid=892, catalog: Synfine, catalog no: SI-01305-002, First viewed by applicants' representatives on Oct. 25, 2009.

Zolpidem-d6, http://www.cerilliant.com/shoponline/Item_Details. aspx?itemno=985efc64f39c-43d2- a876-1ab6249fd371, catalog: Cerilliant, catalog No: Z-001, First viewed by applicants' representatives on Oct. 23, 2009.

Material Safety Data Sheet: Zolpidem-d6, Material Safety Data Sheet: Zolpidem-d6, manufacturer: Cerilliant catalog No: Z-001, Jun. 4, 2009.

Zolpidem-d6, http://www.alsachim.conn/product-C366-global-Zolpidem-d6ttml, catalog: AlsaChim, catalog no: C366, First viewed by applicants' representatives on Oct. 23, 2009.

Zolpidem-d6, http://www.tlcpharmachem.com/tlc_item. php?upc=Z-041&li=le_21&sub=Z, catalog: TLC PharmaChem TLC ID#: Z-041, First viewed by applicants' representatives on Oct. 23, 2009.

Zolpidem-d6, http://www.clearsynth.com/view—product _details. asp?productid=1222, catalog: Clear Synth Labs catalog no. CS-01305-002, First viewed by applicants' representatives on Oct. 25, 2009.

Zolpidem-d6, http://www.ejytech.com/Z_PROD.htm (p. 2, compd. 3), catalog: EJY Tech, catalog No. Z480-0411, First viewed by applicants' representatives on Oct. 25, 2009.

Gant, Thomas G., et al, Preparation and utility of substituted imidazopyridine compounds with hypnotic effects, Application No. : 12/552,254 (APX0039-201D1-US), Auspex Pharmaceuticals, Publication pending. May 30, 2007 .

Gant, Thomas G., et al, Preparation and utility of substituted imidazopyridine compounds with hypnotic effects, Application No. : 12/552,152 (APX0039-201C1-US), Auspex Pharmaceuticals, Publication pending. May 30, 2007 .

Inventorship Review Statement, Mar. 9, 2010.

* cited by examiner

PREPARATION AND UTILITY OF SUBSTITUTED IMIDAZOPYRIDINE COMPOUNDS WITH HYPNOTIC EFFECTS

RELATED APPLICATIONS

This patent application claims the benefit of U.S. Provisional Patent Application No. 60/810,935 filed Jun. 5, 2006, and is incorporated by reference in its entirety.

FIELD

The present disclosure is directed to modulators of $GABA_A$ receptors and pharmaceutically acceptable salts and prodrugs thereof, the chemical synthesis thereof, and the medical use of such compounds for the treatment and/or management of sleep disorders and/or for providing a patient in need with a hypnotic, anxiolytic or anti-convulsive effect.

BACKGROUND

Zolpidem (Ambien®) is a therapeutic agent thought to interact with the benzodiazepine receptor within the $GABA_A$ receptor complex. As such, zolpidem shares much of its pharmacology with the benzodiazepines. Zolpidem, however, is more selective, interacting primarily with the $\omega_1$ receptor, which explains the lesser degree of myorelaxant and anticonvulsant effects observed in animal studies, relative to the benzodiazepines. Eszopiclone (Lunesta®, Sepracor), indiplon (Pfizer), gaboxadol (Merck), and zaleplon (Sonata®, King) are also important members of this class of purported $GABA_A$ modulators.

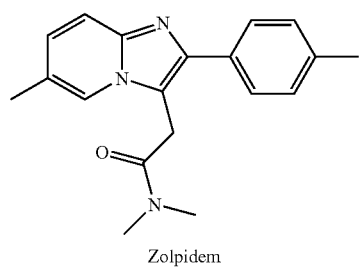

Zolpidem

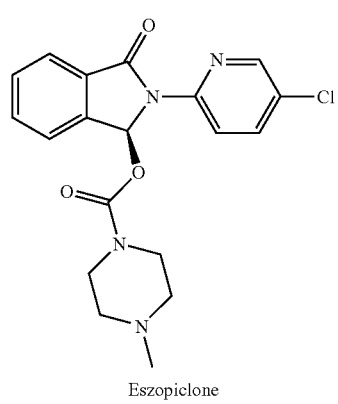

Eszopiclone

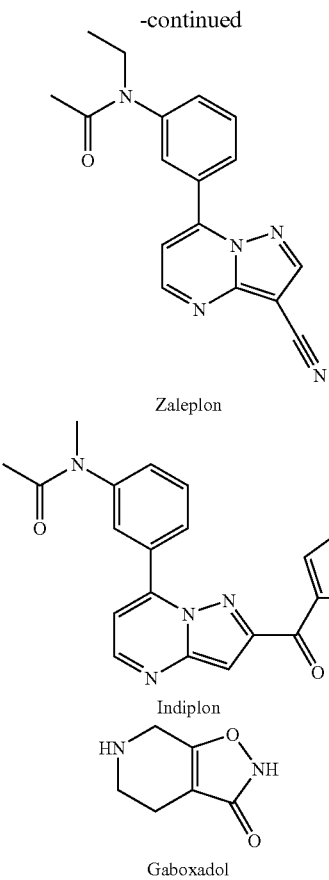

Zaleplon

Indiplon

Gaboxadol

Ambien® is converted in vivo by oxidative and conjugative degradation to multiple metabolites. The major metabolites include phase I metabolism leading to demethylation at the nitrogen center and benzylic and imidazopyridyl hydroxylation, as well as significant phase II metabolism including glucuronidation of the hydroxylated metabolites. Zolpidem is metabolized in part by polymorphically expressed isozymes of cytochrome $P_{450}$, including CYP2C9. The activity of zolpidem is cut short primarily by oxidation of the benzylic methyl group. The oxidation of this group accounts for approximately 84% of the net intrinsic clearance. The imidazopyridyl methyl group oxidation accounts for approximately another 12% of net intrinsic clearance. As such, zolpidem does not provide adequate duration of action for many patients. Consequently, its application in polypharmacy is necessarily complex, has potential for adverse events, and increases inter-patient variability in response to polypharmacy.

There is therefore a need for hypnotic agents which can provide adequate duration of action to patients in need.

SUMMARY OF THE INVENTION

Described herein are deuterated modulators of $GABA_A$ receptors. In one embodiment, the deuterium enrichment occurs at a specific position on the modulator. In another embodiment, the deuterium enrichment is no less than about 1%. In a further embodiment, the deuterium enrichment is no less than about 10%. In yet a further embodiment, the deuterium enrichment is no less than about 20%. In one embodiment, the deuterium enrichment is no less than about 50%. In a further embodiment, the deuterium enrichment is no less than about 70%. In a further embodiment, the deuterium enrichment is no less than about 80%. In yet a further embodiment, the deuterium enrichment is no less than about 90%. In a further embodiment, the deuterium enrichment is no less than about 95%. In one embodiment, the deuterated modulator has a slower rate of metabolism than the corresponding protiated inhibitor.

Further described herein are deuterated analogs of zolpidem, eszopiclone, indiplon, gaboxadol, and zaleplon, including, for each of the aforementioned compounds, a single enantiomer, a mixture of a (+)-enantiomer and a (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug. In one embodiment, the deuterium enrichment occurs at a specific position on the analog. In another embodiment, the deuterium enrichment is no less than about 1%. In a further embodiment, the deuterium enrichment is no less than about 10%. In yet a further embodiment, the deuterium enrichment is no less than about 20%. In another embodiment, the deuterium enrichment is no less than about 50%. In yet another embodiment, the deuterium enrichment is no less than about 70%. In a further embodiment, the deuterium enrichment is no less than about 80%. In yet a further embodiment, the deuterium enrichment is no less than about 90%. In a further embodiment, the deuterium enrichment is no less than about 95%. In one embodiment, the deuterated compound has a slower rate of metabolism than the corresponding protiated compound.

Provided herein are compounds of Formula 1:

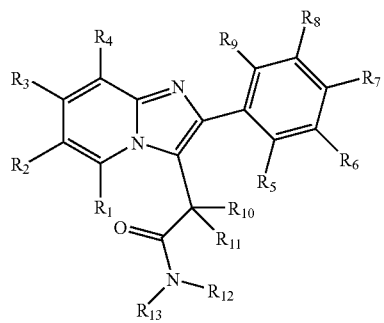

Formula 1 or a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof wherein:

$R_1$, $R_3$, $R_4$, $R_5$, $R_6$, $R_8$, $R_9$, $R_{10}$, and $R_{11}$ are independently selected from the group consisting of hydrogen and deuterium;

$R_2$, $R_7$, $R_{12}$, and $R_{13}$ are independently selected from the group consisting of —$CH_3$, —$CH_2D$, —$CHD_2$, and —$CD_3$;

provided that compounds of Formula 1 contain at least one deuterium atom; and provided that deuterium enrichment in compounds of Formula 1 is at least about 1%.

In one embodiment is a compound selected from the group consisting of:

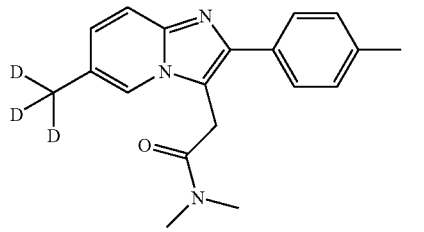

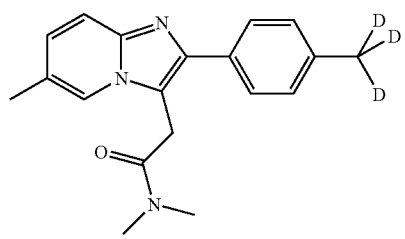

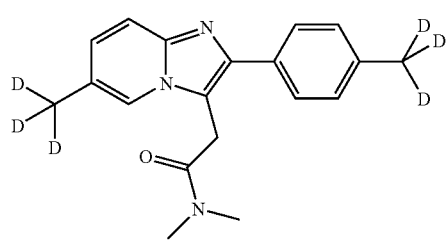

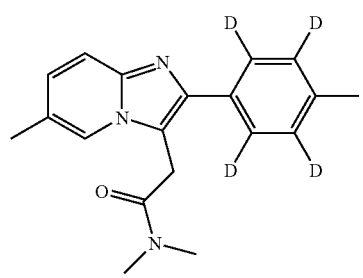

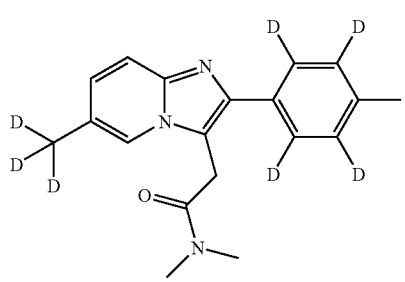

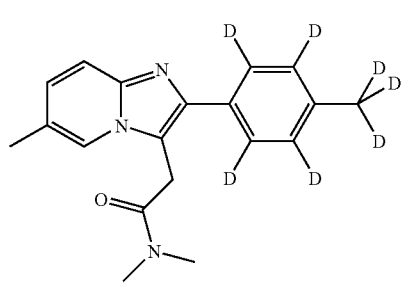

-continued
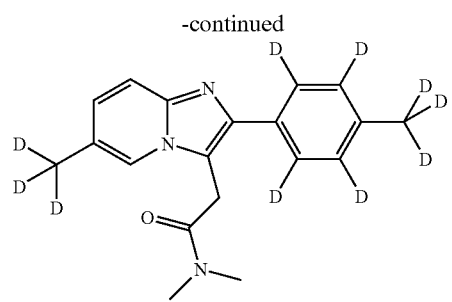
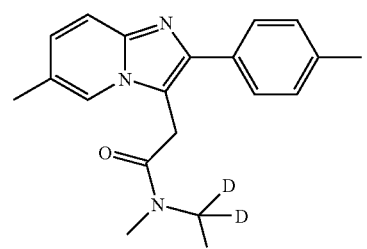
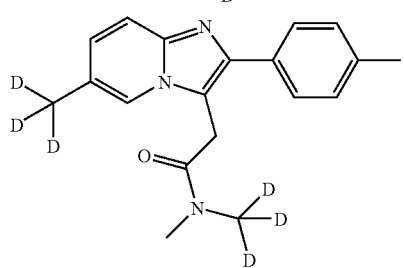
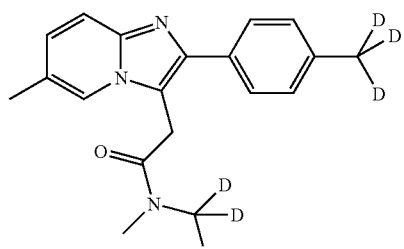
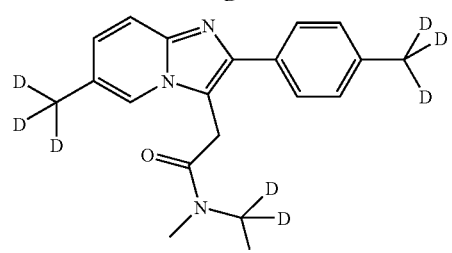
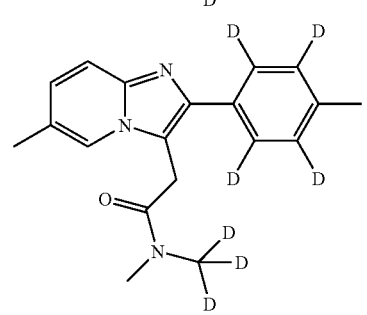
-continued
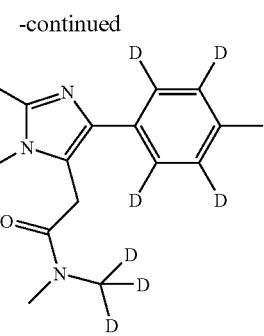
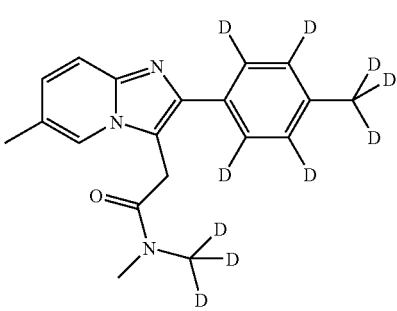
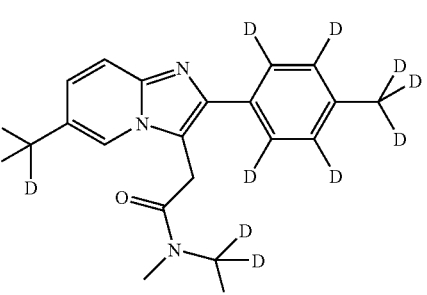
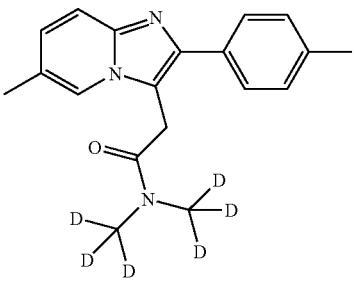
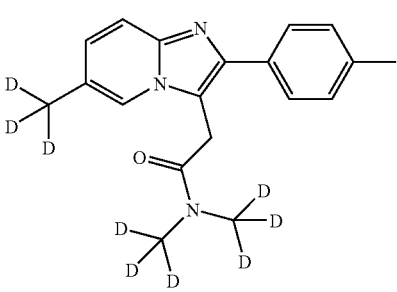

-continued
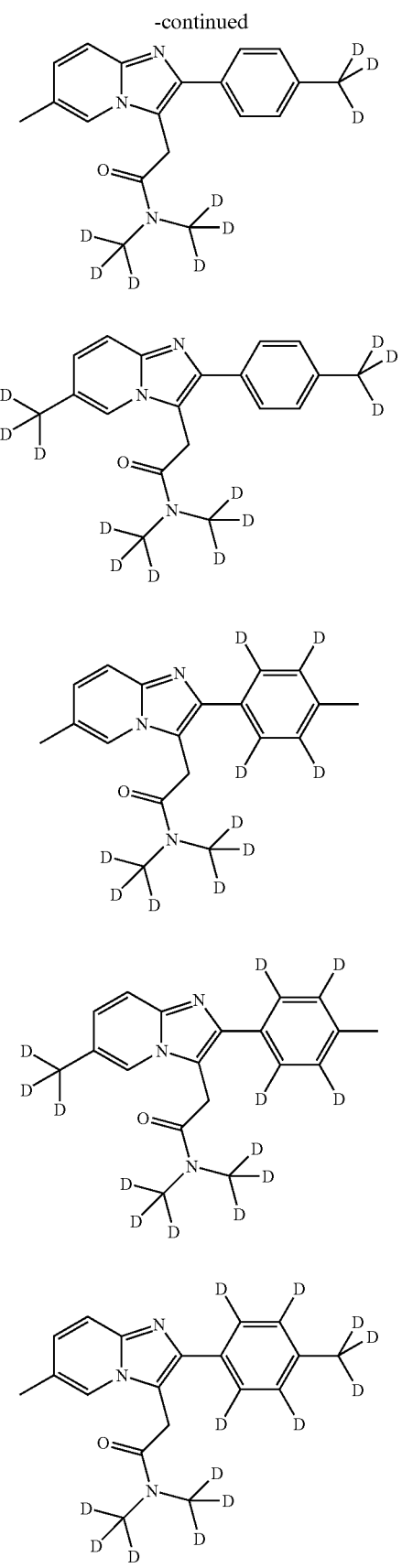
-continued
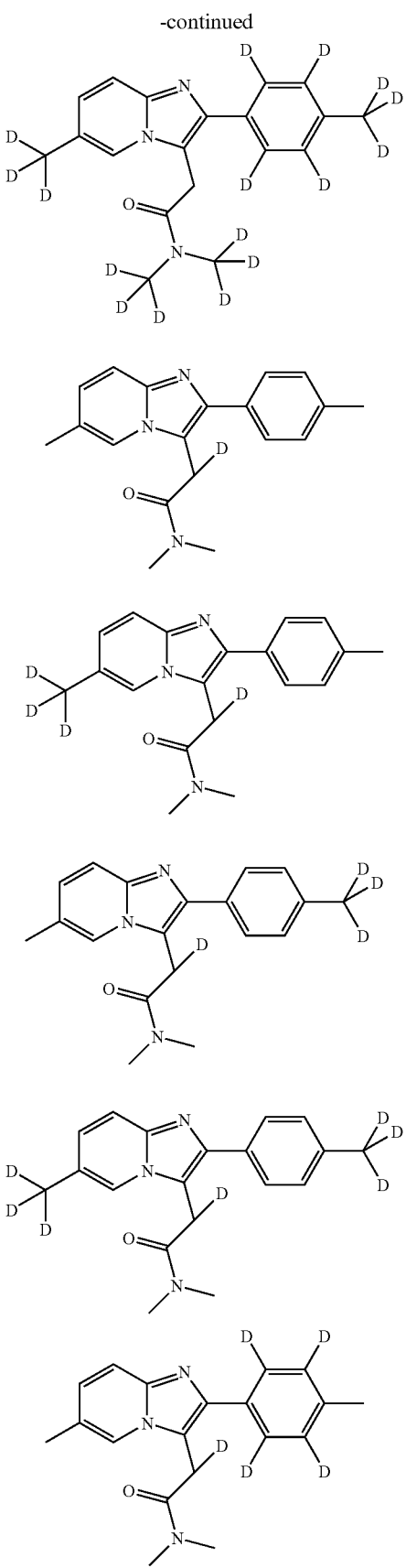

-continued
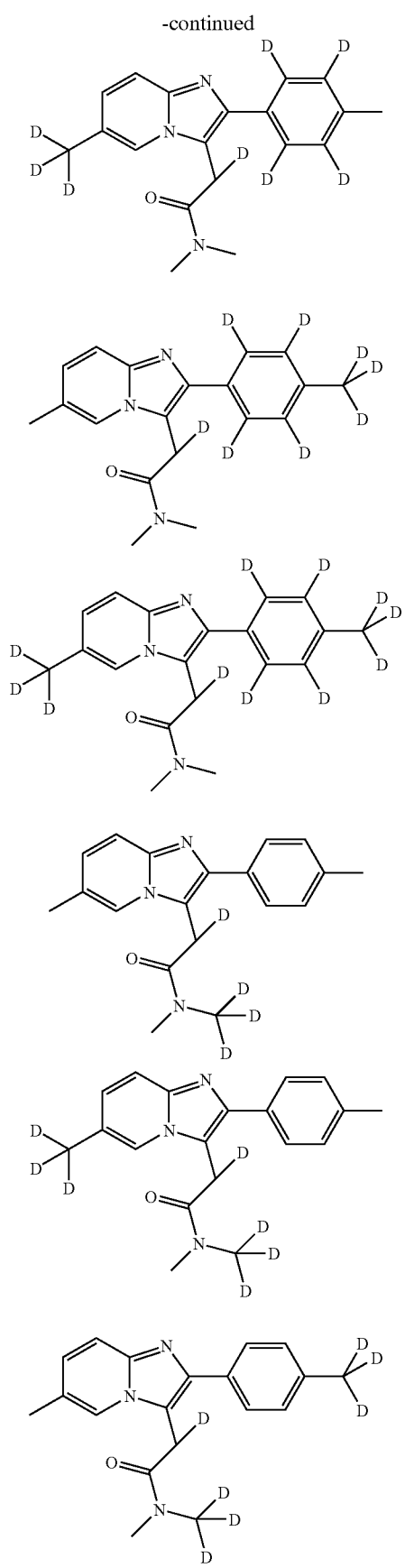
-continued
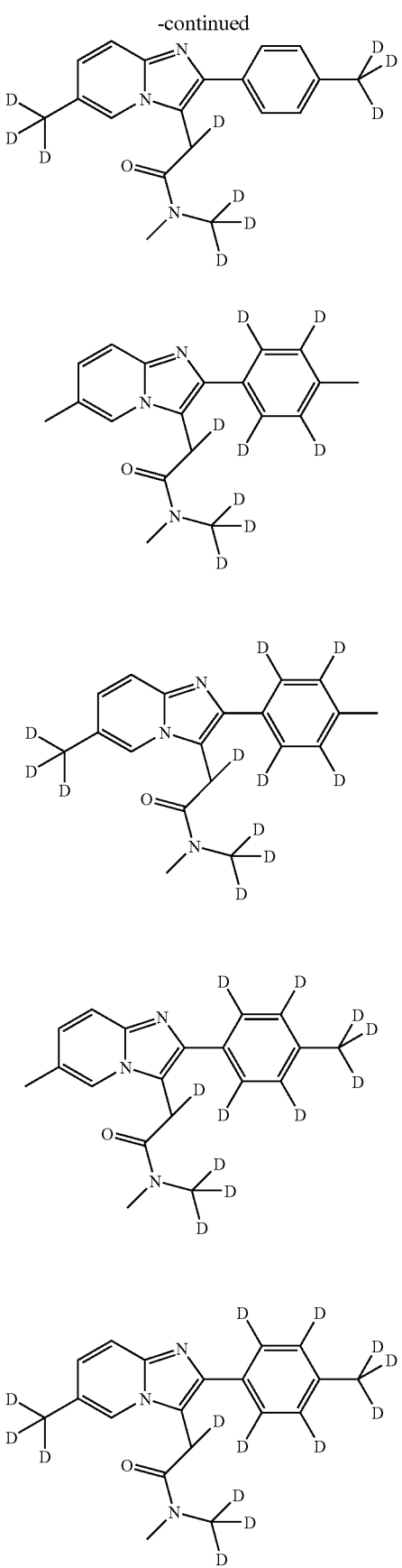

-continued
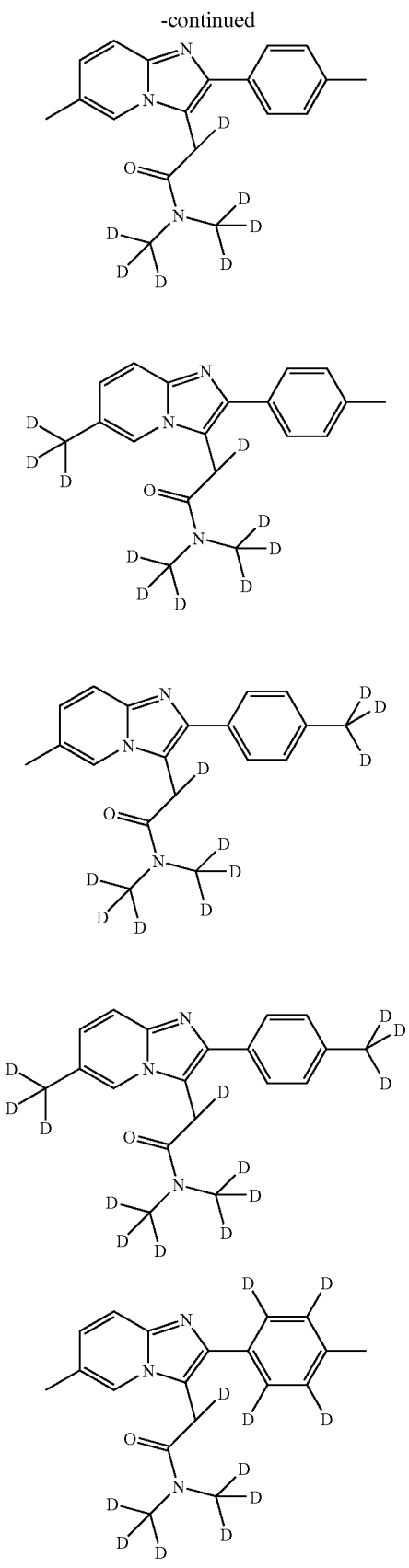
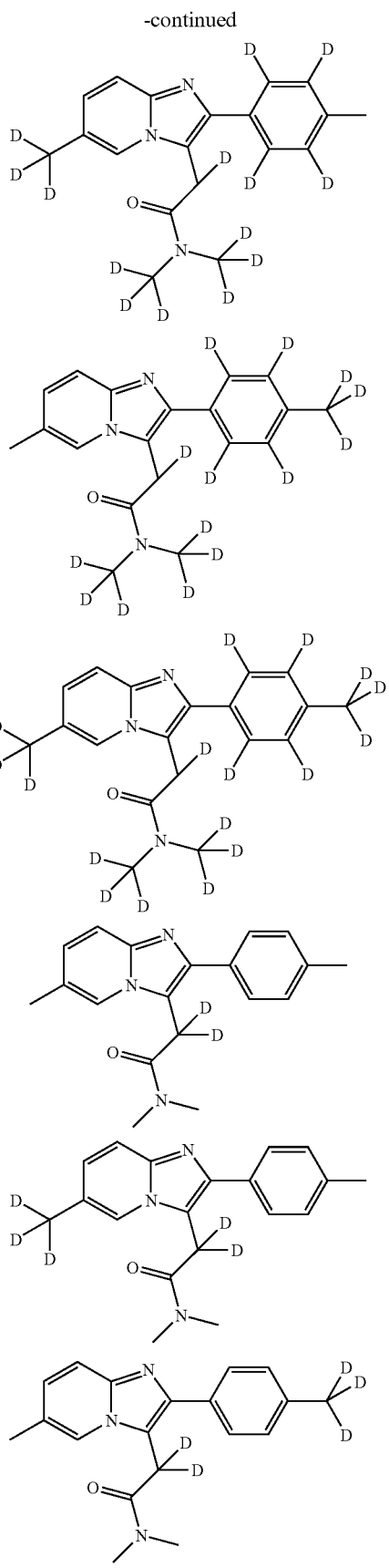

-continued
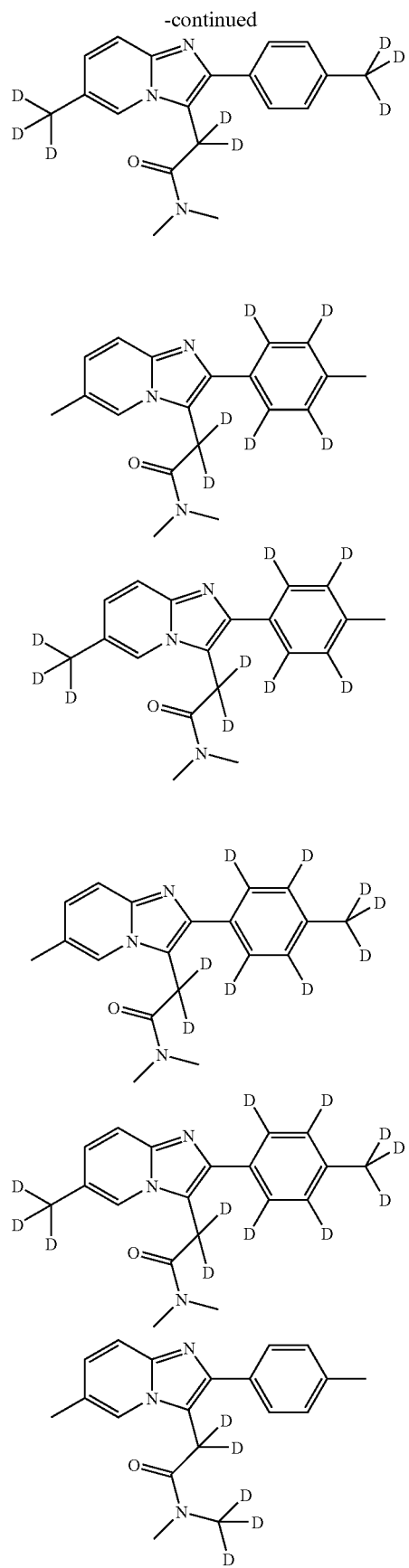
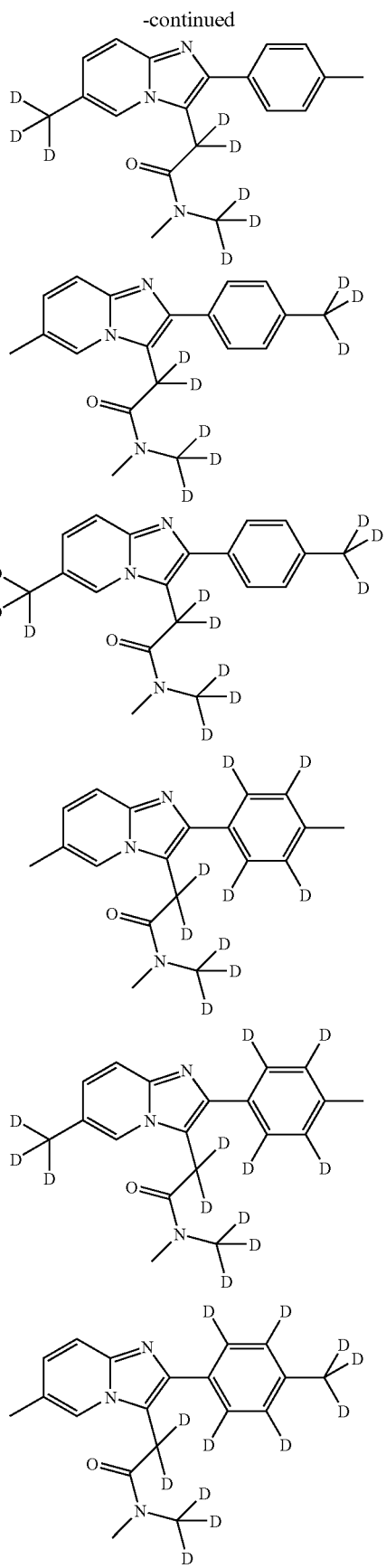

-continued
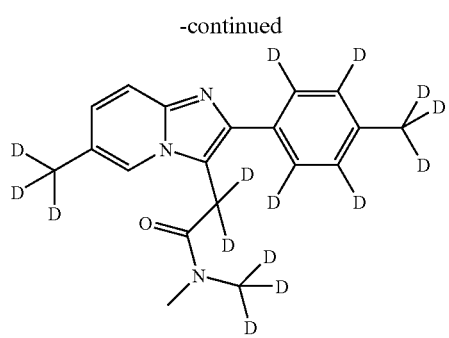
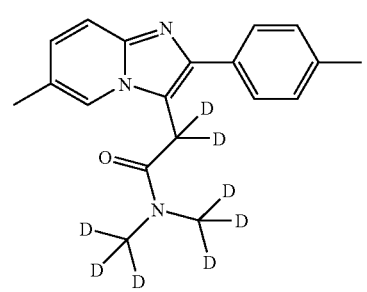
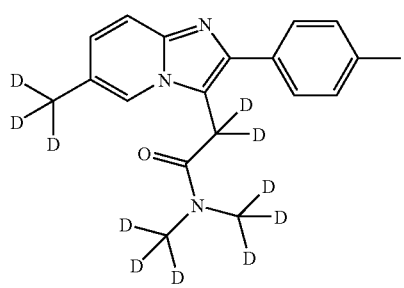
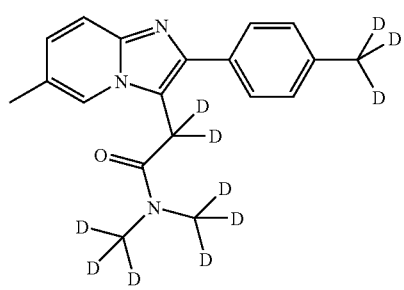
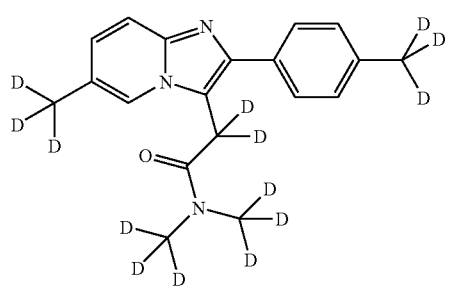
-continued
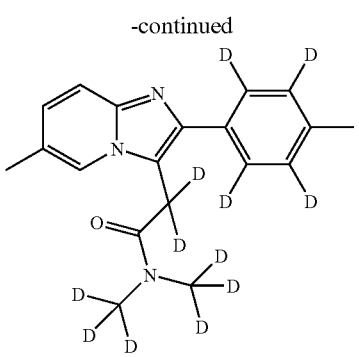
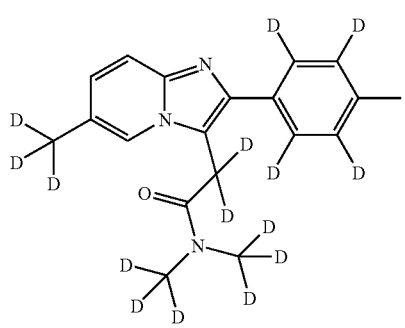
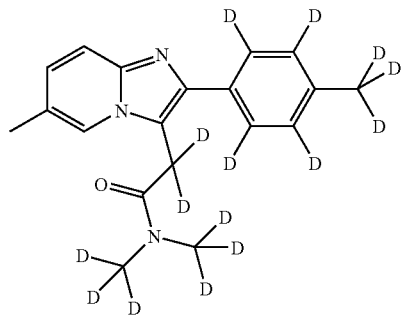
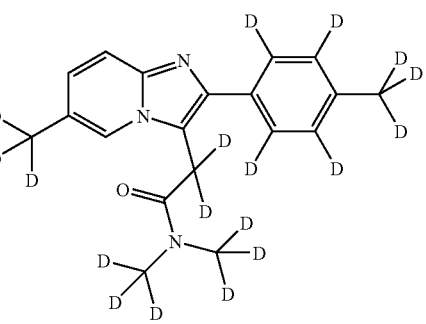
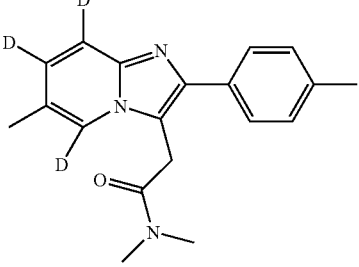

-continued
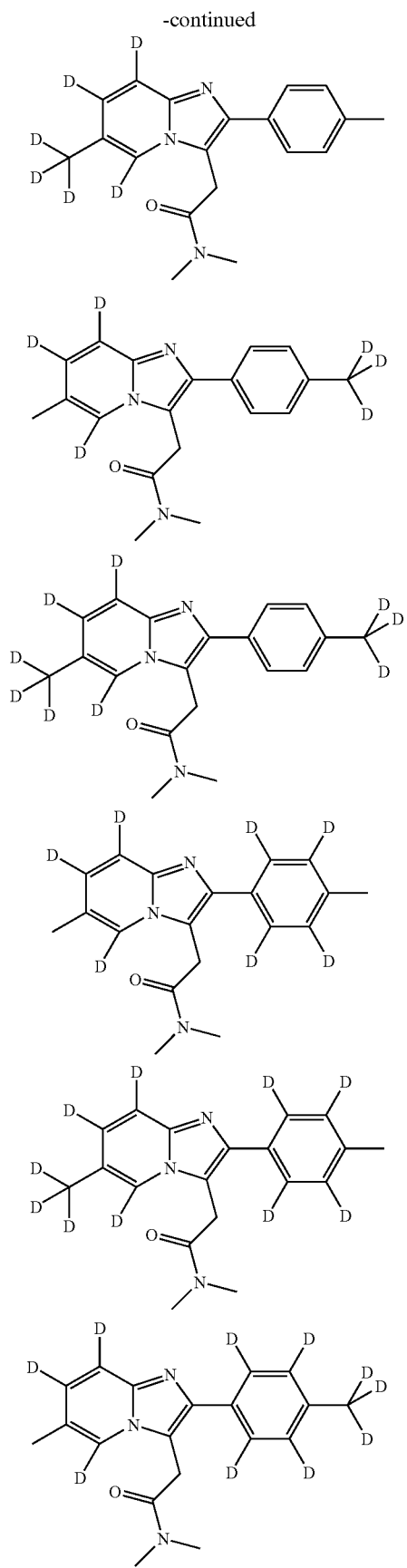
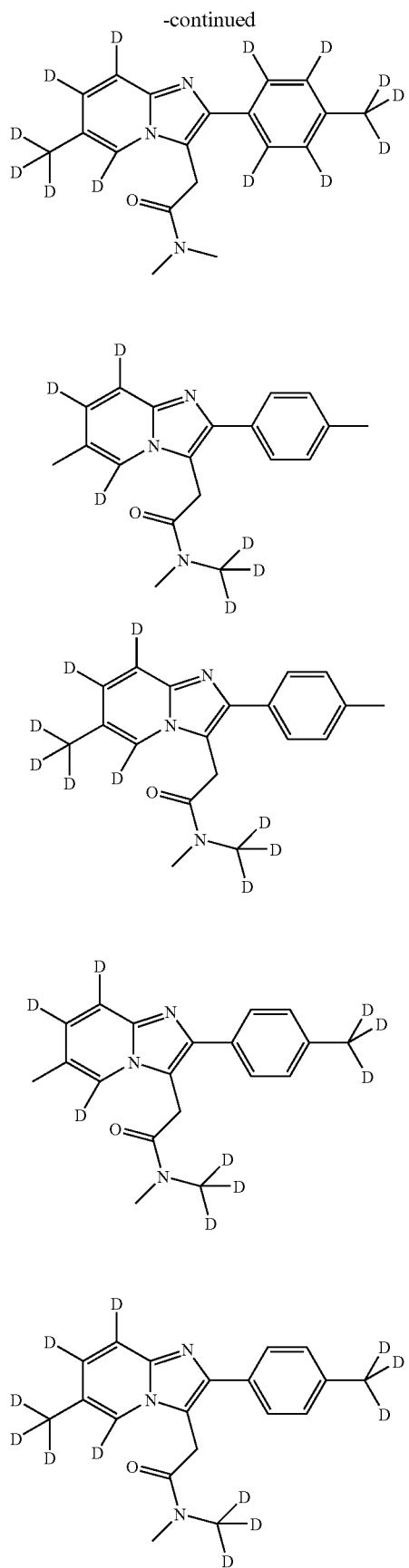

-continued
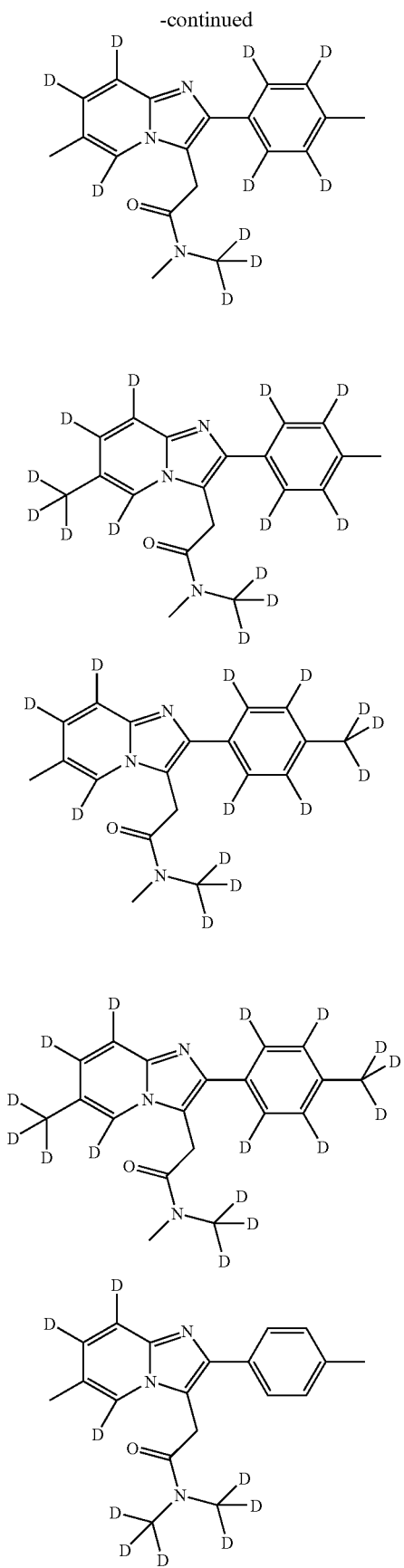
-continued
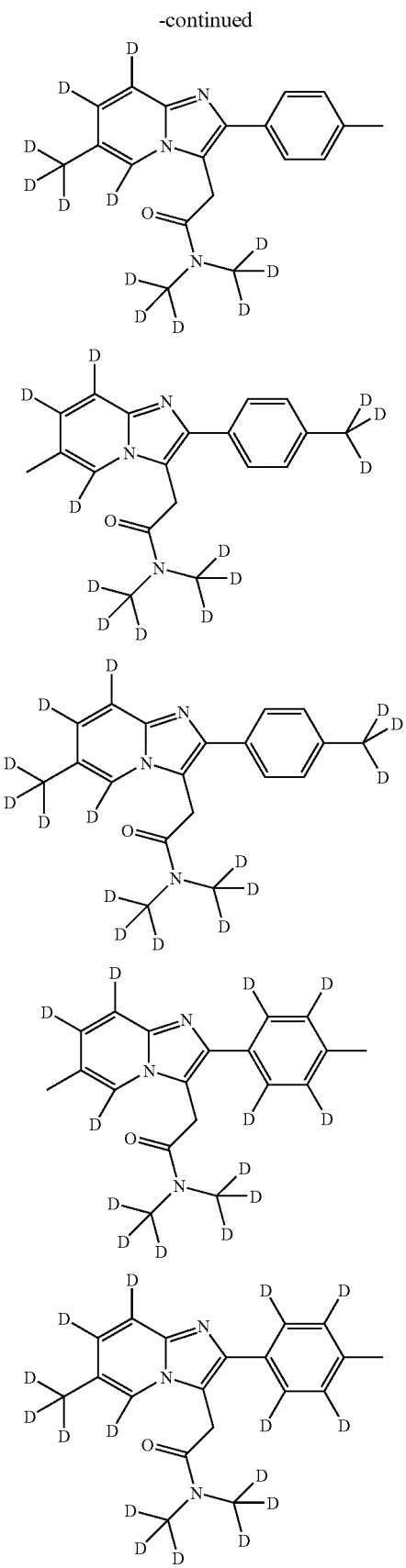

-continued
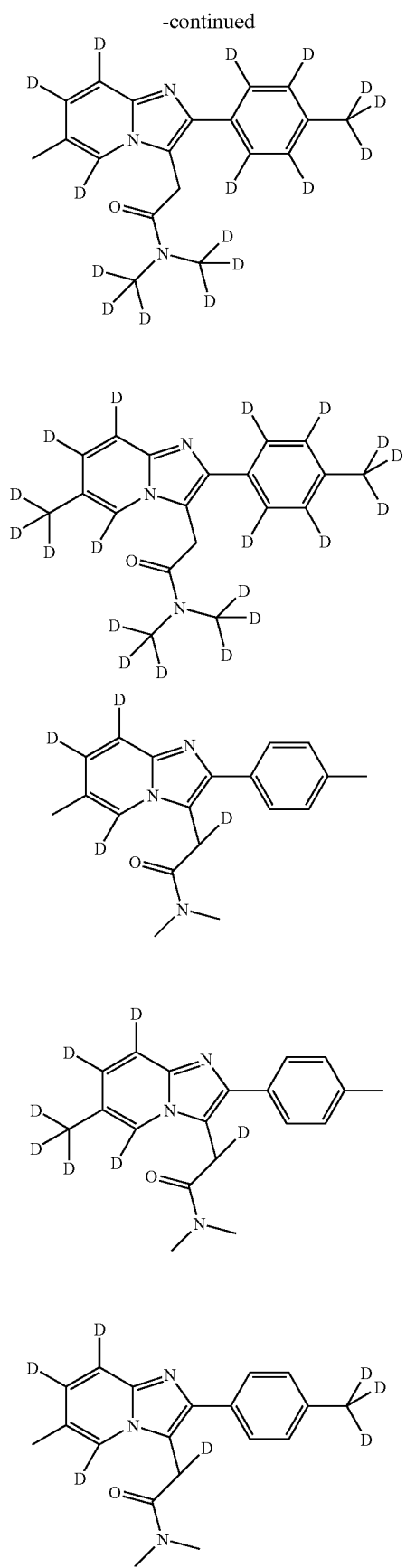
-continued
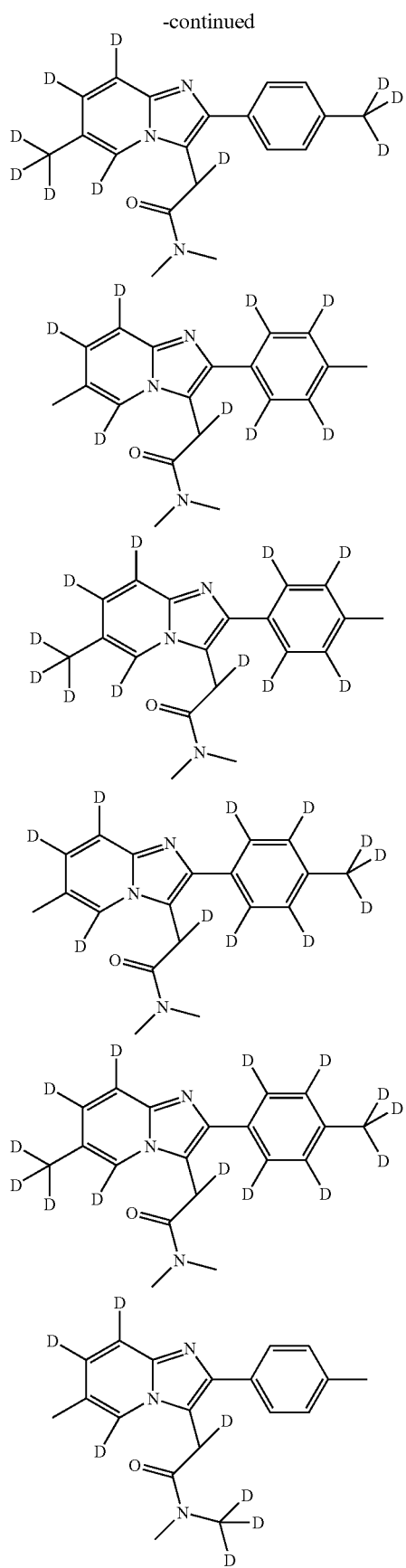

-continued
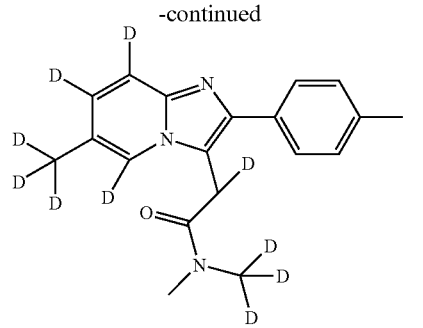
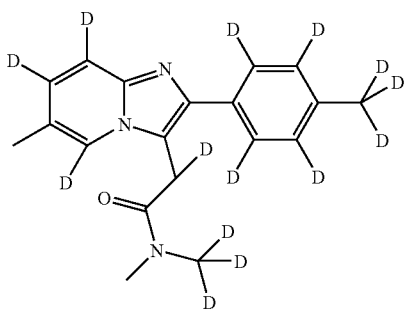
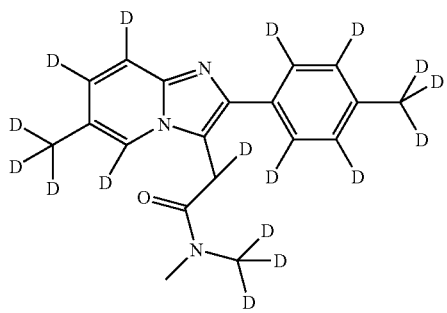
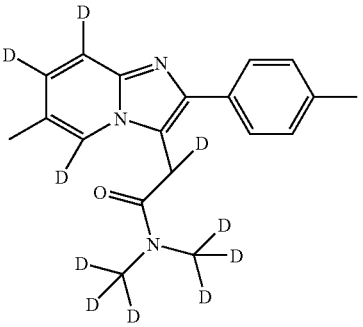
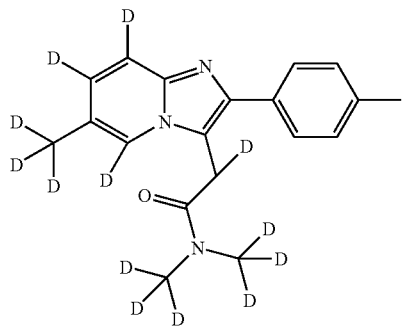
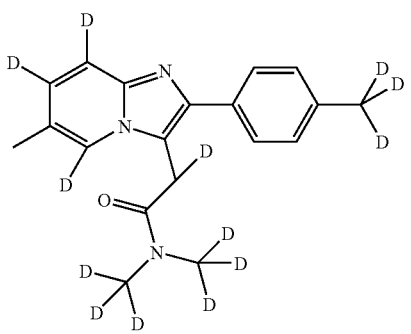

-continued
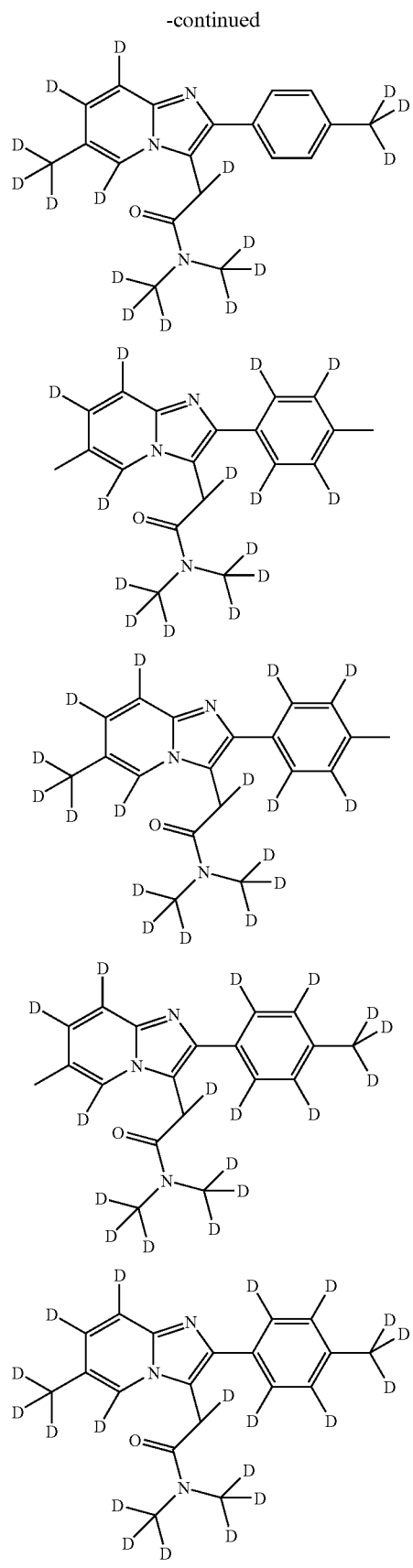
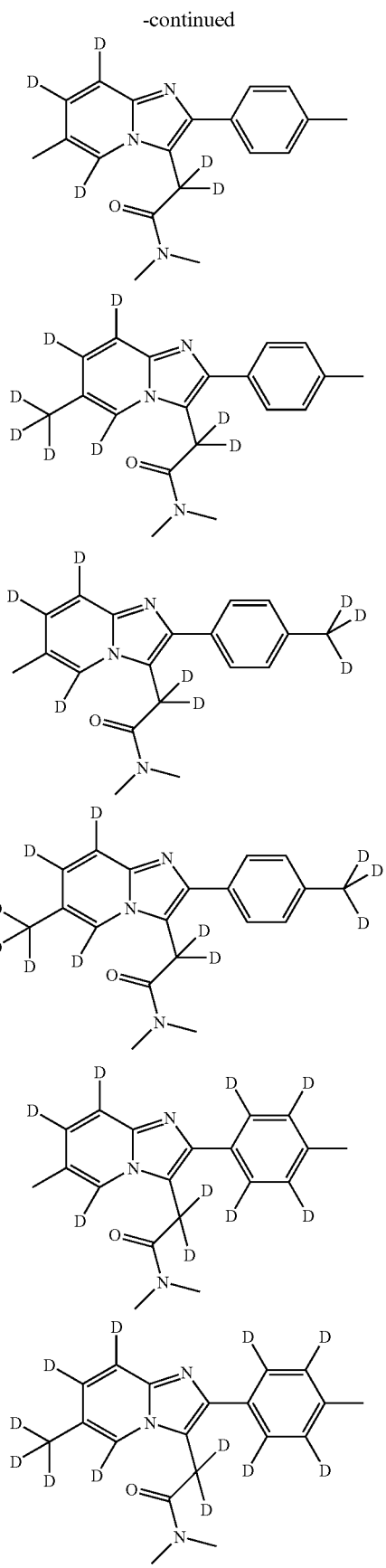

-continued
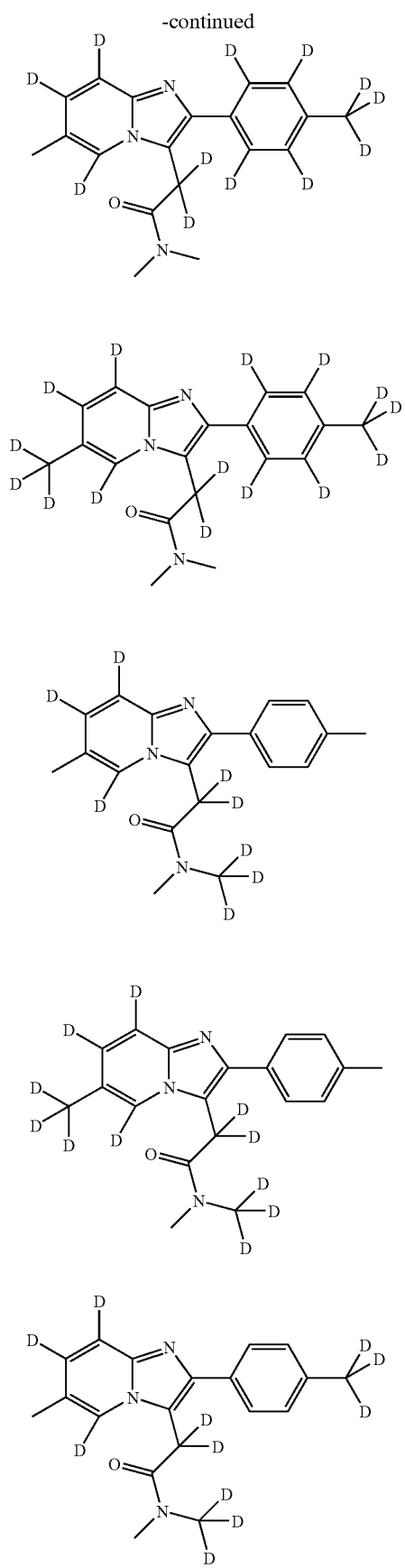
-continued
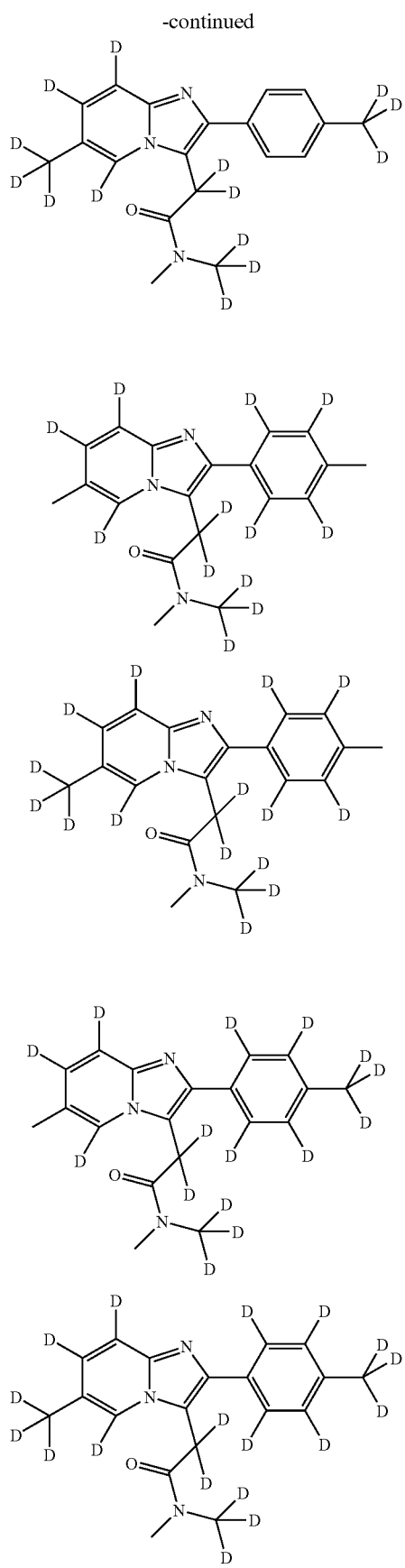

-continued

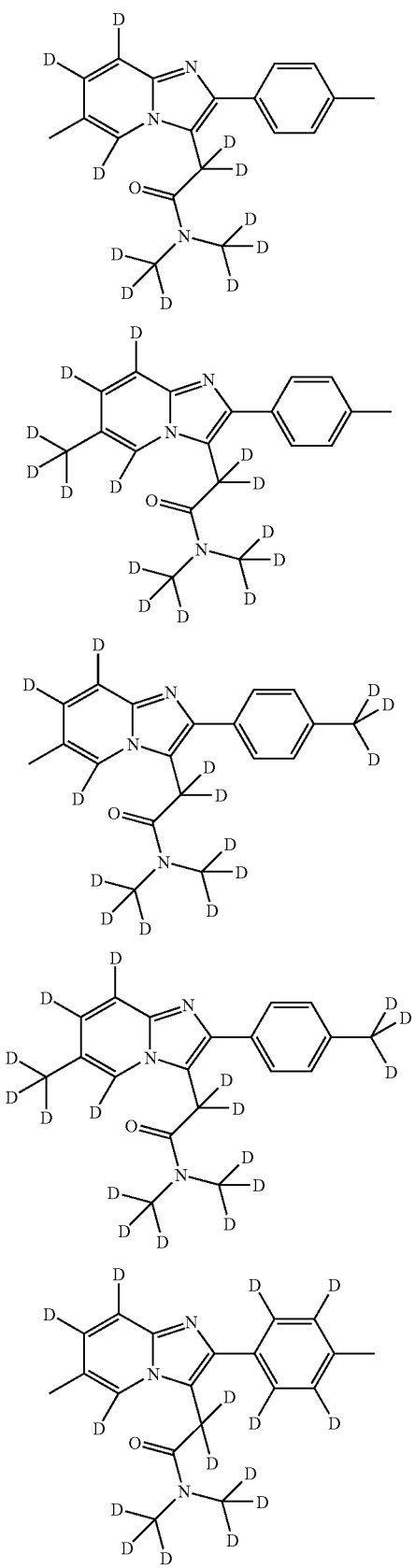

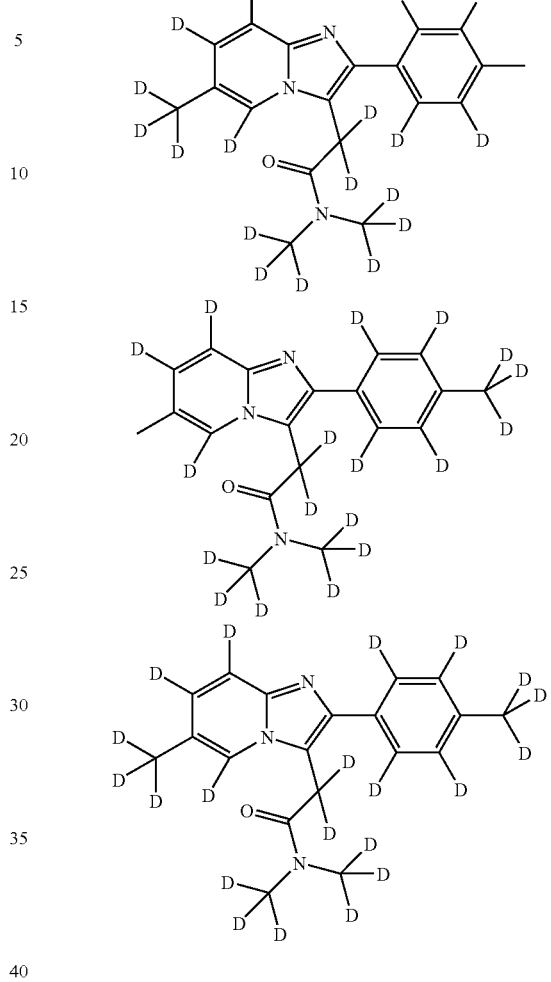

or a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof.

In one embodiment, the deuterium enrichment is no less than about 1%. In a further embodiment, the deuterium enrichment is no less than about 10%. In a further embodiment, the deuterium enrichment is no less than about 20%. In a further embodiment, the deuterium enrichment is no less than about 50%. In a further embodiment, the deuterium enrichment is no less than about 70%. In a further embodiment, the deuterium enrichment is no less than about 80%. In a further embodiment, the deuterium enrichment is no less than about 90%. In a further embodiment, the deuterium enrichment is no less than about 95%. In one embodiment, the deuterated compound has a slower rate of metabolism than the corresponding protiated compound.

Also provided herein is a method of treating a mammal suffering from a disease or condition involving a benzodiazepine receptor, comprising administering to the mammal a therapeutically effective amount of a compound of Formula 1

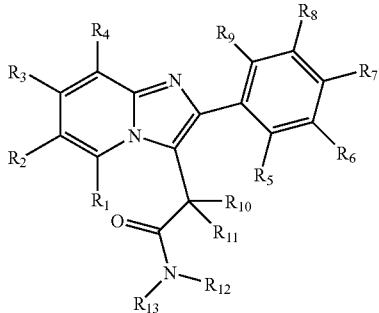

Formula 1 or a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof wherein:

$R_1$, $R_3$, $R_4$, $R_5$, $R_6$, $R_8$, $R_9$, $R_{10}$, and $R_{11}$ are independently selected from the group consisting of hydrogen and deuterium;

$R_2$, $R_7$, $R_{12}$, and $R_{13}$ are independently selected from the group consisting of —$CH_3$, —$CH_2D$, —$CHD_2$, and —$CD_3$;

provided that the compound of Formula 1 contains at least one deuterium atom; and provided that deuterium enrichment in the compound of Formula 1 is at least about 1%;

so as to affect decreased inter-individual variation in plasma levels of the compound or a metabolite thereof as compared to the non-isotopically enriched compound.

In one aspect is a method of treating a mammal suffering from a disease or condition involving a benzodiazepine receptor, comprising administering to the mammal a therapeutically effective amount of a compound of Formula 1:

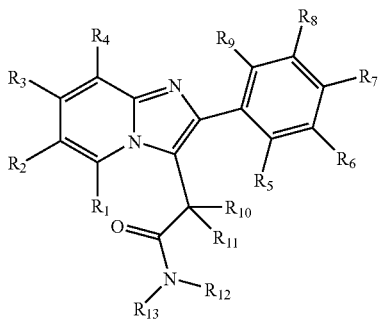

Formula 1 or a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof wherein:

$R_1$, $R_3$, $R_4$, $R_5$, $R_6$, $R_8$, $R_9$, $R_{10}$, and $R_{11}$ are independently selected from the group consisting of hydrogen and deuterium;

$R_2$, $R_7$, $R_{12}$, and $R_{13}$ are independently selected from the group consisting of —$CH_3$, —$CH_2D$, —$CHD_2$, and —$CD_3$;

provided that said compound of Formula 1 contains at least one deuterium atom; and provided that deuterium enrichment in said compound of Formula 1 is at least about 1%;

so as to affect increased average plasma levels of said compound per dosage unit thereof as compared to the non-isotopically enriched compound.

In one embodiment is a method wherein the disease or condition is selected from the group consisting of a sleep disorder and a disease in which a hypnotic, an anxiolytic or an anti-convulsive effect is beneficial.

In one aspect is a method of treating a mammal suffering from a disease or condition involving a benzodiazepine receptor, comprising administering a therapeutically effective amount of a compound of Formula 1:

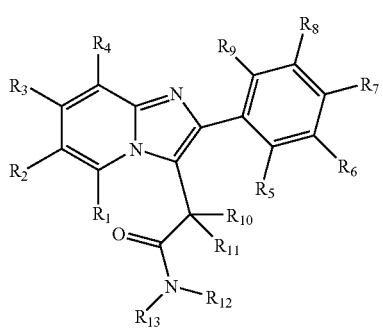

Formula 1 or a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof wherein:

$R_1$, $R_3$, $R_4$, $R_5$, $R_6$, $R_8$, $R_9$, $R_{10}$, and $R_{11}$ are independently selected from the group consisting of hydrogen and deuterium;

$R_2$, $R_7$, $R_{12}$, and $R_{13}$ are independently selected from the group consisting of —$CH_3$, —$CH_2D$, —$CHD_2$, and —$CD_3$;

provided that said compound of Formula 1 contains at least one deuterium atom; and provided that deuterium enrichment in said compound of Formula 1 is at least about 1%;

so as to affect decreased average plasma levels of at least one metabolite of the compound per dosage unit thereof as compared to the non-isotopically enriched compound.

In another aspect is a method of treating a mammal suffering from a disease or condition involving a benzodiazepine receptor, comprising administering a therapeutically effective amount of a compound of Formula 1:

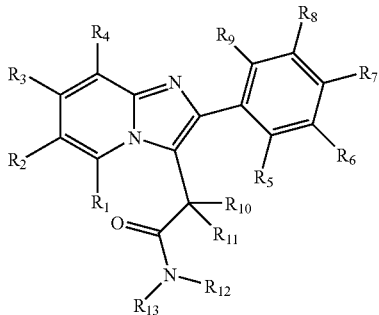

Formula 1 or a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof wherein:

$R_1$, $R_3$, $R_4$, $R_5$, $R_6$, $R_8$, $R_9$, $R_{10}$, and $R_{11}$ are independently selected from the group consisting of hydrogen and deuterium;

$R_2$, $R_7$, $R_{12}$, and $R_{13}$ are independently selected from the group consisting of —$CH_3$, —$CH_2D$, —$CHD_2$, and —$CD_3$;

provided that said compound of Formula 1 contains at least one deuterium atom; and provided that deuterium enrichment in said compound of Formula 1 is at least about 1%;

so as to affect a decreased metabolism by at least one polymorphically-expressed cytochrome $P_{450}$ isoform in mammalian subjects per dosage unit thereof as compared to the non-isotopically enriched compound.

In one aspect is a method of treating a mammal suffering from a disease or condition involving a benzodiazepine receptor, comprising administering a therapeutically effective amount of a compound of Formula 1:

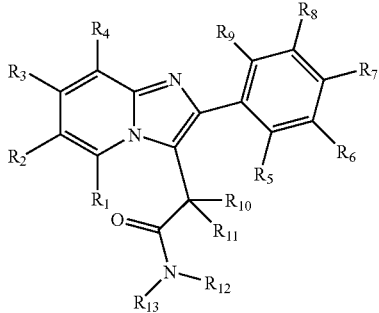

Formula 1 or a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof wherein:

$R_1$, $R_3$, $R_4$, $R_5$, $R_6$, $R_8$, $R_9$, $R_{10}$, and $R_{11}$ are independently selected from the group consisting of hydrogen and deuterium;

$R_2$, $R_7$, $R_{12}$, and $R_{13}$ are independently selected from the group consisting of —$CH_3$, —$CH_2D$, —$CHD_2$, and —$CD_3$;

provided that said compound of Formula 1 contains at least one deuterium atom; and provided that deuterium enrichment in said compound of Formula 1 is at least about 1%;

so as to affect a decreased inhibition of at least one cytochrome $P_{450}$ isoform in mammalian subjects per dosage unit thereof as compared to the non-isotopically enriched compound.

In one embodiment is a method wherein the cytochrome $P_{450}$ isoform is selected from the group consisting of CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R1, CYP2S1, CYP3A4, CYP3A5, CYP3A5P1, CYP3A5P2, CYP3A7, CYP4A11, CYP4B1, CYP4F2, CYP4F3, CYP4F8, CYP4μl, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, and CYP51, In one embodiment is a method wherein the cytochrome $P_{450}$ isoform is selected from the group consisting of CYP2C8, CYP2C9, CYP2C19, and CYP2D6.

In another aspect is a method of treating a mammal suffering from a disease or condition involving a benzodiazepine receptor, comprising administering a therapeutically effective amount of a compound of Formula 1:

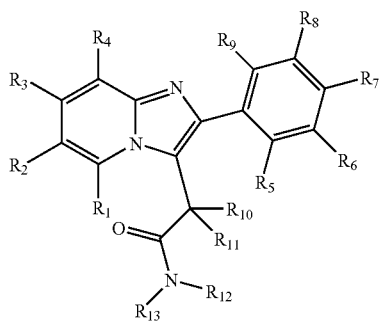

Formula 1 or a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof wherein:

$R_1$, $R_3$, $R_4$, $R_5$, $R_6$, $R_8$, $R_9$, $R_{10}$, and $R_{11}$ are independently selected from the group consisting of hydrogen and deuterium;

$R_2$, $R_7$, $R_{12}$, and $R_{13}$ are independently selected from the group consisting of —$CH_3$, —$CH_2D$, —$CHD_2$, and $CD_3$;

provided that said compound of Formula 1 contains at least one deuterium atom; and provided that deuterium enrichment in said compound of Formula 1 is at least about 1%;

so as to elicit an improved clinical effect during the treatment in said mammal per dosage unit thereof as compared to the non-isotopically enriched compound.

Also disclosed herein are pharmaceutical compositions comprising a therapeutically effective amount of a compound of Formula 1, or the (−)-enantiomer of a compound of Formula 1, or the (+)-enantiomer of a compound of Formula 1, or a pharmaceutically acceptable salt, solvate, or prodrug thereof, and a pharmaceutically acceptable excipient or carrier.

In one embodiment the pharmaceutical composition is a suitable oral, parenteral, or intravenous infusion administration. In another embodiment is a pharmaceutical composition wherein oral administration comprises administering a tablet or a capsule. In another embodiment is a pharmaceutical composition wherein a compound of Formula 1 is administered in a dose of about 0.1 milligram to about 100 milligram total daily.

Further, disclosed herein are methods of treating a mammal suffering from a disease or condition involving a benzodiazepine receptor, comprising administering to the mammal a therapeutically effective amount of a compound of Formula 1:

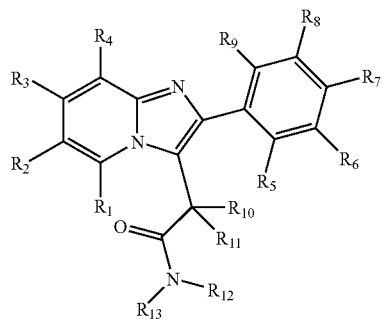

Formula 1 or a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof, or a pharmaceutically acceptable salt, solvate, or prodrug thereof wherein:

$R_1$, $R_3$, $R_4$, $R_5$, $R_6$, $R_8$, $R_9$, $R_{10}$, and $R_{11}$ are independently selected from the group consisting of hydrogen and deuterium;

$R_2$, $R_7$, $R_{12}$, and $R_{13}$ are independently selected from the group consisting of —$CH_3$, —$CH_2D$, —$CHD_2$, and —$CD_3$;

provided that said compound of Formula 1 contains at least one deuterium atom; and provided that deuterium enrichment in said compound of Formula 1 is at least about 1%.

In addition, disclosed herein are methods of treating a mammalian subject having, suspected of having, or being prone to a disease or condition, such as a disease or condition selected from the group consisting of a sleep disorder and/or a disease in which a hypnotic, an anxiolytic or an anti-convulsive effect is beneficial.

Also provided herein are articles of manufacture and kits containing compounds described herein. By way of example only a kit or article of manufacture can include a container (such as a bottle) with a desired amount of a compound (or pharmaceutical composition of a compound) described herein. Such a kit or article of manufacture can further include instructions for using the compound (or pharmaceutical composition of a compound) described herein. The instructions can be attached to the container, or can be included in a package (such as a box or a plastic or foil bag) holding the container.

In another aspect is the use of a compound described herein in the manufacture of a medicament for treating a disease or condition in an animal in which a benzodiazapine receptor contributes to the pathology and/or symptomology of the disease or condition. In a further or alternative embodiment, said disease or condition is non-specific pain, tension-type pain, headache, migraine, lower back pain, sciatica, dental pain, muscular pain, pain associated with acute soft tissue injuries, bursitis, tendonitis, lumbago, periarthritis, tennis elbow, sprains, strains, muscular problems associated with sports injuries, muscular problems associated with accidents, period pain, primary dysmenorrhoea, acute sore throat pain, osteoartlritis, rheumatoid arthritis, cancer, any disorder requiring analgesic response, any disorder requiring anti-inflammatory response, any disorder requiring antipyretic response, any conditions mediated by cyclooxygenase, cystic fibrosis, dementia, Alzheimer's disease, and may be used as an anesthetic, analgesic, entheogen, therapeutic cataleptic, and neuroprotectant.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION

To facilitate understanding of the disclosure set forth herein, a number of terms are defined below.

As used herein, the singular forms "a," "an," and "the" may refer to plural articles unless specifically stated otherwise. Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term herein, those in this section prevail unless stated otherwise.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

The terms "treat," "treating," and "treatment" are meant to include alleviating or abrogating a disorder, disease, or condition; or one or more of the symptoms associated with the disorder, disease, or condition; or alleviating or eradicating the cause(s) of the disorder, disease, or condition itself.

The terms "prevent," "preventing," and "prevention" refer to a method of delaying or precluding the onset of a disorder, disease, or condition; and/or its attendant symptoms, barring a subject from acquiring a disease or reducing a subject's risk of acquiring a disorder, disease, or condition.

The term "therapeutically effective amount" refers to the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a cell, tissue, system, animal, or human that is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition; Lippincott Williams & Wilkins: Philadelphia, Pa., 2005; *Handbook of Pharmaceutical Excipients,* 5th Edition; Rowe et al., Eds., The Pharmaceutical Press and the American Pharmaceutical Association: 2005; and *Handbook of Pharmaceutical Additives,* 3rd Edition; Ash and Ash Eds., Gower Publishing Company: 2007; *Pharmaceutical Preformulation and Formulation,* Gibson Ed., CRC Press LLC: Boca Raton, Fla., 2004).

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "deuterium enrichment" refers to the percentage of incorporation of deuterium at a given position in a molecule in the place of hydrogen. For example, deuterium enrichment of about 1% at a given position means that about 1% of molecules in a given sample contain deuterium at the specified position. Because the naturally occurring distribution of deuterium is about 0.0156%, deuterium enrichment at any positions in a compound synthesized using non-enriched starting materials is about 0.0156%. The deuterium enrichment can be determined using conventional analytical methods known to one of ordinary skill in the art, including mass spectrometry and nuclear magnetic resonance spectroscopy.

The term "isotopic enrichment" refers to the percentage of incorporation of a less prevalent isotope of an element at a given position in a molecule in the place of the more prevalent isotope of the element.

The term "non-isotopically enriched" refers to a molecule in which the percentages of the various isotopes are substantially the same as the naturally occurring percentages.

The terms "substantially pure" and "substantially homogeneous" mean sufficiently homogeneous to appear free of readily detectable impurities as determined by standard analytical methods used by one of ordinary skill in the art, including, but not limited to, thin layer chromatography (TLC), gel electrophoresis, high performance liquid chromatography (HPLC), nuclear magnetic resonance (NMR), and mass spectrometry (MS); or sufficiently pure such that further purification would not detectably alter the physical and chemical properties, or biological and pharmacological properties, such as enzymatic and biological activities, of the substance. In certain embodiments, "substantially pure" or "substantially homogeneous" refers to a collection of molecules, wherein at least about 50%, at least about 70%, at least about 80%, at least about 90%, at least about 95%, at least about 98%, at least about 99%, or at least about 99.5% of the molecules are a single compound, including a racemic mixture or single stereoisomer thereof, as determined by standard analytical methods The term "about" or "approximately" means an acceptable error for a particular value as determined by one of ordinary skill in the art, which depends in part on how the value is measured or determined. In certain embodiments, "about" can mean with 1 or more standard deviations.

The terms "active ingredient" and "active substance" refer to a compound, which is administered, alone or in combination with one or more pharmaceutically acceptable excipients, to a subject for treating, preventing, or ameliorating one or more symptoms of a disorder or disease.

The terms "drug," "therapeutic agent," and "chemotherapeutic agent" refer to a compound, or a pharmaceutical composition thereof, which is administered to a subject for treating, preventing, or ameliorating one or more symptoms of a disorder or disease.

The term "release controlling excipient" refers to an excipient whose primary function is to modify the duration or place of release of the active substance from a dosage form as compared with a conventional immediate release dosage form.

The term "non-release controlling excipient" refers to an excipient whose primary function do not include modifying the duration or place of release of the active substance from a dosage form as compared with a conventional immediate release dosage form.

The term "halogen", "halide" or "halo" includes fluorine, chlorine, bromine, and iodine.

The terms "alkyl" and "substituted alkyl" are interchangeable and include substituted, optionally substituted and unsubstituted $C_1$-$C_{10}$ straight chain saturated aliphatic hydrocarbon groups, substituted, optionally substituted and unsubstituted $C_2$-$C_{10}$ straight chain unsaturated aliphatic hydrocarbon groups, substituted, optionally substituted and unsubstituted $C_2$-$C_{10}$ branched saturated aliphatic hydrocarbon groups, substituted and unsubstituted $C_2$-$C_{10}$ branched unsaturated aliphatic hydrocarbon groups, substituted, optionally substituted and unsubstituted $C_3$-$C_8$ cyclic saturated aliphatic hydrocarbon groups, substituted, optionally substituted and unsubstituted $C_5$-$C_8$ cyclic unsaturated aliphatic hydrocarbon groups having the specified number of carbon atoms. For example, the definition of "alkyl" shall include but is not limited to: methyl (Me), trideuteromethyl (—$CD_3$), ethyl (Et), propyl (Pr), butyl (Bu), pentyl, hexyl, heptyl, octyl, nonyl, decyl, undecyl, ethenyl, propenyl, butenyl, penentyl, hexenyl, heptenyl, octenyl, nonenyl, decenyl, undecenyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cycloheptyl, cyclooctyl, cyclopentenyl, cyclohexenyl, cycloheptenyl, cyclooctenyl, methylcyclopropyl, ethylcyclohexenyl, butenylcyclopentyl, adamantyl, norbornyl and the like. Alkyl substituents are independently selected from the group consisting of hydrogen, deuterium, halogen, —OH, —SH, —NH$_2$, —CN, —NO$_2$, =O, =CH$_2$, trihalomethyl, carbamoyl, arylC$_{0-10}$alkyl, heteroarylC$_{0-10}$alkyl, C$_{1-10}$alkyloxy, arylC$_{0-10}$alkyloxy, C$_{1-10}$alkylthio, arylC$_{0-10}$alkylthio, C$_{1-10}$alkylamino, arylC$_{0-10}$alkylamino, N-aryl-N—C$_{0-10}$alkylamino, C$_{1-10}$alkylcarbonyl, arylC$_{0-10}$alkylcarbonyl, C$_{1-10}$alkylcarboxy, arylC$_{0-10}$alkylcarboxy, C$_{0-10}$alkylcarbonylamino, arylC$_{0-10}$alkylcarbonylamino, tetrahydrofuryl, morpholinyl, piperazinyl, hydroxypyronyl, —C$_{0-10}$alkylCOOR$_{30}$ and —C$_{0-10}$alkylCONR$_{31}$R$_{32}$ wherein R$_{30}$, R$_{31}$ and R$_{32}$ are independently selected from the group consisting of hydrogen, deuterium, alkyl, aryl, or R$_{32}$ and R$_{33}$ are taken together with the nitrogen to which they are attached forming a saturated cyclic or unsaturated cyclic system containing 3 to 8 carbon atoms with at least one substituent as defined herein.

The term "aryl" represents a substituted or unsubstituted, monocyclic, polycyclic, biaryl aromatic groups covalently attached at any ring position capable of forming a stable covalent bond, certain preferred points of attachment being apparent to those skilled in the art (e.g., 3-phenyl, 4-naphthyl and the like). The aryl substituents are independently selected from the group consisting of hydrogen, deuterium, halogen, —OH, —SH, —CN, —NO$_2$, trihalomethyl, hydroxypyronyl, C$_{1-10}$alkyl, arylC$_{0-10}$alkyl, C$_{0-10}$alkyloxyC$_{0-10}$alkyl, arylC$_{0-10}$alkyloxyC$_{0-10}$alkyl, C$_{0-10}$alkylthioC$_{0-10}$alkyl, arylC$_{0-10}$ alkylthioC$_{0-10}$alkyl, C$_{0-10}$alkylaminoC$_{0-10}$alkyl, arylC$_{0-10}$ alkylaminoC$_{0-10}$alkyl, N-aryl-N—C$_{0-10}$alkylaminoC$_{0-10}$ alkyl, C$_{1-10}$alkylcarbonyC$_{0-10}$alkyl, arylC$_{0-10}$ alkylcarbonylC$_{0-10}$alkyl, C$_{1-10}$alkylcarboxyC$_{0-10}$alkyl, arylC$_{0-10}$ alkylcarboxyC$_{0-10}$alkyl, C$_{1-10}$alkylcarbonylaminoC$_{0-10}$ alkyl, arylC$_{0-10}$alkylcarbonylaminoC$_{0-10}$alkyl, —C$_{0-10}$ alkylCOOR$_{30}$, and —C$_{0-10}$alkylCONR$_{31}$R$_{32}$ wherein R$_{30}$, R$_{31}$ and R$_{32}$ are independently selected from the group consisting of hydrogen, deuterium, alkyl, aryl or R$_{31}$ and R$_{32}$ are taken together with the nitrogen to which they are attached forming a saturated cyclic or unsaturated cyclic system containing 3 to 8 carbon atoms with at least one substituent as defined above.

The definition of "aryl" includes but is not limited to phenyl, pentadeuterophenyl, biphenyl, naphthyl, dihydronaphthyl, tetrahydronaphthyl, indenyl, indanyl, azulenyl, anthryl, phenanthryl, fluorenyl, pyrenyl and the like.

Unless otherwise indicated, when a substituent is deemed to be "optionally substituted," it is meant that the substituent is a group that may be substituted with one or more group(s) individually and independently selected from the group consisting of hydrogen, deuterium, alkyl, cycloalkyl, aryl, heteroaryl, heterocyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art examples of which may be found in references such as Greene and Wuts, Protective Groups in Organic Synthesis, 3$^{rd}$ Ed., John Wiley & Sons, New York, N.Y., 1999, which is incorporated by reference herein in its entirety.

The term "prodrug" refers to an agent that is converted into the parent drug in vivo. Prodrugs are often useful because, in some situations, they may be easier to administer than the parent drug.

In light of the purposes described for the present disclosure, all references to "alkyl" and "aryl" groups or any groups ordinarily containing C—H bonds may include partially or fully deuterated versions as required to affect the improvements outlined herein.

Deuterium Kinetic Isotope Effect

In an attempt to eliminate foreign substances, such as therapeutic agents, from its circulation system, the animal body expresses various enzymes, such as the cytochrome P$_{450}$ enzymes or CYPs, esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) π-bond. The resultant metabolites may be stable or unstable under physiological conditions, and can have substantially different phammacokinetic, pharmacodynamic, and acute and long-term toxicity profiles relative to the parent compounds. For most drugs, such oxidations are generally rapid and ultimately lead to administration of multiple or high daily doses.

The relationship between the activation energy and the rate of reaction may be quantified by the Arrhenius equation, $k=Ae^{-E_{act}/RT}$, where $E_{act}$ is the activation energy, T is temperature, R is the molar gas constant, k is the rate constant for the reaction, and A (the frequency factor) is a constant specific to each reaction that depends on the probability that the molecules will collide with the correct orientation. The Arrhenius equation states that the fraction of molecules that have enough energy to overcome an energy barrier, that is, those with energy at least equal to the activation energy, depends exponentially on the ratio of the activation energy to thermal energy (RT), the average amount of thermal energy that molecules possess at a certain temperature.

The transition state in a reaction is a short lived state (on the order of 10$^{-14}$ sec) along the reaction pathway during which the original bonds have stretched to their limit. By definition, the activation energy $E_{act}$ for a reaction is the energy required to reach the transition state of that reaction. Reactions that involve multiple steps will necessarily have a number of transition states, and in these instances, the activation energy for the reaction is equal to the energy difference between the reactants and the most unstable transition state. Once the transition state is reached, the molecules can either revert, thus reforming the original reactants, or new bonds form giving rise to the products. This dichotomy is possible because both pathways, forward and reverse, result in the release of energy. A catalyst facilitates a reaction process by lowering the activation energy leading to a transition state. Enzymes are examples of biological catalysts that reduce the energy necessary to achieve a particular transition state.

A carbon-hydrogen bond is by nature a covalent chemical bond. Such a bond forms when two atoms of similar electronegativity share some of their valence electrons, thereby creating a force that holds the atoms together. This force or bond strength can be quantified and is expressed in units of energy, and as such, covalent bonds between various atoms can be classified according to how much energy must be applied to the bond in order to break the bond or separate the two atoms.

The bond strength is directly proportional to the absolute value of the ground-state vibrational energy of the bond. This vibrational energy, which is also known as the zero-point vibrational energy, depends on the mass of the atoms that form the bond. The absolute value of the zero-point vibrational energy increases as the mass of one or both of the atoms making the bond increases. Since deuterium (D) has twice the mass of hydrogen (H), it follows that a C-D bond is stronger than the corresponding C—H bond. Compounds with C-D bonds are frequently indefinitely stable in $H_2O$, and have been widely used for isotopic studies. If a C—H bond is broken during a rate-determining step in a chemical reaction (i.e. the step with the highest transition state energy), then substituting a deuterium for that hydrogen will cause a decrease in the reaction rate and the process will slow down. This phenomenon is known as the Deuterium Kinetic Isotope Effect (DKIE) and can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small size of a hydrogen atom, and occurs because transition states involving a proton can sometimes form in the absence of the required activation energy. A deuterium is larger and statistically has a much lower probability of undergoing this phenomenon. Substitution of tritium for hydrogen results in yet a stronger bond than deuterium and gives numerically larger isotope effects.

Discovered in 1932 by Urey, deuterium (D) is a stable and non-radioactive isotope of hydrogen. It was the first isotope to be separated from its element in pure form and has twice the mass of hydrogen, and makes up about 0.02% of the total mass of hydrogen (in this usage meaning all hydrogen isotopes) on earth. When two deuterium atoms bond with one oxygen, deuterium oxide ($D_2O$ or "heavy water") is formed. $D_2O$ looks and tastes like $H_2O$, but has different physical properties. It boils at 101.41° C. and freezes at 3.79° C. Its heat capacity, heat of fusion, heat of vaporization, and entropy are all higher than $H_2O$. It is more viscous and has different solubilizing properties than $H_2O$.

When pure $D_2O$ is given to rodents, it is readily absorbed and reaches an equilibrium level that is usually about eighty percent of the concentration that is consumed by the animals. The quantity of deuterium required to induce toxicity is extremely high. When 0% to as much as 15% of the body water has been replaced by $D_2O$, animals are healthy but are unable to gain weight as fast as the control (untreated) group. When about 15% to about 20% of the body water has been replaced with $D_2O$, the animals become excitable. When about 20% to about 25% of the body water has been replaced with $D_2O$, the animals are so excitable that they go into frequent convulsions when stimulated. Skin lesions, ulcers on the paws and muzzles, and necrosis of the tails appear. The animals also become very aggressive; males becoming almost unmanageable. When about 30%, of the body water has been replaced with $D_2O$, the animals refuse to eat and become comatose. Their body weight drops sharply and their metabolic rates drop far below normal, with death occurring at about 30 to about 35% replacement with $D_2O$. The effects are reversible unless more than thirty percent of the previous body weight has been lost due to $D_2O$, Studies have also shown that the use of $D_2O$ can delay the growth of cancer cells and enhance the cytotoxicity of certain antineoplastic agents.

Tritium (T) is a radioactive isotope of hydrogen, used in research, fusion reactors, neutron generators and radiopharmaceuticals. Mixing tritium with a phosphor provides a continuous light source, a technique that is commonly used in wristwatches, compasses, rifle sights and exit signs. It was discovered by Rutherford, Oliphant and Harteck in 1934, and is produced naturally in the upper atmosphere when cosmic rays react with $H_2$ molecules. Tritium is a hydrogen atom that has 2 neutrons in the nucleus and has an atomic weight close to 3. It occurs naturally in the environment in very low concentrations, most commonly found as $T_2O$, a colorless and odorless liquid. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk.

Deuteration of pharmaceuticals to improve pharmacokinetics (PK), pharmacodynamics (PD), and toxicity profiles, has been demonstrated previously with some classes of drugs. For example, DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching which may even give rise to an oxidative intermediate with a faster off-rate from an activating Phase I enzyme (e.g., cytochrome $P_{450}$ 3A4). The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity. Such have not been heretofore sufficiently predictable a priori for any drug class.

Deuterated Zolpidem Derivatives

Certain hypnotic agents are known and are shown herein. Zolpidem (Ambien®) is one such compound. The carbon-hydrogen bonds of zolpidem contain a naturally occurring distribution of hydrogen isotopes, namely $^1H$ or protium (about 99.9844%), $^2H$ or deuterium (about 0.0156%), and $^3H$ or tritium (in the range between about 0.5 and 67 tritium atoms per 1018 protium atoms). Increased levels of deuterium incorporation produce a detectable Kinetic Isotope Effect (KIE) that could affect the pharmacokinetic, pharmacologic and/or toxicologic parameters of such hypnotic agents in comparison to compounds having naturally occurring levels of deuterium.

Aspects of the present disclosure describe an approach to designing and synthesizing new analogs of these hypnotic agents through chemical modifications and derivations of the carbon-hydrogen bonds of the modulators and/or of the chemical precursors used to synthesize these modulators.

Zolpidem contains groups such as the N-methyl groups, the benzyl methyl group, and the imidazopyridyl methyl group known to be sites of cytochrome $P_{450}$ metabolism. The toxicities and pharmacologies of all 12 or more resultant metabolites, however, are not known. Furthermore, because polymorphically expressed CYPs oxidize zolpidem, the prevention of such interactions decreases interpatient variability, decreases drug-drug interactions, increases $T_{1/2}$, decreases the necessary $C_{max}$, and improves several other ADMET parameters. Various deuteration patterns can be used to a) reduce or eliminate unwanted metabolites, b) increase the half-life of the parent drug, c) decrease the number of doses needed to achieve a desired effect, d) decrease the amount of a dose needed to achieve a desired effect, e) increase the formation of active metabolites, if any are formed, and/or f) decrease the production of deleterious metabolites in specific tissues and/or create a more effective drug and/or a safer drug for polypharmacy, whether the polypharmacy be intentional or not. The deuteration approach has strong potential to slow the metabolism through the genetically polymorphically expressed CYPs.

In one aspect, provided herein is a compound of Formula 1:

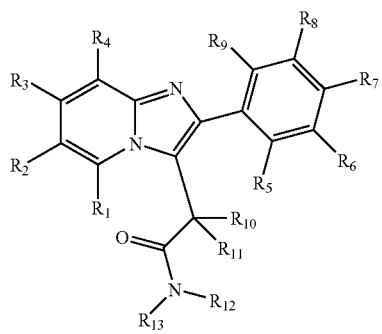

Formula 1 or a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof wherein:

$R_1$, $R_3$, $R_4$, $R_5$, $R_6$, $R_8$, $R_9$, $R_{10}$, and $R_{11}$ are independently selected from the group consisting of hydrogen and deuterium;

$R_2$, $R_7$, $R_{12}$, and $R_{13}$ are independently selected from the group consisting of —$CH_3$, —$CH_2D$, —$CHD_2$, and —$CD_3$; and provided that compounds of Formula 1 contain at least one deuterium atom and that deuterium enrichment in compounds of Formula 1 is at least about 1%.

In one embodiment is a compound selected from the group consisting of:

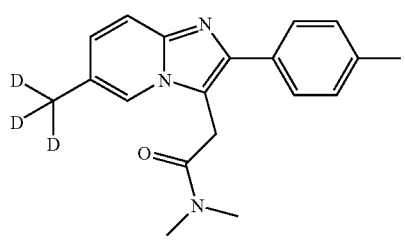

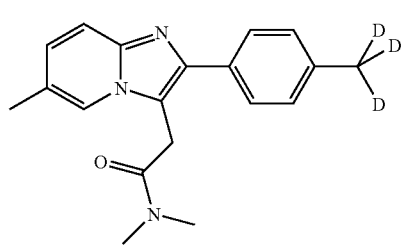

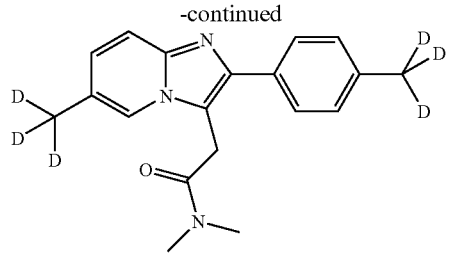

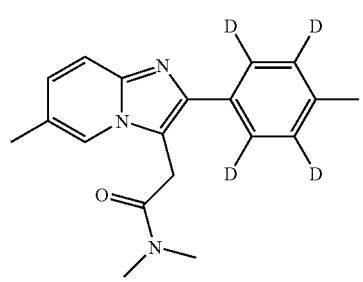

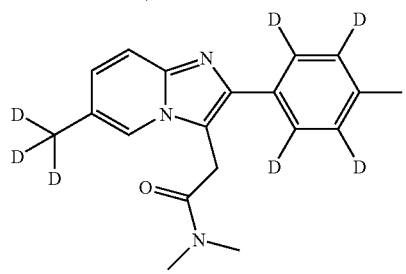

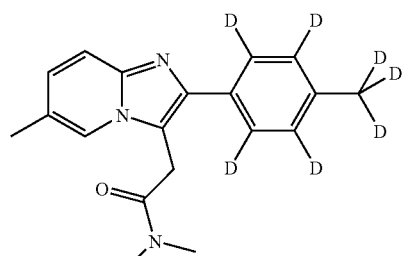

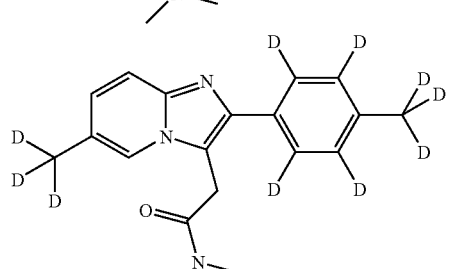

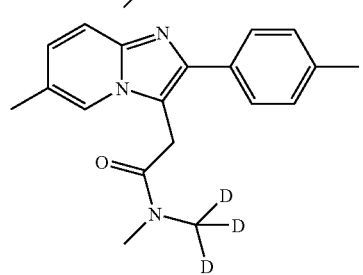

-continued
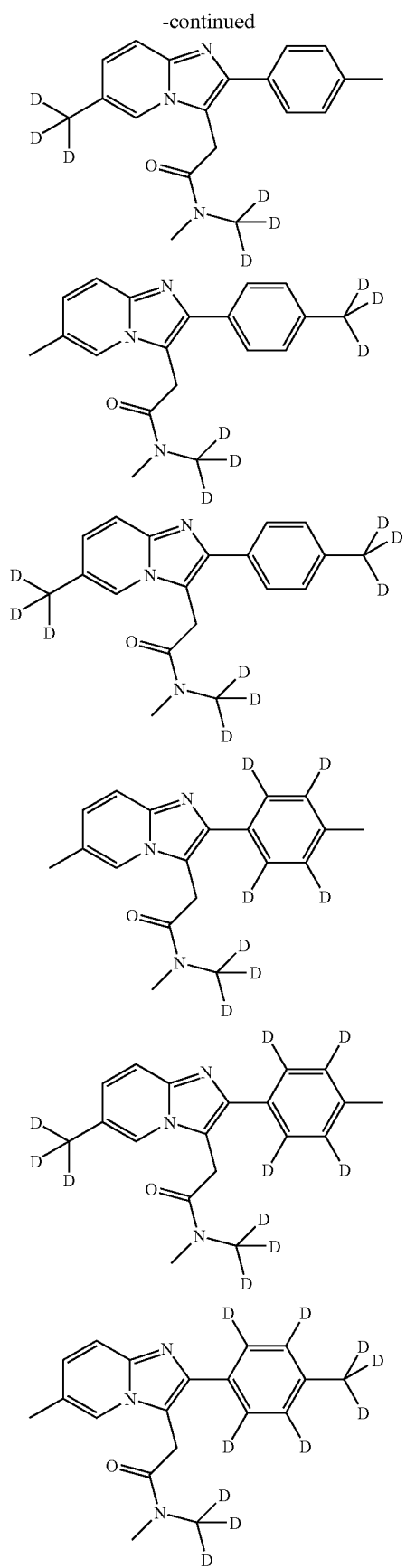
-continued
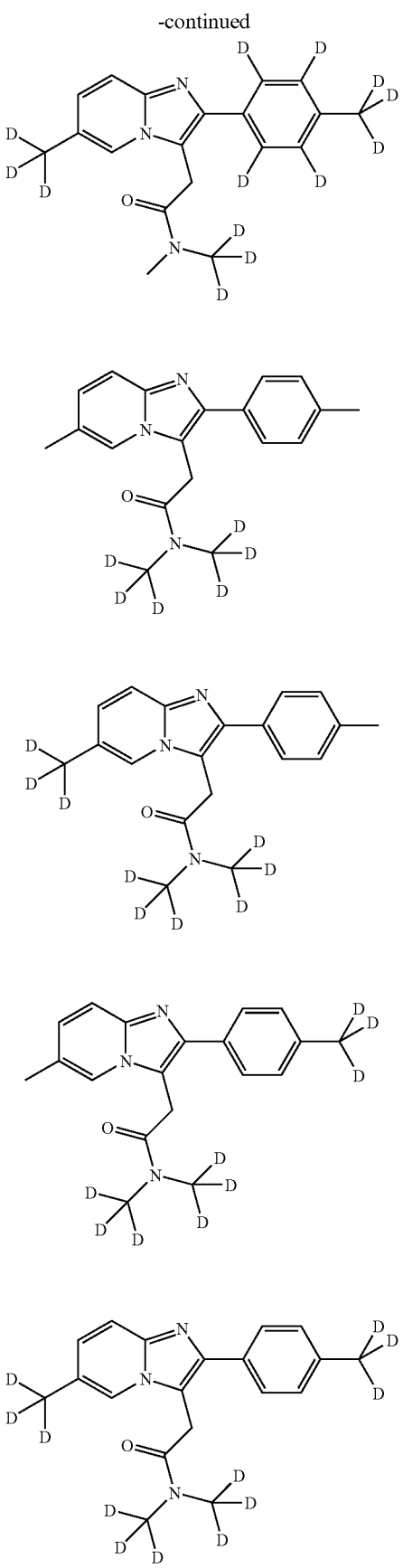

-continued
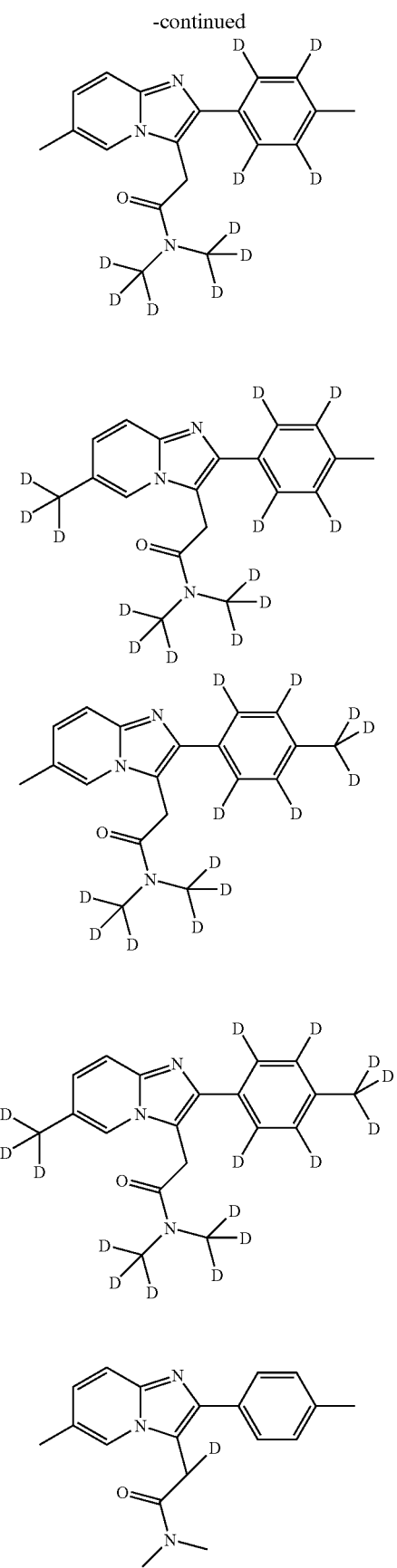
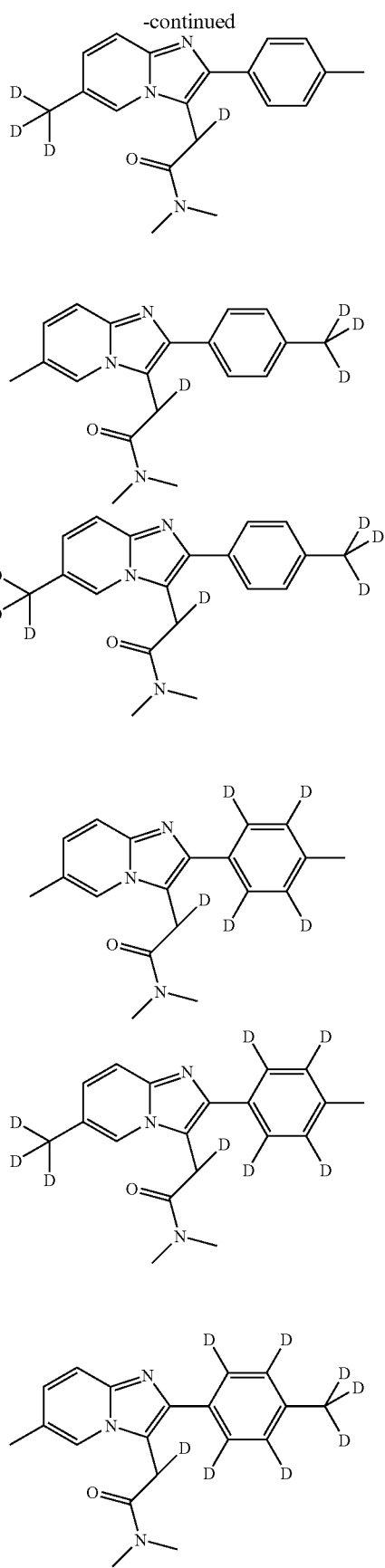

-continued
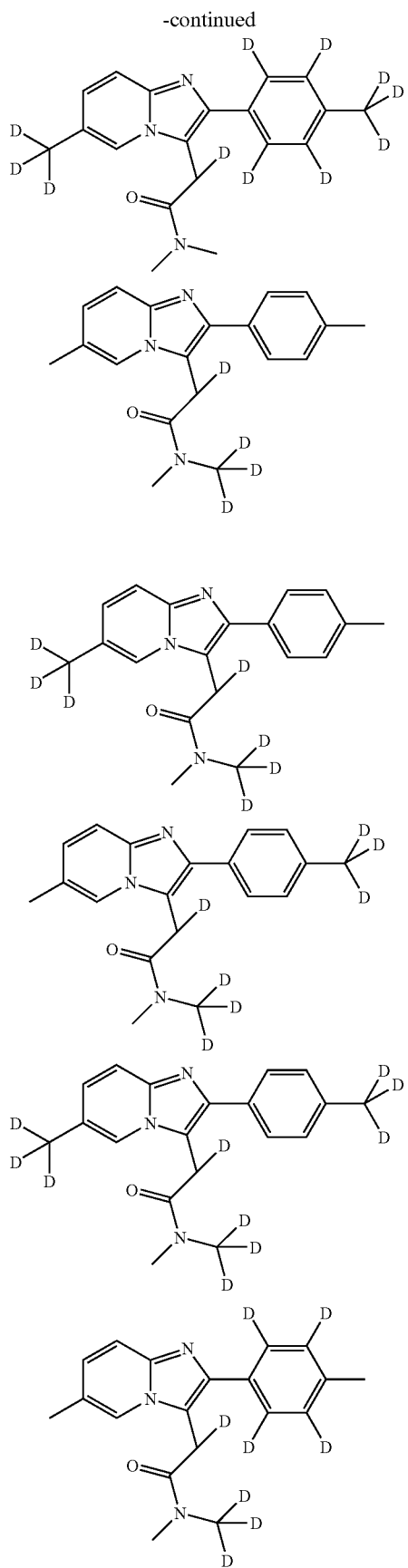
-continued
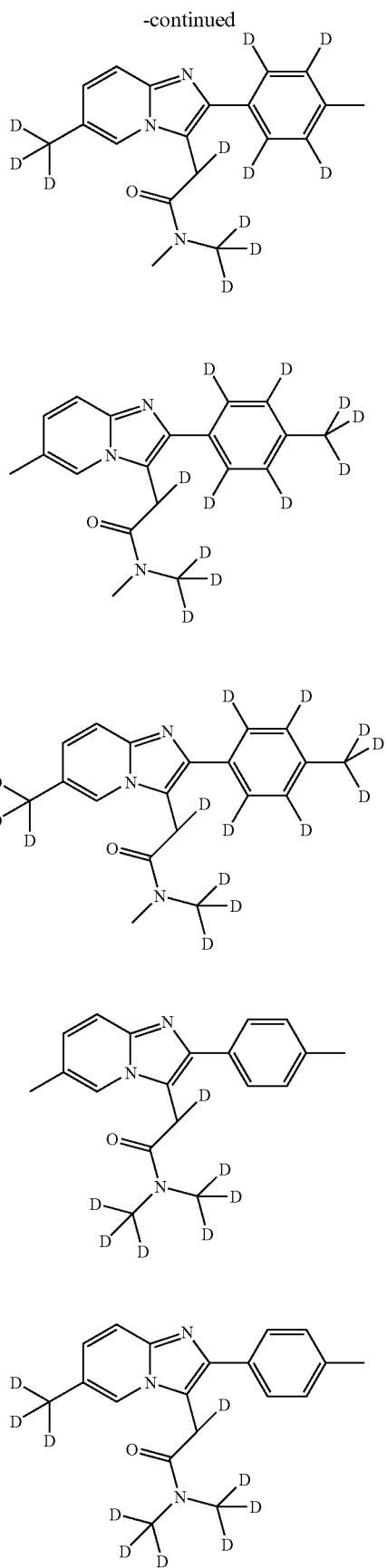

-continued
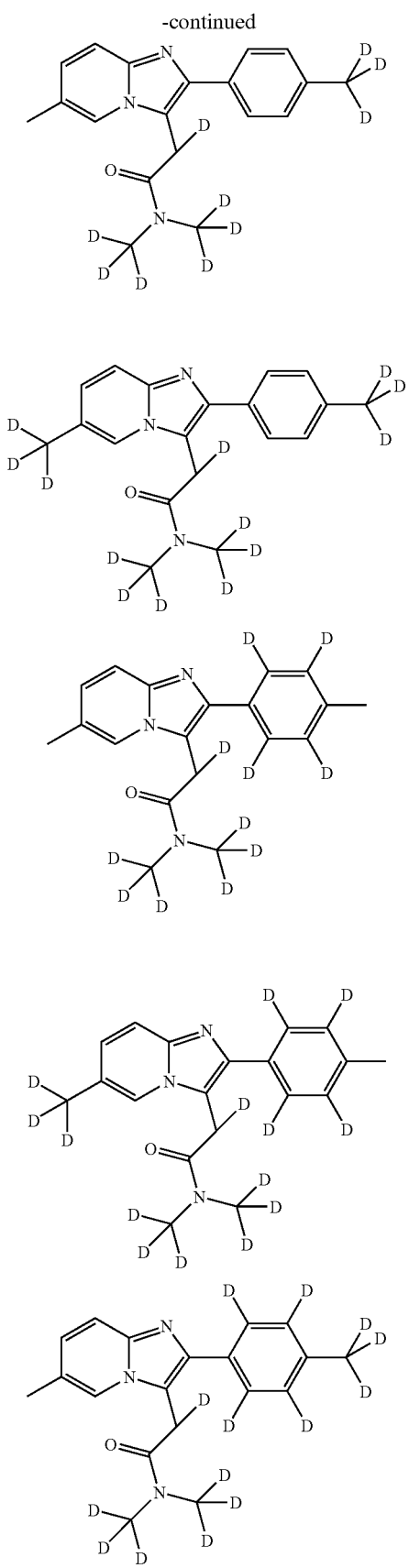
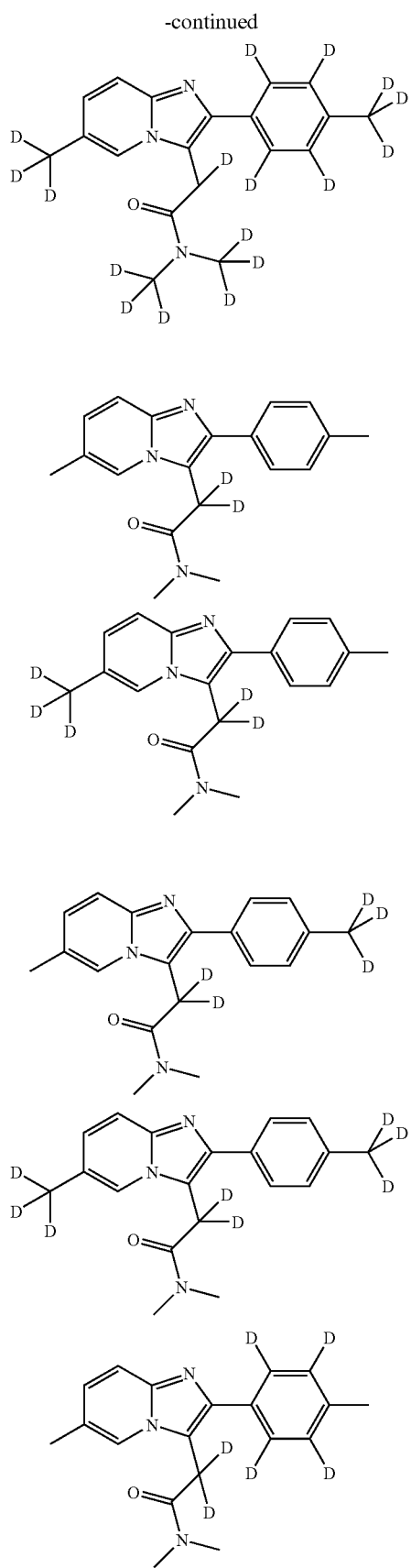

-continued
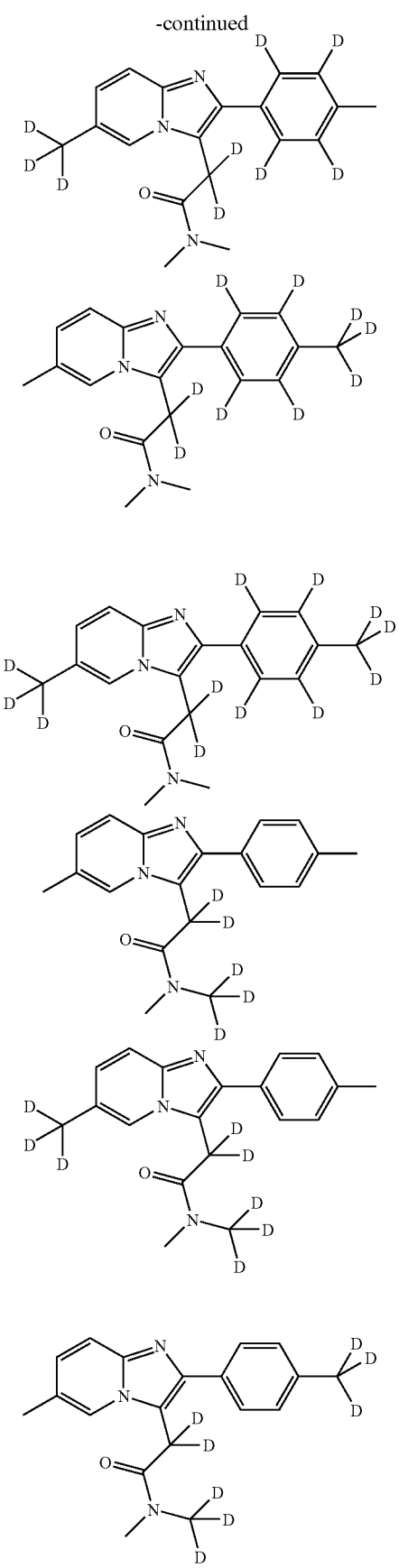
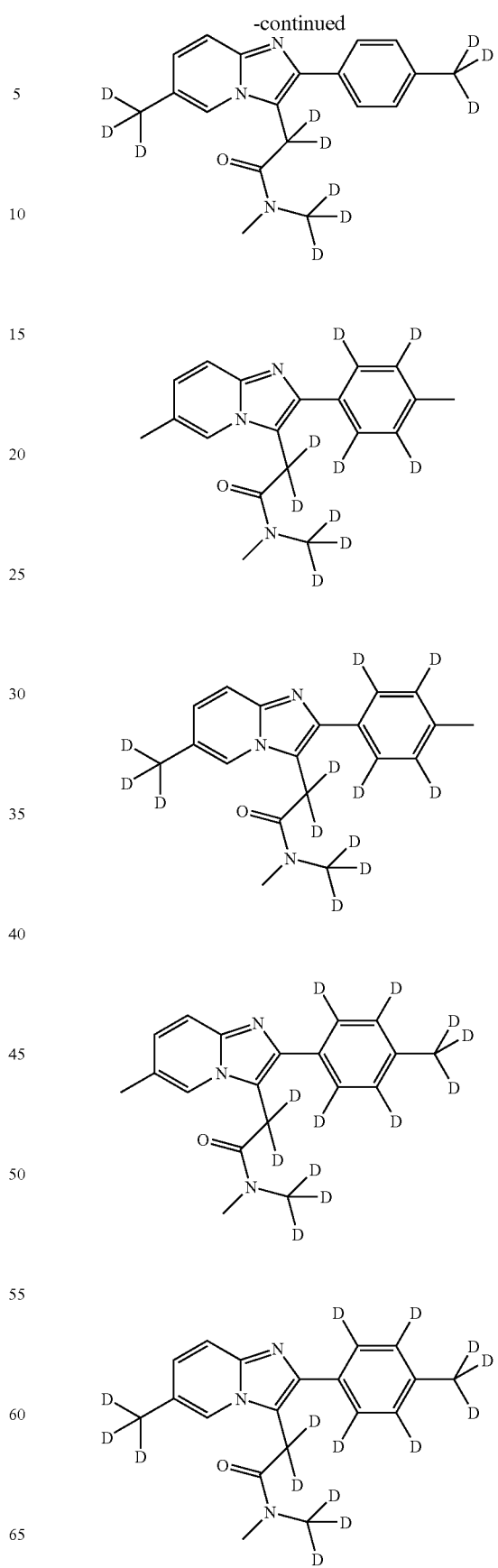

-continued
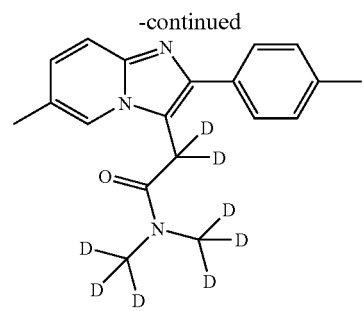
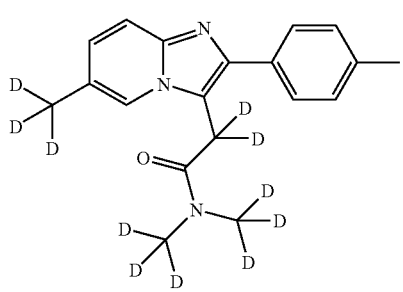
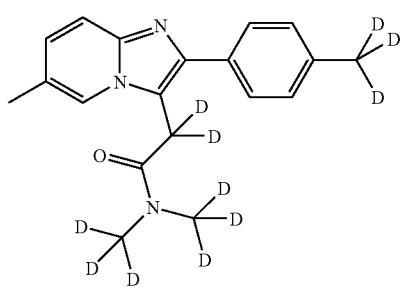
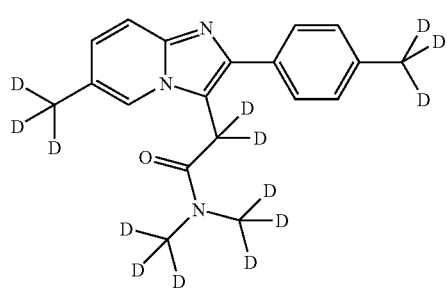
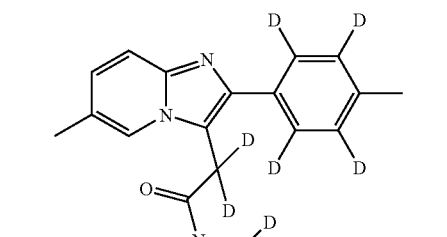
-continued
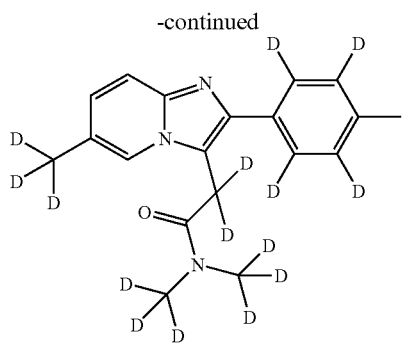
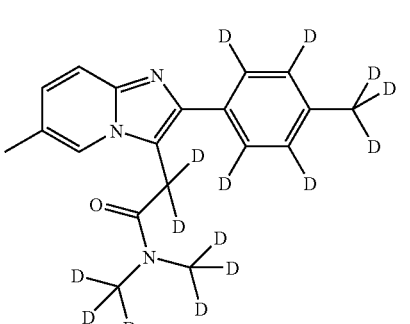
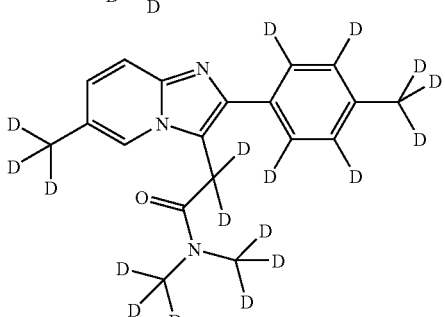
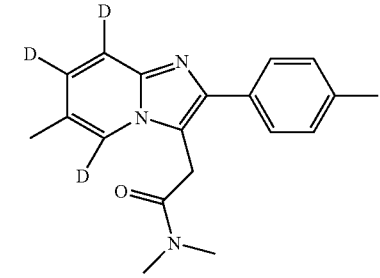
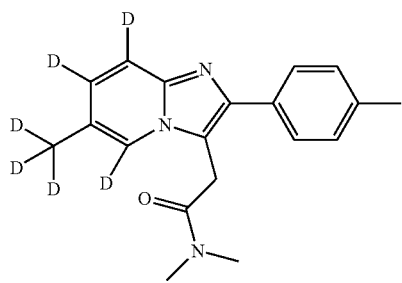

-continued
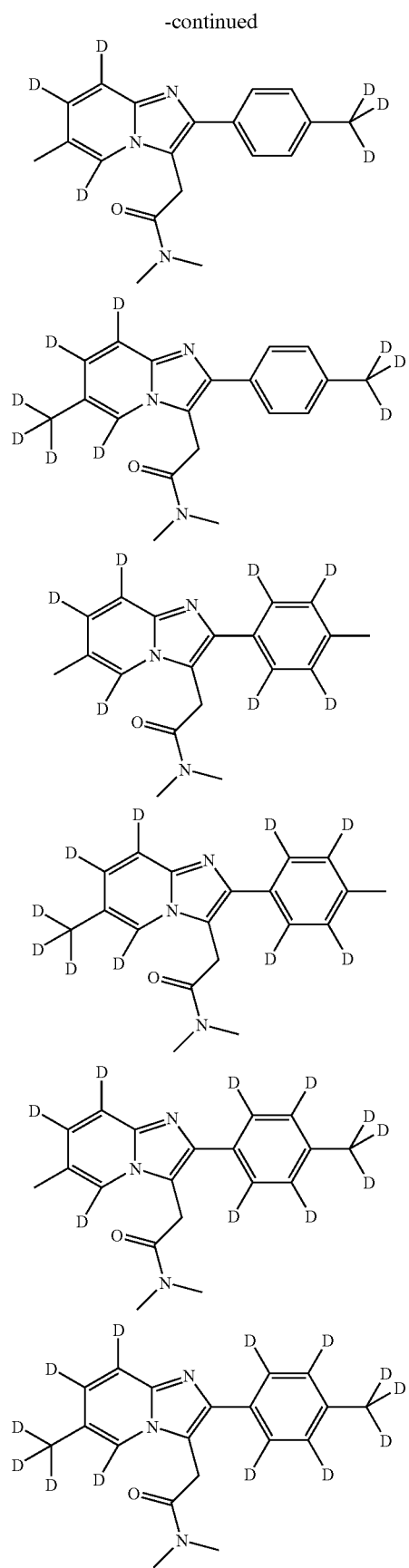
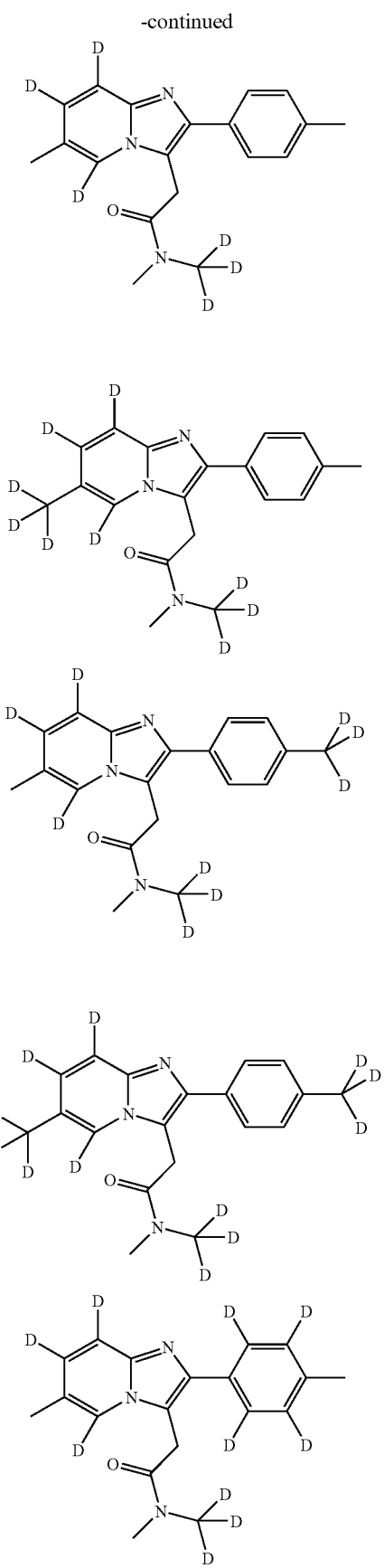

-continued
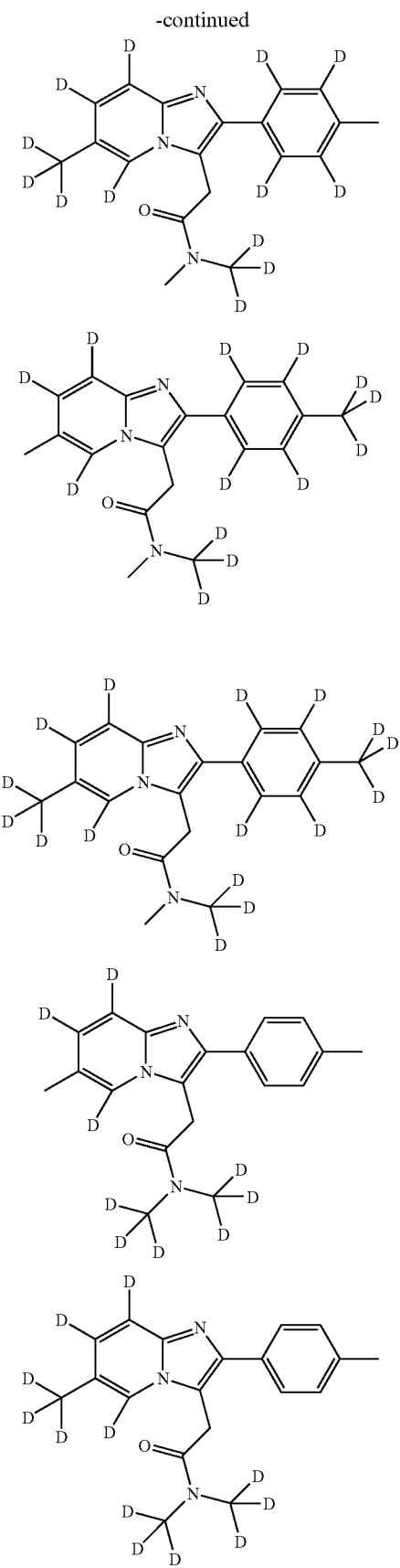
-continued
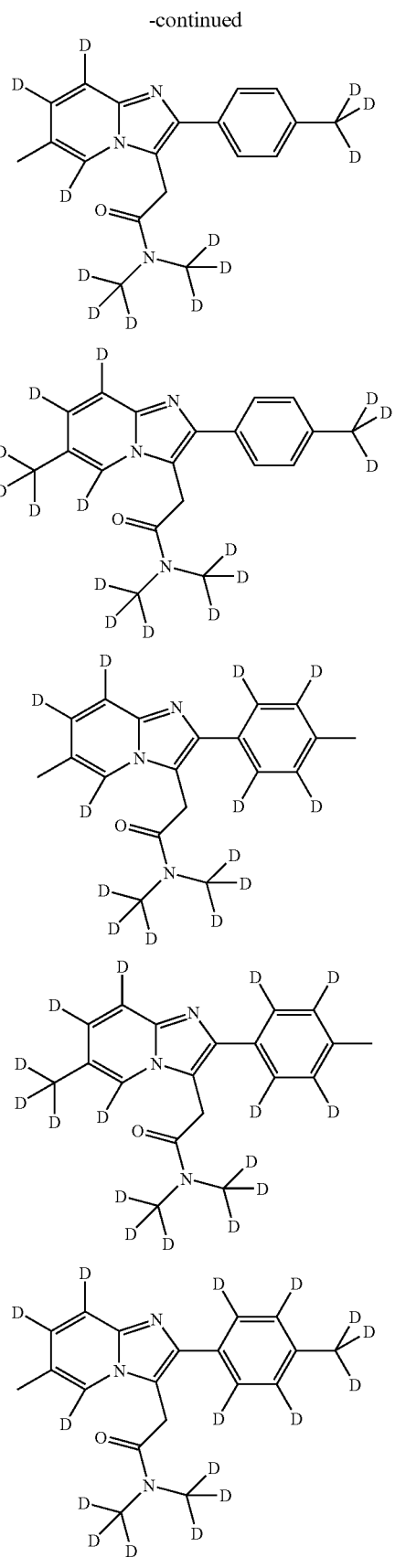

-continued
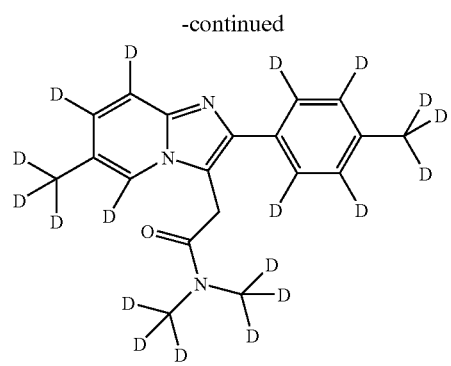
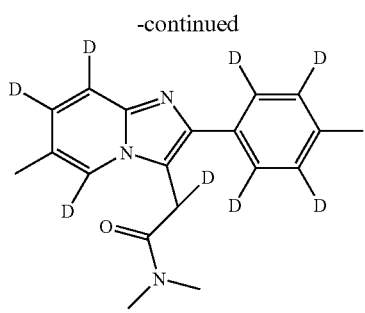
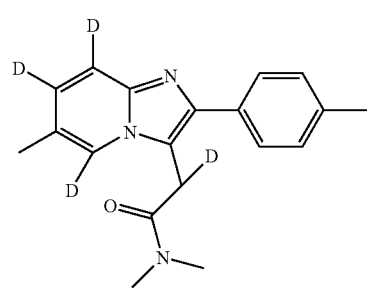
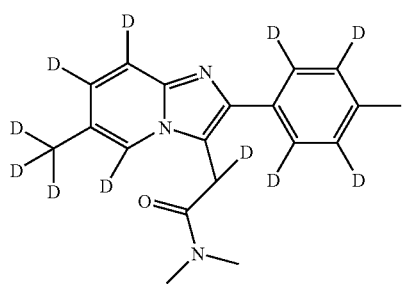
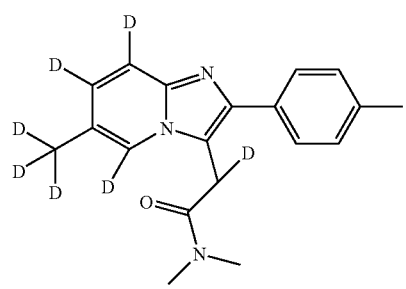
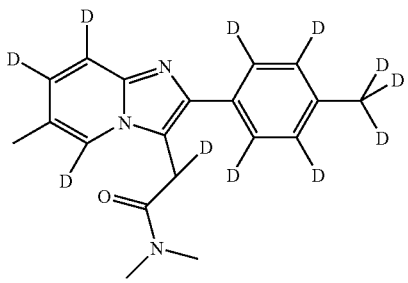
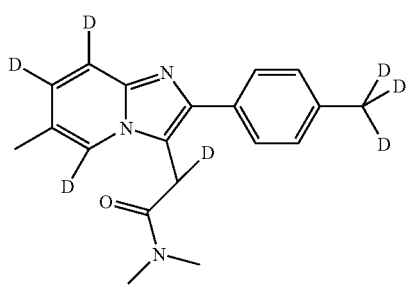
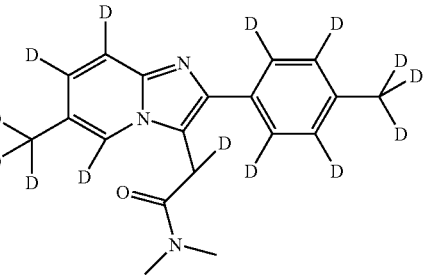
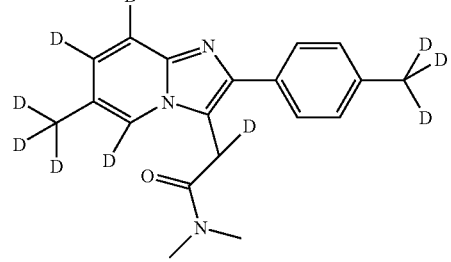
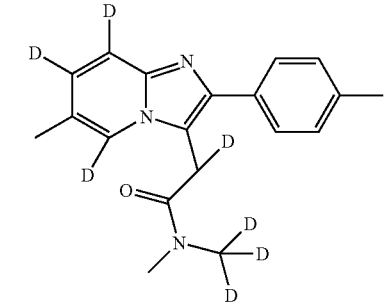

-continued
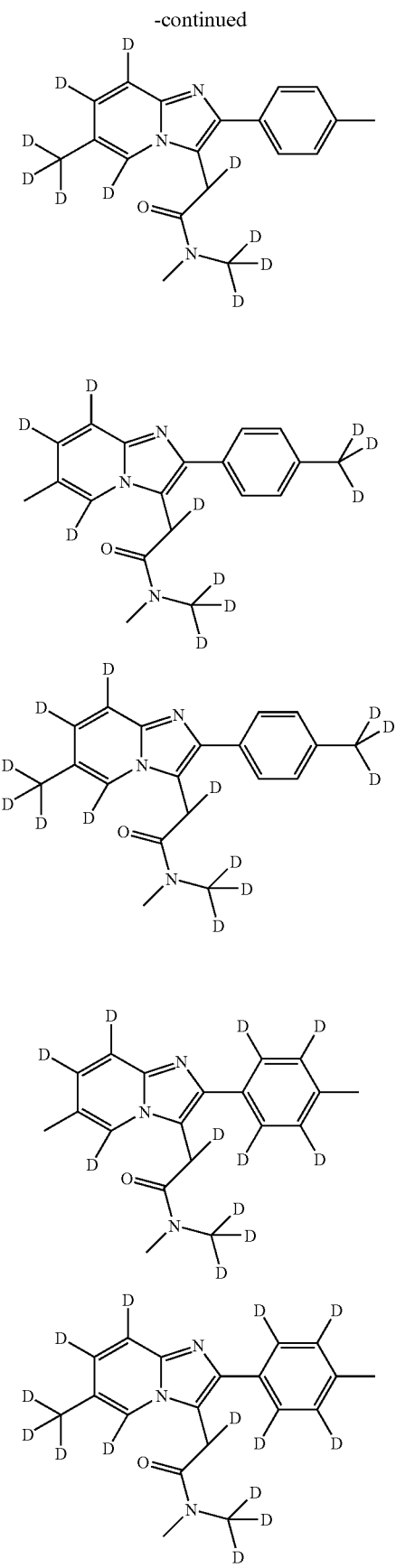
-continued
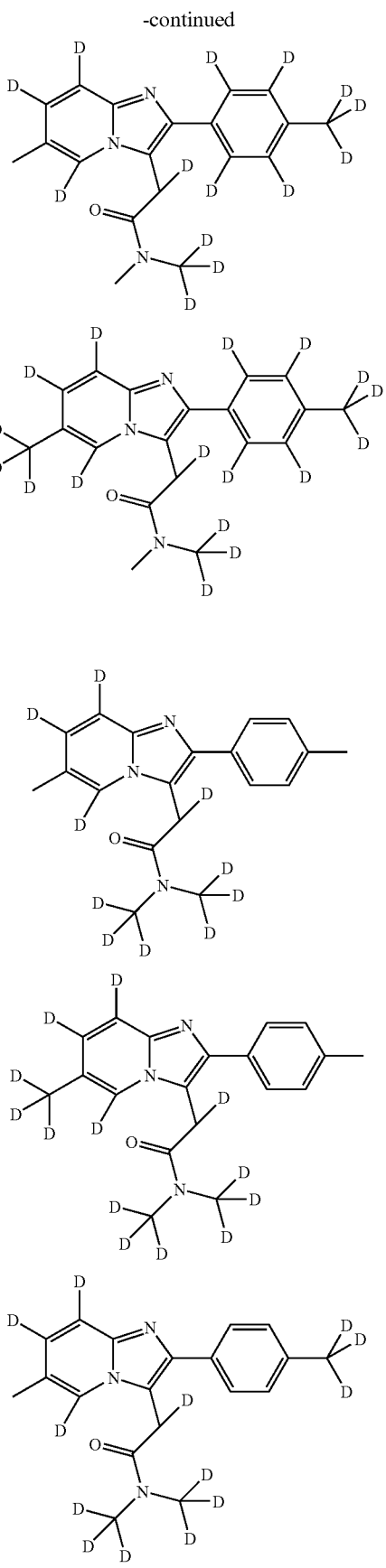

-continued
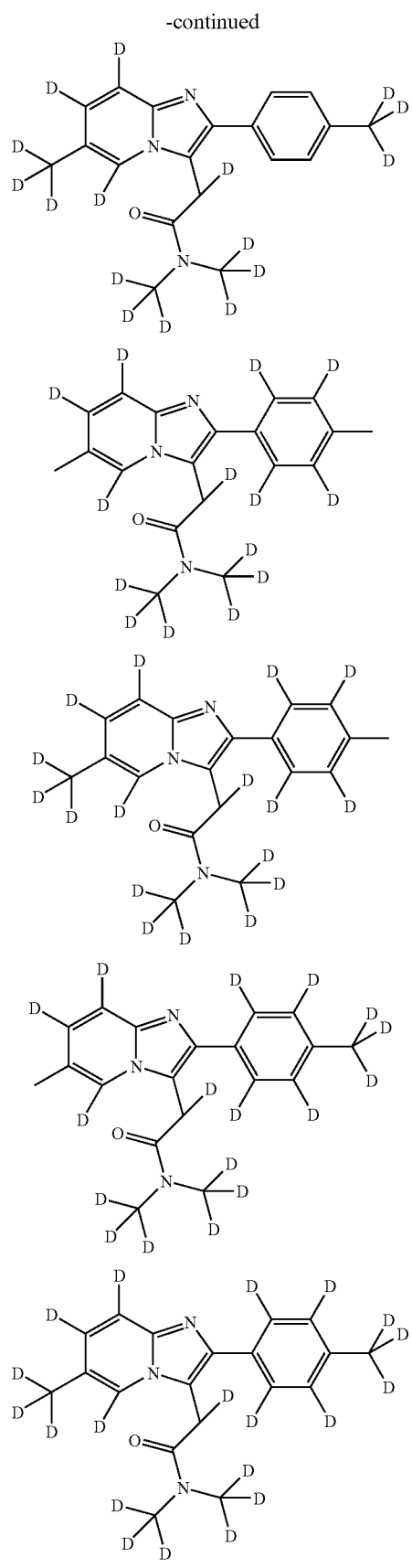
-continued
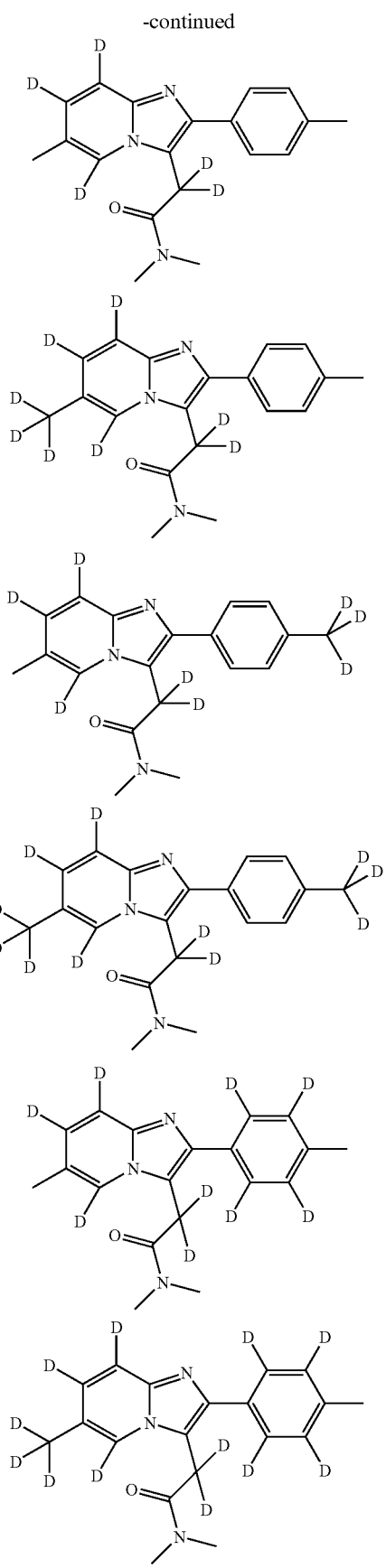

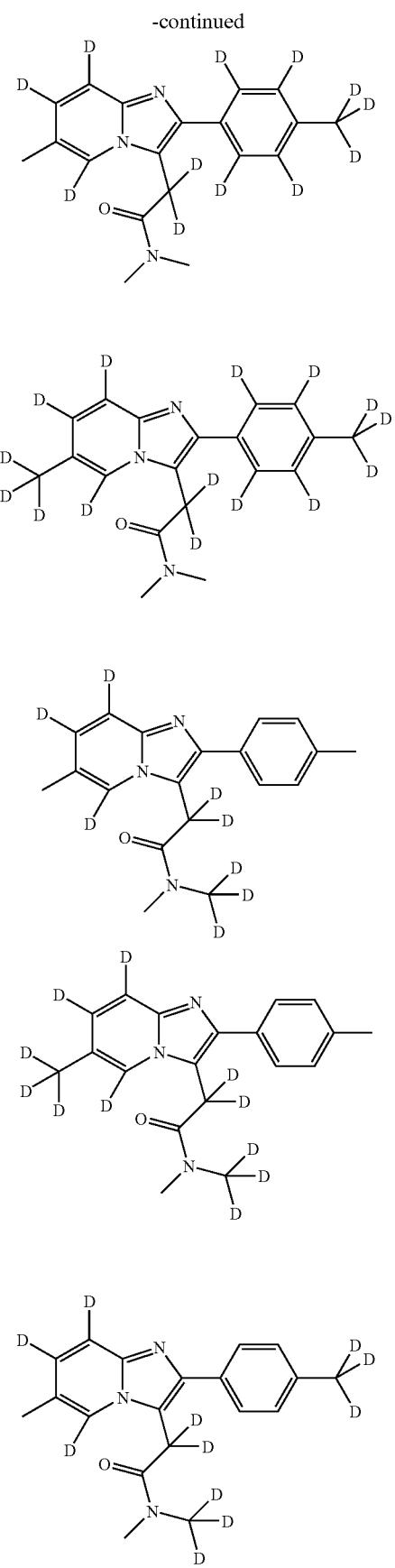
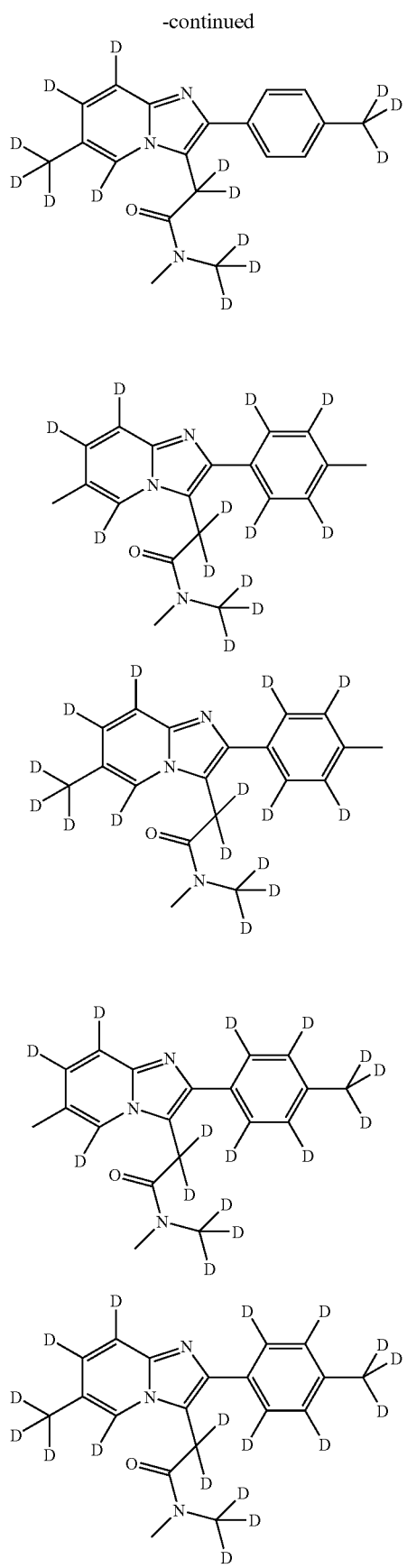

-continued

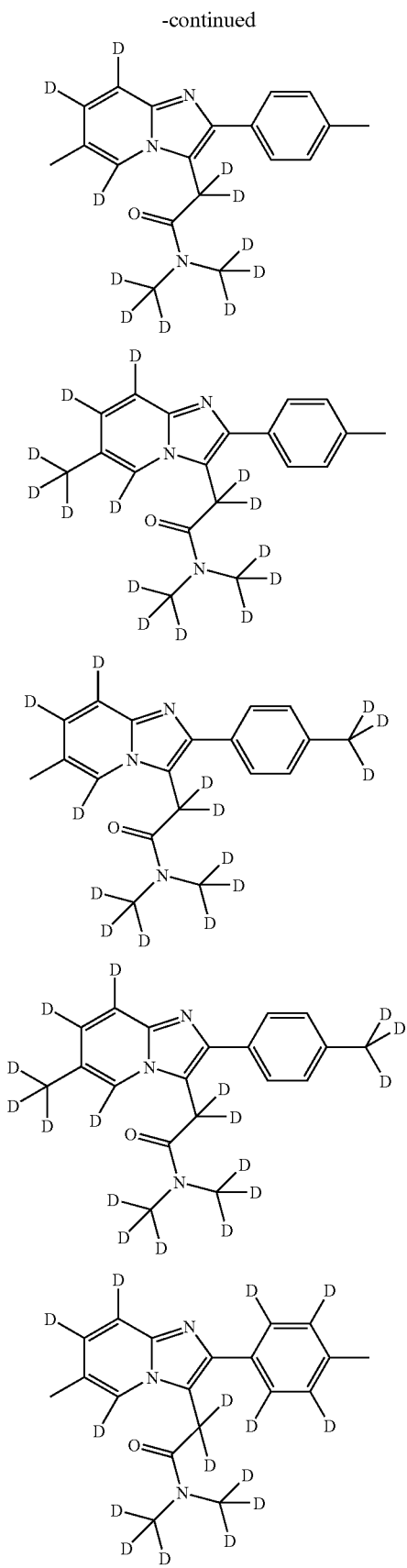

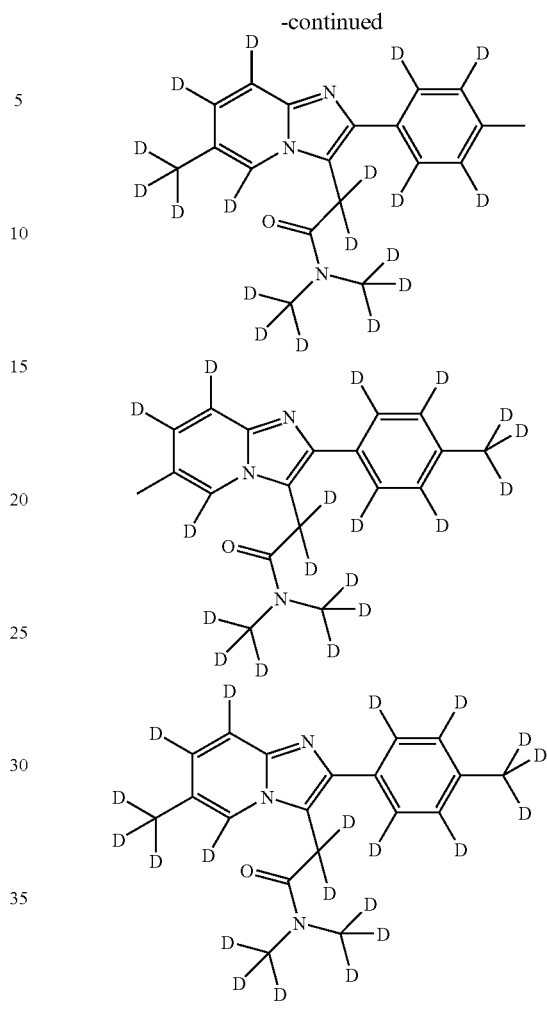

or a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof.

In one embodiment is a compound of Formula 1 wherein the deuterium enrichment is no less than about 1%.

In another embodiment is a compound of Formula 1 wherein the deuterium enrichment is no less than about 10%.

In yet another embodiment is a compound of Formula 1 wherein the deuterium enrichment is no less than about 20%.

In one embodiment is a compound of Formula 1 wherein the deuterium enrichment is no less than about 50%.

In a further embodiment is a compound of Formula 1 wherein the deuterium enrichment is no less than about 70%.

In yet a further embodiment is a compound of Formula 1 wherein the deuterium enrichment is no less than about 80%.

In one embodiment is a compound of Formula 1 wherein the deuterium enrichment is no less than about 90%.

In another embodiment is a compound of Formula 1 wherein the deuterium enrichment is no less than about 95%.

In certain embodiments, $R_1$ is hydrogen. In other embodiments, $R_3$ is hydrogen. In some embodiments, $R_4$ is hydrogen.

In other embodiments, $R_5$ is hydrogen. In yet other embodiments, $R_6$ is hydrogen. In still other embodiments, $R_8$ is hydrogen. In yet other embodiments, $R_9$ is hydrogen. In yet other embodiments, $R_{10}$ is hydrogen. In still other embodiments, $R_{11}$, is hydrogen.

In certain embodiments, $R_1$ is deuterium. In other embodiments, $R_3$ is deuterium. In some embodiments, $R_4$ is deuterium. In other embodiments, $R_5$ is deuterium. In yet other embodiments, $R_6$ is deuterium. In still other embodiments, $R_8$ is deuterium. In yet other embodiments, $R_9$ is deuterium. In yet other embodiments, $R_{10}$ is deuterium. In some embodiments, $R_{11}$ is deuterium.

In certain embodiments, $R_1$ is not hydrogen. In other embodiments, $R_3$ is not hydrogen. In some embodiments, $R_4$ is not hydrogen. In other embodiments, $R_5$ is not hydrogen. In yet other embodiments, $R_6$ is not hydrogen. In still other embodiments, $R_8$ is not hydrogen. In yet other embodiments, $R_9$ is not hydrogen. In yet other embodiments, $R_{10}$ is not hydrogen. In still other embodiments, $R_{11}$ is not hydrogen.

In certain embodiments, $R_1$ is not deuterium. In other embodiments, $R_3$ is not deuterium. In some embodiments, $R_4$ is not deuterium. In other embodiments, $R_5$ is not deuterium. In yet other embodiments, $R_6$ is not deuterium. In still other embodiments, $R_8$ is not deuterium. In yet other embodiments, $R_9$ is not deuterium. In yet other embodiments, $R_{10}$ is not deuterium. In still other embodiments, $R_{11}$ is not deuterium.

In further embodiments, $R_2$ is —$CH_3$. In other embodiments, $R_7$ is —$CH_3$, in some embodiments, $R_{12}$ is —$CH_3$. In yet other embodiments, $R_{13}$ is —$CH_3$.

In further embodiments, $R_2$ is —$CDH_2$. In other embodiments, $R_7$ is —$CDH_2$, in some embodiments, $R_{12}$ is —$CDH_2$. In yet other embodiments, $R_{13}$ is —$CDH_2$.

In further embodiments, $R_2$ is —$CD_2H$. In other embodiments, $R_7$ is —$CD_2H$, in some embodiments, $R_{12}$ is —$CD_2H$. In yet other embodiments, $R_{13}$ is —$CD_2H$.

In further embodiments, $R_2$ is —$CD_3$. In other embodiments, $R_7$ is —$CD_3$, in some embodiments, $R_{12}$ is —$CD_3$. In yet other embodiments, $R_{13}$ is —$CD_3$.

In further embodiments, $R_2$ is not $CH_3$. In other embodiments, $R_7$ is not —$CH_3$, in some embodiments, $R_{12}$ is not —$CH_3$. In yet other embodiments, $R_{13}$ is not —$CH_3$.

In further embodiments, $R_2$ is not $CDH_2$. In other embodiments, $R_7$ is not —$CDH_2$, in some embodiments, $R_{12}$ is not —$CDH_2$. In yet other embodiments, $R_{13}$ is not $CDH_2$.

In further embodiments, $R_2$ is not —$CD_2H$. In other embodiments, $R_7$ is not —$CD_2H$, in some embodiments, $R_{12}$ is not —$CD_2H$. In yet other embodiments, $R_{13}$ is not —$CD_2H$.

In further embodiments, $R_2$ is not —$CD_3$. In other embodiments, $R_7$ is not —$CD_3$, in some embodiments, $R_{12}$ is not —$CD_3$. In yet other embodiments, $R_{13}$ is not —$CD_3$.

In one aspect, are pharmaceutical compositions comprising a compound of Formula 1, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof, and one or more pharmaceutically acceptable excipients or carriers.

In other embodiments, are pharmaceutical compositions comprising a compound of Formula 1, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof, and one or more pharmaceutically acceptable excipients or carriers for the treatment of conditions involving hypnosis.

In other embodiments, are pharmaceutical compositions comprising a compound of Formula 1, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof, and one or more pharmaceutically acceptable excipients or carriers for the treatment of conditions related to sleep.

In another aspect, is a method of modulating a benzodiazepine receptor, comprising administering a compound of Formula 1 or the (−)-enantiomer of the compound of Formula 1, or the (+)-enantiomer of the compound of Formula 1.

In one aspect is a method of treating a mammalian subject, having, suspected of having, or being prone to a disease or condition involving a benzodiazepine receptor, comprising administering to a mammalian subject in need thereof a therapeutically effective amount of a compound of Formula 1, or a pharmaceutically acceptable salt, solvate, or prodrug thereof.

In certain embodiments, the compound of Formula 1 contains about 60% or more by weight of the (−)-enantiomer of the compound and about 40% or less by weight of (+)-enantiomer of the compound. In other embodiments, the compound of Formula 1 contains about 70% or more by weight of the (−)-enantiomer of the compound and about 30% or less by weight of (+)-enantiomer of the compound. In certain embodiments, the compound of Formula 1 contains about 80% or more by weight of the (−)-enantiomer of the compound and about 20% or less by weight of (+)-enantiomer of the compound. In some embodiments, the compound of Formula 1 contains about 90% or more by weight of the (−)-enantiomer of the compound and about 10% or less by weight of the (+)-enantiomer of the compound. In other embodiments, the compound of Formula 1 contains about 95% or more by weight of the (−)-enantiomer of the compound and about 5% or less by weight of (+)-enantiomer of the compound. In certain embodiments, the compound of Formula 1 contains about 99% or more by weight of the (−)-enantiomer of the compound and about 1% or less by weight of (+)-enantiomer of the compound.

In certain embodiments, the compound of Formula 1 contains about 60% or more by weight of the (+)-enantiomer of the compound and about 40% or less by weight of (−)-enantiomer of the compound. In other embodiments, the compound of Formula 1 contains about 70% or more by weight of the (+)-enantiomer of the compound and about 30% or less by weight of (−)-enantiomer of the compound. In certain embodiments, the compound of Formula 1 contains about 80% or more by weight of the (+)-enantiomer of the compound and about 20% or less by weight of (−)-enantiomer of the compound. In some embodiments, the compound of Formula 1 contains about 90% or more by weight of the (+)-enantiomer of the compound and about 10% or less by weight of the (−)-enantiomer of the compound. In other embodiments, the compound of Formula 1 contains about 95% or more by weight of the (+)-enantiomer of the compound and about 5% or less by weight of (−)-enantiomer of the compound. In certain embodiments, the compound of Formula 1 contains about 99% or more by weight of the (+)-enantiomer of the compound and about 1% or less by weight of (−)-enantiomer of the compound.

The deuterated compound of Formula 1 may also contain less prevalent isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen.

In certain embodiments, without being bound by any theory, the compound provided herein may expose a patient to a maximum of about 0.000005% $D_2O$ or about 0.00001% DHO, assuming that all of the C-D bonds in the compound of Formula 1 are metabolized and released as $D_2O$ or DHO. This quantity is a small fraction of the naturally occurring background levels of $D_2O$ or DHO in circulation. In certain embodiments, the levels of $D_2O$ shown to cause toxicity in animals is much greater than even the maximum limit of exposure because of the deuterium enriched compound of Formula 1. Thus, in certain embodiments, the deuterium-enriched compound provided herein should not cause any additional toxicity because of the use of deuterium.

In one embodiment, the deuterated compounds provided herein maintain the beneficial aspects of the corresponding non-isotopically enriched molecules while substantially increasing the maximum tolerated dose, decreasing toxicity, increasing the half-life ($T_{1/2}$), lowering the maximum plasma concentration ($C_{max}$) of the minimum efficacious dose (MED), lowering the efficacious dose and thus decreasing the non-mechanism-related toxicity, and/or lowering the probability of drug-drug interactions.

Isotopic hydrogen can be introduced into a compound of Formula 1 as provided herein by synthetic techniques that employ deuterated reagents, whereby incorporation rates are pre-determined; and/or by exchange techniques, wherein incorporation rates are determined by equilibrium conditions, and may be highly variable depending on the reaction conditions. Synthetic techniques, where tritium or deuterium is directly and specifically inserted by tritiated or deuterated reagents of known isotopic content, may yield high tritium or deuterium abundance, but can be limited by the chemistry required. In addition, the molecule being labeled may be changed, depending upon the severity of the synthetic reaction employed. Exchange techniques, on the other hand, may yield lower tritium or deuterium incorporation, often with the isotope being distributed over many sites on the molecule, but offer the advantage that they do not require separate synthetic steps and are less likely to disrupt the structure of the molecule being labeled.

The compounds of Formula 1 as provided herein can be prepared by methods known to one of skill in the art or following procedures similar to those described in the Example section herein and routine modifications thereof. For an example, the compound of Formula 1 can be prepared as shown in Scheme 1.

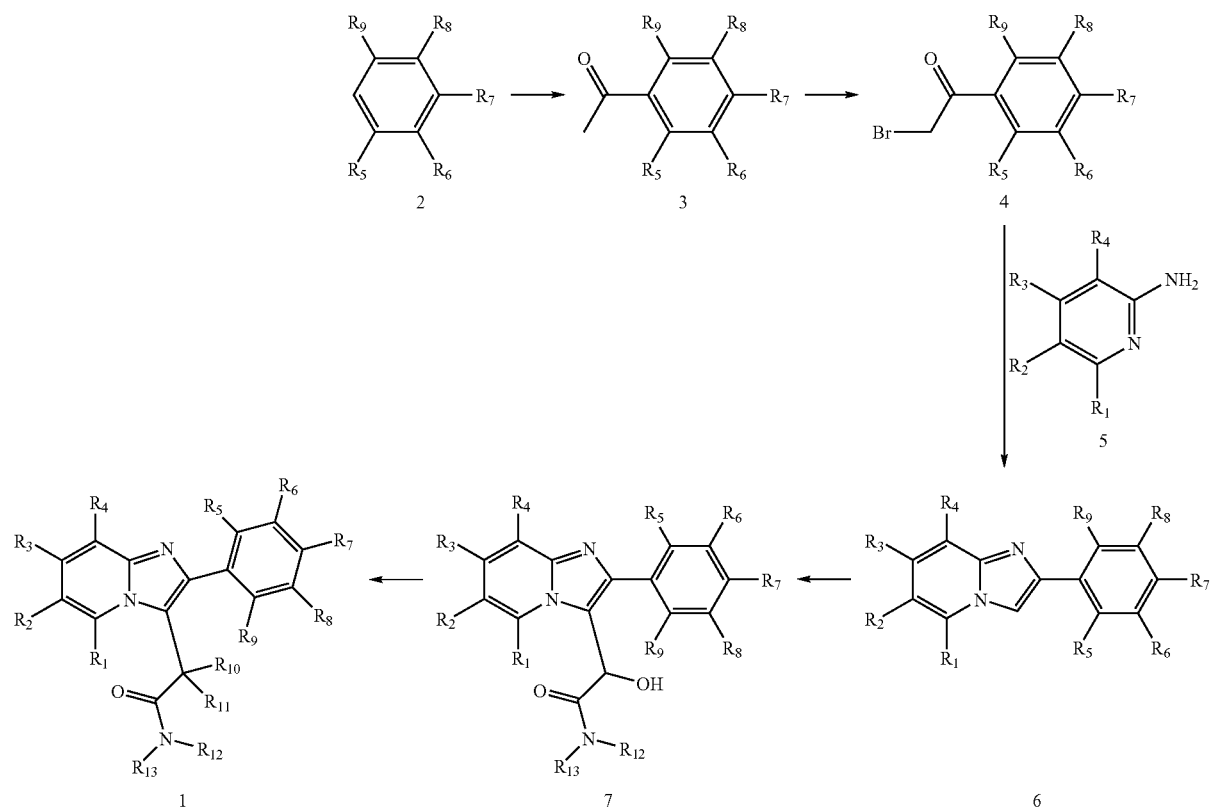

Toluene 2 is treated with acetic anhydride and aluminum trichloride at an elevated temperature to give ketone 3, which reacts with tetrabutylammonium tribromide to give bromoketone 4. Compound 4 is coupled with aminopyridine 5 at an elevated temperature to give imidazopyridine 6. Treatment of compound 6 with N,N-dimethyl-2-oxo-acetamide hemihydrate at an elevated temperature affords amide 7, which is reacted with phosphorus tribromide at an elevated temperature to produce the compound of Formula 1.

Deuterium can be incorporated to different positions synthetically, according to the synthetic procedures as shown in Scheme 1, by using appropriate deuterated intermediates. For example, to introduce deuterium at one or more positions selected from $R_1$, $R_2$, $R_3$, and $R_4$ aminopyridine 5 with the corresponding deuterium substitutions can be used. To introduce deuterium at one or more positions selected from $R_5$, $R_6$, $R_7$, $R_9$, and $R_9$, toluene 2 with the corresponding deuterium substitutions can be used. To introduce deuterium at one or more positions of $R_{12}$ and $R_{13}$, N,N-dimethyl-2-oxo-acetamide hemihydrate with the corresponding deuterium substitutions can be used. These deuterated intermediates are either commercially available, or can be prepared by methods known to one of skill in the art or following procedures similar to those described in the Example section herein and routine modifications thereof.

Deuterium can also be incorporated to various positions having an exchangeable proton, such as the alpha position to the cabonyl, via proton-deuterium equilibrium exchange. To introduce deuterium at $R_{10}$ and $R_{11}$, these protons may be replaced with deuterium selectively or non-selectively through a proton-deuterium exchange method known in the art.

It is to be understood that the compounds provided herein may contain one or more chiral centers, chiral axes, and/or chiral planes, as described in "Stereochemistry of Carbon Compounds" Eliel and Wilen, John Wiley & Sons, New York, 1994, pp. 1119-1190. Such chiral centers, chiral axes, and chiral planes may be of either the (R) or (S) configuration, or may be a mixture thereof.

Another method for characterizing a composition containing a compound having at least one chiral center is by the effect of the composition on a beam of polarized light. When a beam of plane polarized light is passed through a solution of a chiral compound, the plane of polarization of the light that emerges is rotated relative to the original plane. This phenomenon is known as optical activity, and compounds that rotate the plane of polarized light are said to be optically active. One enantiomer of a compound will rotate the beam of polarized light in one direction, and the other enantiomer will rotate the beam of light in the opposite direction. The enantiomer that rotates the polarized light in the clockwise direction is the (+)-enantiomer, and the enantiomer that rotates the polarized light in the counterclockwise direction is the (−)-enantiomer. Included within the scope of the compositions described herein are compositions containing between 0 and 100% of the (+) and/or (−)-enantiomer of compounds of Formula 1.

Where a compound of Formula 1 contains an alkenyl or alkenylene group, the compound may exist as one or mixture of geometric cis/trans (or Z/E) isomers. Where structural isomers are interconvertible via a low energy barrier, the compound of Formula 1 may exist as a single tautomer or a mixture of tautomers. This can take the form of proton tautomerism in the compound of Formula 1 that contains for example, an imino, keto, or oxime group; or so-called valence tautomerism in the compound that contain an aromatic moiety. It follows that a single compound may exhibit more than one type of isomerism.

The compounds provided herein may be enantiomerically pure, such as a single enantiomer or a single diastereomer, or be stereoisomeric mixtures, such as a mixture of enantiomers, a racemic mixture, or a diastereomeric mixture. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include chiral synthesis from a suitable optically pure precursor or resolution of the racemate using, for example, chiral chromatography, recrystallization, resolution, diastereomeric salt formation, or derivatization into diastereomeric adducts followed by separation.

When the compound of Formula 1 contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stah and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lacetic acid, (±)-DL-lacetic acid, lactobionic acid, lauric acid, maleic acid, (−)-L-malic acid, malonic acid, (+)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound of Formula 1 may also be provided as a prodrug, which is a functional derivative of the compound of Formula 1 and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; Waller et al., *Br. J. Clin. Pharmac.* 1989, 28, 497-507.

Pharmaceutical Compositions

Provided herein are pharmaceutical compositions comprising a compound of Formula 1 as an active ingredient, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof, in a pharmaceutically acceptable vehicle, carrier, diluent, or excipient, or a mixture thereof; and one or more pharmaceutically acceptable excipients or carriers.

Also provided herein are pharmaceutical compositions in modified release dosage forms, which comprise a compound of Formula 1, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof; and one or more release controlling excipients as described herein. Suitable modified release dosage vehicles include, but are not limited to, hydrophilic or hydrophobic matrix devices, water-soluble separating layer coatings, enteric coatings, osmotic devices, multi-particulate devices, and combinations thereof. The pharmaceutical compositions may also comprise non-release controlling excipients.

Further, provided herein are pharmaceutical compositions in enteric coated dosage forms, which comprise a compound of Formula 1, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof; and one or more release controlling excipients for use in an enteric coated dosage form. The pharmaceutical compositions may also comprise non-release controlling excipients.

Additionally, provided herein are pharmaceutical compositions in effervescent dosage forms, which comprise the compounds of Formula 1, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof; and one or more release controlling excipients for use in an enteric coated dosage form. The pharmaceutical compositions may also comprise non-release controlling excipients.

Further, provided herein are pharmaceutical compositions in a dosage form that has an instant releasing component and at least one delayed releasing component, and is capable of giving a discontinuous release of the compound in the form of at least two consecutive pulses separated in time from 0.1 up to 24 hours. The pharmaceutical compositions comprise a compound of Formula 1, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof; and one or more release controlling and non-release controlling excipients, such as those excipients suitable for a disruptable semi-permeable membrane and as swellable substances.

Provided herein also are pharmaceutical compositions in a dosage form for oral administration to a subject, which comprises a compound of Formula 1, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof; and one or more pharmaceutically acceptable excipients or carriers, enclosed in an intermediate reactive layer comprising a gastric juice-resistant polymeric layered material partially neutralized with alkali and having cation exchange capacity and a gastric juice-resistant outer layer.

Provided herein are pharmaceutical compositions that comprise about 0.1 to about 100 mg, about 0.5 to about 50 mg, about 1 to about 20 mg, about 1 mg, about 2 mg, about 3 mg, about 4 mg, about 5 mg, about 6 mg, about 7 mg, about 8 mg, about 10 mg, about 15 mg, about 20 mg of one or more compounds of Formula I in the form of tablets for oral administration. The pharmaceutical compositions further comprise hydroxypropyl methylcellulose, lactose, magnesium stearate, micro-crystalline cellulose, polyethylene glycol, sodium starch glycolate, titanium dioxide, and polysorbate 80.

Provided herein are pharmaceutical compositions that comprise about 0.1 to about 100 mg, about 0.5 to about 50 mg, about 1 to about 20 mg, about 1 mg, about 2 mg, about 3 mg, about 4 mg, about 5 mg, about 6 mg, about 7 mg, about 8 mg, about 10 mg, about 15 mg, about 20 mg of one or more compounds of Formula I in the form of coated two-layer tablet for oral administration: one layer that releases a compound of Formula 1 immediately and another layer that allows a slower release of additional compound of Formula 1. The pharmaceutical compositions further comprise colloidal silicon dioxide, hypromellose, lactose monohydrate, magnesium stearate, microcrystalline cellulose, polyethylene glycol, potassium bitartrate, sodium starch glycolate, and titanium dioxide.

The pharmaceutical compositions provided herein may be provided in unit-dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include ampules, syringes, and individually packaged tablets and capsules. Unit-dosage forms may be administered in fractions or multiples thereof. A multiple-dosage form is a plurality of identical unit-dosage forms packaged in a single container to be administered in segregated unit-dosage form. Examples of multiple-dosage forms include vials, bottles of tablets or capsules, or bottles of pints or gallons.

The compound of Formula 1 provided herein may be administered alone, or in combination with one or more other compounds provided herein, one or more other active ingredients. The pharmaceutical compositions that comprise a compound provided herein may be formulated in various dosage forms for oral, parenteral, and topical administration. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, Remington: The Science and Practice of Pharmacy, supra; Modified-Release Drug Deliver Technology, Rathbone et al., Eds., Drugs and the Pharmaceutical Science, Marcel Dekker, Inc.: New York, N.Y., 2002; Vol. 126).

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

A. Oral Administration

The pharmaceutical compositions provided herein may be provided in solid, semisolid, or liquid dosage forms for oral administration. As used herein, oral administration also include buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL®200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems. Micellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action, such as other $GABA_A$ receptor modulators.

B. Parenteral Administration

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide.

Suitable antimicrobial agents or preservatives include, but are not limited to, phenols, cresols, mercurials, benzyl alcohol, chlorobutanol, methyl and propyl p-hydroxybenzates, thimerosal, benzalkonium chloride, benzethonium chloride, methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lacetic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein may be formulated for single or multiple dosage administration. The single dosage formulations are packaged in an ampule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed-, sustained, pulsed-, controlled, targeted-, and programmed-release forms.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers, such as hydrogels of esters of acrylic and methacrylic acid, collagen, cross-linked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein may be administered topically to the skin, orifices, or mucosa. The topical administration, as used herein, include (intra)dermal, conjuctival, intracorneal, intraocular, ophthalmic, auricular, transdermal, nasal, vaginal, uretheral, respiratory, and rectal administration.

The pharmaceutical compositions provided herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein may also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryopretectants, lyoprotectants, thickening agents, and inert gases.

The pharmaceutical compositions may also be administered topically by electroporation, iontophoresis, phonophoresis, sonophoresis and microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein may be provided in the forms of ointments, creams, and gels. Suitable ointment vehicles include oleaginous or hydrocarbon vehicles, including such as lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, Carbopol®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

The pharmaceutical compositions provided herein may be administered ophthalmically in the forms of solutions, suspensions, ointments, emulsions, gel-forming solutions, powders for solutions, gels, ocular inserts, and implants.

The pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or an surfactant, such as sorbitan trioleate, oleic acid, or an oligolacetic acid.

The pharmaceutical compositions provided herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

The pharmaceutical compositions provided herein for topical administration may be formulated to be immediate release or modified release, including delayed-, sustained-, pulsed-, controlled-, targeted, and programmed release.

D. Modified Release

The pharmaceutical compositions provided herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form may be fabricated using a matrix controlled release device known to those skilled in the art (see, Takada et al. in "Encyclopedia of Controlled Drug Delivery," Vol. 2, Mathiowitz ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lacetic acid-glycolic acid copolymers; poly-D-(−)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In further embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinylacetate copolymers, ethylene/propylene copolymers, ethylene/ethyl acrylate copolymers, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethyleneterephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate, and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients in the compositions.

The pharmaceutical compositions provided herein in a modified release dosage form may be prepared by methods known to those skilled in the art, including direct compression, dry or wet granulation followed by compression, melt-granulation followed by compression.

2. Osmotic Controlled Release Devices

The pharmaceutical compositions provided herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly (acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents are osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol, organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as Mannogeme EZ (SPI Pharma, Lewes, D E) can be used to provide faster delivery during the first couple of hours to promptly produce the desired therapeutic effect, and gradually and continually release of the remaining amount to maintain the desired level of therapeutic or prophylacetic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, β glucan acetate, β glucan triacetate, acetaldehyde dimethyl acetate, triacetate of locust bean gum, hydroxlated ethylene-vinylacetate, EC, PEG, PPG, PEG/PPG copolymers, PVP, HEC, HPC, CMC, CMEC, HPMC, HPMCP, HPMCAS, HPMCAT, poly (acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane may also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane may be formed post-coating by mechanical or laser drilling. Delivery port(s) may also be formed in situ by erosion of a plug of water-soluble material or by rupture of a thinner portion of the membrane over an indentation in the core. In addition, delivery ports may be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form may further comprise additional conventional excipients as described herein to promote performance or processing of the formulation.

The osmotic controlled-release dosage forms can be prepared according to conventional methods and techniques known to those skilled in the art (see, Remington: The Science and Practice of Pharmacy, supra; Santus and Baker, J. Controlled Release 1995, 35, 1-21; Verma et al., Drug Development and Industrial Pharmacy 2000, 26, 695-708; Verma et al., J. Controlled Release 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients.

3. Multiparticulate Controlled Release Devices

The pharmaceutical compositions provided herein in a modified release dosage form may be fabricated a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates may be made by the processes know to those skilled in the art, including wet-and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients as described herein may be blended with the pharmaceutical compositions to aid in processing and forming the multiparticulates. The resulting particles may themselves constitute the multiparticulate device or may be coated by various film-forming materials, such as enteric polymers, water-swellable, and water-soluble polymers. The multiparticulates can be further processed as a capsule or a tablet.

4. Targeted Delivery

The pharmaceutical compositions provided herein may also be formulated to be targeted to a particular tissue, receptor, or other area of the body of the subject to be treated, including liposome-, resealed erythrocyte-, and antibody-based delivery systems. Examples include, but are not limited to, U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

Provided are methods for treating, preventing, or ameliorating one or more symptoms of a benzodiazepine receptor mediated disease, comprising administering to a subject having or being suspected to have such a disease, a therapeutically effective amount of a compound of Formula 1, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof.

Further provided are methods of treating, preventing, or ameliorating one or more symptoms of a disease responsive to modulation of a benzodiazepine receptor, comprising administering to a subject having or being suspected to have such a disease, a therapeutically effective amount of a compound of Formula 1:

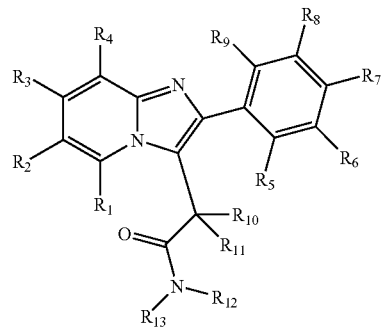

Formula 1 or a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof wherein:

$R_1$, $R_3$, $R_4$, $R_5$, $R_6$, $R_8$, $R_9$, $R_{10}$, and $R_{11}$ are independently selected from the group consisting of hydrogen and deuterium;

$R_2$, $R_7$, $R_{12}$, and $R_{13}$ are independently selected from the group consisting of —$CH_3$, —$CH_2D$, —$CHD_2$, and —$CD_3$;

provided that said compound of Formula 1 contains at least one deuterium atom; and provided that deuterium enrichment in said compound of Formula 1 is at least about 1%.

Further provided are methods of treating, preventing, or ameliorating one or more symptoms of a disease responsive to modulation of a benzodiazepine receptor, comprising administering to a subject having or being suspected to have such a disease, a therapeutically effective amount of a compound of Formula 1, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof.

Furthermore, provided herein are methods of modulating the activity of a benzodiazepine receptor, comprising contacting the receptor with at least one compound of Formula 1, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof. In one embodiment, the benzodiazepine receptor is expressed by a cell.

Provided herein are methods for treating a subject, including a human, having or suspected of having a disease or disorder involving sleep such as by way of example only, sleep related disorders, insomnia, narcolepsy, parasomnias, restless leg syndrome, sleep apnea, REM sleep behavior disorder, obstructive sleep apnea, hypersomnia, delayed sleep phase syndrome, advanced sleep phase syndrome, non-24-hour sleep-wake syndrome, sleep terror, somnambulism, sleep sickness, and dysomnias or for preventing such a disease or disorder in a subject prone to the disease; and/or for providing a human with a hypnotic, anxiolytic or anti-convulsive effect, comprising administering to the subject a therapeutically effective amount of a compound of Formula 1, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof; so as to affect decreased inter-individual variation in plasma levels of the compound or a metabolite thereof, during the treatment of the disease as compared to the corresponding non-isotopically enriched compound.

In certain embodiments, the inter-individual variation in plasma levels of the compounds of Formula 1, or metabolites thereof, is decreased by greater than about 5%, greater than about 10%, greater than about 20%, greater than about 30%, greater than about 40%, or by greater than about 50% as compared to the corresponding non-isotopically enriched compound.

Provided herein are methods for treating a subject, including a human, having or suspected of having a or disorder involving sleep such as by way of example only, sleep related disorders, insomnia, narcolepsy, parasomnias, restless leg syndrome, sleep apnea, REM sleep behavior disorder, obstructive sleep apnea, hypersomnia, delayed sleep phase syndrome, advanced sleep phase syndrome, non-24-hour sleep-wake syndrome, sleep terror, somnambulism, sleep sickness, and dysomnias or for preventing such a disease or disorder in a subject prone to the disease; and/or for providing a human with a hypnotic, anxiolytic or anti-convulsive effect, comprising administering to the subject a therapeutically effective amount of a compound of Formula 1, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof; so as to affect increased average plasma levels of the compound or decreased average plasma levels of at least one metabolite of the compound per dosage unit as compared to the corresponding non-isotopically enriched compound.

In certain embodiments, the average plasma levels of the compound of Formula 1 are increased by greater than about 5%, greater than about 10%, greater than about 20%, greater than about 30%, greater than about 40%, or greater than about 50% as compared to the corresponding non-isotopically enriched compounds.

In certain embodiments, the average plasma levels of a metabolite of the compound of Formula 1 are decreased by greater than about 5%, greater than about 10%, greater than about 20%, greater than about 30%, greater than about 40%, or greater than about 50% as compared to the corresponding non-isotopically enriched compounds Plasma levels of the compound of Formula 1, or metabolites thereof, are measured using the methods described by Li et al. (*Rapid Communications in Mass Spectrometry* 2005, 19, 1943-1950).

Provided herein are methods for treating a subject, including a human, having or suspected of having a disease or disorder involving sleep such as by way of example only, sleep related disorders, insomnia, narcolepsy, parasomnias, restless leg syndrome, sleep apnea, REM sleep behavior disorder, obstructive sleep apnea, hypersomnia, delayed sleep phase syndrome, advanced sleep phase syndrome, non-24-hour sleep-wake syndrome, sleep terror, somnambulism, sleep sickness, and dysomnias or for preventing such a disease or disorder in a subject prone to the disease; and/or for providing a human with a hypnotic, anxiolytic or anti-convulsive effect, comprising administering to the subject a therapeutically effective amount of a compound of Formula 1, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof; so as to affect a decreased inhibition of, and/or metabolism by at least one cytochrome $P_{450}$ isoform in the subject during the treatment of the disease as compared to the corresponding non-isotopically enriched compound.

Examples of cytochrome $P_{450}$ isoforms in a mammalian subject include, but are not limited to, CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R1, CYP2S1, CYP3A4, CYP3A5, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, and CYP51.

In certain embodiments, the decrease in inhibition of the cytochrome $P_{450}$ isoform by a compound of Formula 1 is greater than about 5%, greater than about 10%, greater than about 20%, greater than about 30%, greater than about 40%, or greater than about 50% as compared to the corresponding non-isotopically enriched compounds.

The inhibition of the cytochrome $P_{450}$ isoform is measured by the method of Ko et al. (*British Journal of Clinical Pharmacology,* 2000, 49, 343-351).

Provided herein are methods for treating a subject, including a human, having or suspected of having a disease or disorder involving sleep such as by way of example only, sleep related disorders, insomnia, narcolepsy, parasomnias, restless leg syndrome, sleep apnea, REM sleep behavior disorder, obstructive sleep apnea, hypersonmia, delayed sleep phase syndrome, advanced sleep phase syndrome, non-24-hour sleep-wake syndrome, sleep terror, somnambulism, sleep sickness, and dysonmias or for preventing such a disease or disorder in a subject prone to the disease; and/or for providing a human with a hypnotic, anxiolytic or anti-convulsive effect, comprising administering to the subject a therapeutically effective amount of a compound of Formula 1, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof; so as to affect a decreased metabolism via at least one polymorphically-expressed cytochrome $P_{450}$ isoform in the subject during the treatment of the disease as compared to the corresponding non-isotopically enriched compound.

Examples of polymorphically-expressed cytochrome $P_{450}$ isoforms in a mammalian subject include, but are not limited to, CYP2C8, CYP2C9, CYP2C19, and CYP2D6.

In certain embodiments, the decrease in metabolism of the compound of Formula 1 by at least one polymorphically-expressed cytochrome $P_{450}$ isoforms cytochrome $P_{450}$ isoform is greater than about 5%, greater than about 10%, greater than about 20%, greater than about 30%, greater than about 40%, or greater than about 50% as compared to the corresponding non-isotopically enriched compound.

The metabolic activities of the cytochrome $P_{450}$ isoforms are measured by the method described in Example 22.

Provided herein are methods for treating a subject, including a human, having or suspected of having a disease or disorder involving sleep such as by way of example only, sleep related disorders, insomnia, narcolepsy, parasomnias, restless leg syndrome, sleep apnea, REM sleep behavior disorder, obstructive sleep apnea, hypersomnia, delayed sleep phase syndrome, advanced sleep phase syndrome, non-24-hour sleep-wake syndrome, sleep terror, somnambulism, sleep sickness, and dysomnias or for preventing such a disease or disorder in a subject prone to the disease; and/or for providing a human with a hypnotic, anxiolytic or anti-convulsive effect, comprising administering to the subject a therapeutically effective amount of a compound of Formula 1, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof; so as to affect at least one statistically-significantly improved disease-control and/or disease-eradication endpoint, as compared to the corresponding non-isotopically enriched compound.

An example of an improved disease-control and/or disease-eradication endpoint includes but is not limited to, statistically significant improvement of sleep indices as compared to the corresponding non-isotopically enriched compound.

In another aspect, are provided methods for treating a mammalian subject, particularly a human having, suspected of having, or being prone to a disease or condition involving a benzodiazepine receptor, comprising administering to a mammalian subject in need thereof a therapeutically effective amount of a benzodiazepine receptor modulator comprising at least one of the compounds of Formula 1, the (−)-enantiomer of one of the compounds of Formula 1, the (+)-enantiomer of one of the compounds of Formula 1, or a pharmaceutically acceptable salt, solvate, or prodrug thereof, so as to affect increased average plasma levels of said compound or decreased average plasma levels of at least one metabolite of said compound per dosage unit as compared to the non-isotopically enriched compound.

Provided herein are methods for treating a subject, including a human, having or suspected of having a disease or disorder involving sleep such as by way of example only, sleep related disorders, insomnia, narcolepsy, parasomnias, restless leg syndrome, sleep apnea, REM sleep behavior disorder, obstructive sleep apnea, hypersomnia, delayed sleep phase syndrome, advanced sleep phase syndrome, non-24-hour sleep-wake syndrome, sleep terror, somnambulism, sleep sickness, and dysomnias or for preventing such a disease or disorder in a subject prone to the disease; and/or for providing a human with a hypnotic, anxiolytic or anti-convulsive effect, comprising administering to the subject a therapeutically effective amount of a compound of Formula 1, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof; or a pharmaceutically acceptable salt, solvate, or prodrug thereof; so as to affect an improved clinical effect as compared to the corresponding non-isotopically enriched compound. Examples of improved clinical effects include, but are not limited to, statistically-significant improvement of sleep indices, more rapid symptomatic relief from sleep disturbances, and improved mood patterns, as compared to the corresponding non-isotopically enriched compound.

Depending on the disease to be treated and the subject's condition, the compound of Formula 1 provided herein may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical (e.g., transdermal or local) routes of administration, and may be formulated, alone or together, in suitable dosage unit with pharmaceutically acceptable carriers, adjuvants and vehicles appropriate for each route of administration.

The dose may be in the form of one, two, three, four, five, six, or more sub-doses that are administered at appropriate intervals per day. The dose or sub-doses can be administered in the form of dosage units containing from about 0.1 to about 1000 milligram, from about 0.1 to about 500 milligrams, or from 0.5 about to about 100 milligram active ingredient(s) per dosage unit, and if the condition of the patient requires, the dose can, by way of alternative, be administered as a continuous infusion.

In certain embodiments, an appropriate dosage level is about 0.01 to about 100 mg per kg patient body weight per day (mg/kg per day), about 0.01 to about 50 mg/kg per day, about 0.01 to about 25 mg/kg per day, or about 0.05 to about 10 mg/kg per day, which may be administered in single or multiple doses. A suitable dosage level may be about 0.01 to about 100 mg/kg per day, about 0.05 to about 50 mg/kg per day, or about 0.1 to about 10 mg/kg per day. Within this range the dosage may be about 0.01 to about 0.1, about 0.1 to about 1.0, about 1.0 to about 1.0, or about 10 to about 50 mg/kg per day.

In another embodiment, are provided methods for treating a mammualian subject, particularly a human having, suspected of having, or being prone to a disease or condition involving a benzodiazepine receptor, comprising administering to a mammalian subject in need thereof a therapeutically effective amount of a benzodiazepine receptor modulator comprising at least one of the compounds of Formula 1, the (−)-enantiomer of one of the compounds of Formula 1, the (+)-enantiomer of one of the compounds of Formula 1, or a pharmaceutically acceptable salt, solvate, or prodrug thereof, so as to affect improved neurotransmitter levels as compared to the non-isotopically enriched compound.

In some embodiments, neurotransmitter levels are increased by greater than about 5%. In other embodiments, neurotransmitter levels are increased by greater than about 10%. In other embodiments, neurotransmitter levels are increased by greater than about 20%. In other embodiments, neurotransmitter levels are increased by greater than about 30%. In other embodiments, neurotransmitter levels are increased by greater than about 40%. In other embodiments, neurotransmitter levels are increased by greater than about 50%.

Neurotransmitter levels are measured by the methods of Li, (*Rapid Communications in Mass Spectrometry*, 2005, 19(14), 1943-50).

In some embodiments, the disease or condition involving a benzodiazepine receptor is selected from the group consisting of a sleep disorder and/or a disease in which a hypnotic, an anxiolytic or an anti-convulsive effect is beneficial.

In some embodiments, the method for treating a mammalian subject, particularly a human having, suspected of having, or being prone to a disease or condition involving a benzodiazepine receptor, comprising administering to a mammalian subject in need thereof a therapeutically effective amount of a benzodiazepine receptor modulator comprising a compound of Formula 1, wherein said compound of Formula 1 represents a mixture of the (+)-enantiomer and the (−)-enantiomer, or wherein said compound of Formula 1 contains about 90% or more by weight of the (−)-enantiomer of said compound and about 10% or less by weight of the (+)-enantiomer of said compound, or wherein said compound of Formula 1 contains about 90% or more by weight of the (+)-enantiomer of said compound and about 10% or less by weight of the (−)-enantiomer of said compound; provided that said compound of Formula 1 contains at least one deuterium atom; and provided that deuterium enrichment in said compound of Formula 1 is at least about 1%.

Combination Therapy

The compounds provided herein may also be combined or used in combination with other agents useful in the treatment, prevention, or amelioration of one or more symptoms of the diseases or conditions for which the compound provided herein are useful, sleep related disorders, insomnia, narcolepsy, parasomnias, restless leg syndrome, sleep apnea, REM sleep behavior disorder, obstructive sleep apnea, hypersonmia, delayed sleep phase syndrome, advanced sleep phase syndrome, non-24-hour sleep-wake syndrome, sleep terror, somnambulism, sleep sickness, and dysomnias. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced).

Such other agents, adjuvants, or drugs, may be administered, by a route and in an amount commonly used therefor, simultaneously or sequentially with a compound of Formula 1. When a compound of Formula 1 provided herein is used contemporaneously with one or more other drugs, a pharmaceutical composition containing such other drugs in addition to the compound provided herein may be utilized, but is not required. Accordingly, the pharmaceutical compositions provided herein include those that also contain one or more other active ingredients or therapeutic agents, in addition to the compound provided herein.

In certain embodiments, the compounds provided herein can be combined with one or more modulators of $GABA_A$ receptors known in the art, including, but not limited to, imidazolpyridines, pyrazolopyrimidines, such as by way of example only, zaleplon, cyclopyrrones, by way of example only, eszopiclone, zopiclone, chlordiazepoxide, diazepam, nitrazepam, and flurazepam.

In certain embodiments, the compounds provided herein can be combined with one or more natural, semisynthetic, or fully synthetic opioids known in the art, including, but not limited to, morphine, codeine, thebain, diacetylmorphine, oxycodone, hydrocodone, hydromorphone, oxymorphone, nicomorphine, fentanyl, α-methylfentanyl, alfentanil, sufentanil, remifentanyl, carfentanyl, ohmefentanyl, pethidine, ketobemidone, propoxyphene, dextropropoxyphene, methadone, loperamide, pentazocine, buprenorphine, etorphine, butorphanol, nalbufine, levorphanol, naloxone, naltrexone, and tramadol.

In certain embodiments, the compounds provided herein can be combined with one or more local and/or general anesthetics and sedatives known in the art, including, but not limited to, propofol, procaine, lidocaine, prilocalne, bupivicaine, levobupivicaine, nitrous oxide, halothane, enflurane, isoflurane, sevoflurane, desflurane, thiopental, methohexital, etomidate, diazepam, midazolam, lorazepam, succinylcholine, vecuronium, rocuronium, pipecuronium, rapacuronium, tubocurarine, and gallamine.

The compounds provided herein can also be administered in combination with other classes of compounds, including, but not limited to, endothelin converting enzyme (ECE) inhibitors, such as phosphoramidon; thromboxane receptor antagonists, such as ifetroban; potassium channel openers; thrombin inhibitors, such as hirudin; growth factor inhibitors, such as modulators of PDGF activity; platelet activating factor (PAF) antagonists; anti-platelet agents, such as GPIIb/IIIa blockers (e.g., abdximab, eptifibatide, and tirofiban), P2Y (AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopepsidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, or atavastatin or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-adrenergic agents; β-adrenergic agents, such as carvedilol and metoprolol; antiarrhythmic agents; diuretics, such as chlorothlazide, hydrochlorothiazide, flumethiazide, hydroflumethiazide, bendroflumethiazide, methylchlorothiazide, trichloromethiazide, polythiazide, benzothlazide, ethacrynic acid, tricrynafen, chlorthalidone, furosenilde, musolimine, bumetamide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguamides (e.g. metformin), glucosidase inhibitors (e.g., acarbose), insulins, meglitinides (e.g., repaglinide), sulfonylureas (e.g., glimepiride, glyburide, and glipizide), thiozolidinediones (e.g. troglitazone, rosiglitazone and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, vardenafil); protein tyrosine kinase inhibitors; antiinflammatories; antiproliferatives, such as methotrexate, FK506 (tacrolimus, Prograf), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrridine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone anatagonists, and octreotide acetate; microtubule-disruptor agents, such as ecteinascidins; microtubule-stabilizing agents, such as pacitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporins; steroids, such as prednisone and dexamethasone; cytotoxic drugs, such as azathiprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) selective inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

Kits/Articles of Manufacture

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprise a compound with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein. These other therapeutic agents may be used, for example, in the amounts indicated in the Physicians' Desk Reference (PDR) or as otherwise determined by one of ordinary skill in the art.

EXAMPLES

For all of the following examples, standard work-up and purification methods known to those skilled in the art can be utilized. Synthetic methodologies illustrated in Scheme 1 is intended to exemplify the applicable chemistry through the use of specific examples and are not indicative of the scope of what is claimed herein.

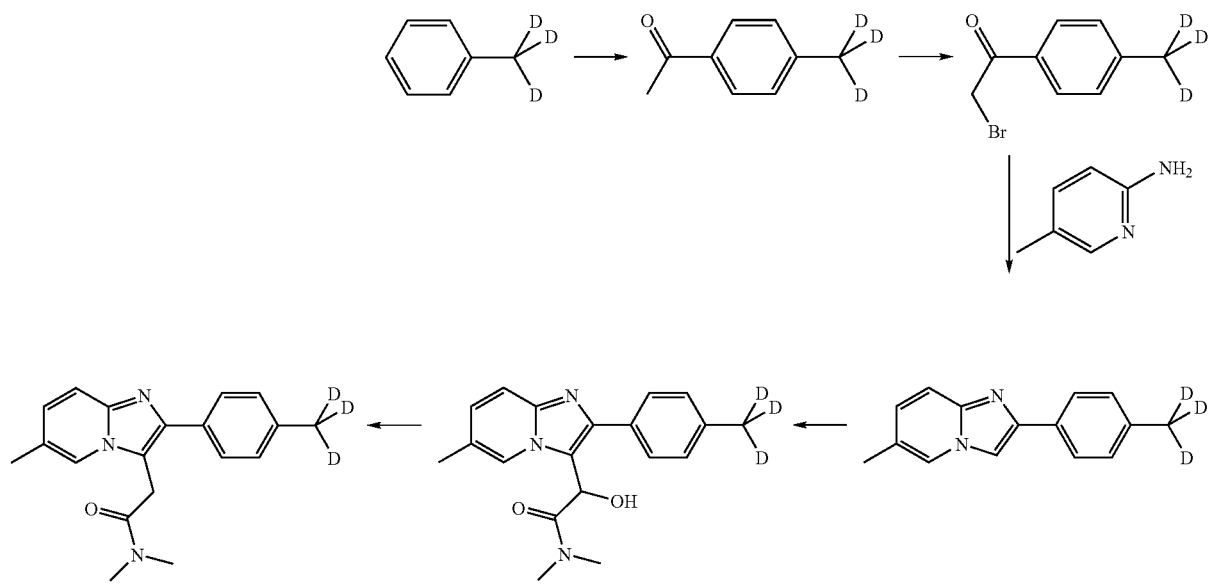

Example 1

1-p-tolyl-ethanone

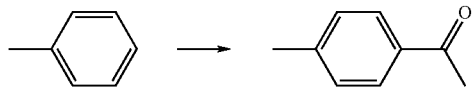

Anhydrous aluminum chloride (89.6 g, 0.67 mol) was added to a solution of toluene (28.5 g, 0.3 μmol) in 120 mL of dry carbon disulfide. The mixture was heated to reflux and acetic anhydride (24.5 g, 0.24 mol) was added over one hour. Heating was continued for an additional hour. The solvent was removed by distillation. The reaction mixture was cooled and slowly poured into a well-stirred mixture of ice and hydrochloric acid. The mixture was extracted several times with ether. The combined extracts were washed with water and 10% sodium hydroxide, dried over calcium chloride, filtered, and the solvent was removed. Distillation gave the desired product 1-p-tolyl-ethanone (27.08 g). $^1$H NMR (300 MHz, DMSO-$d_6$) δ 2.36 (s, 3H), 2.50 (s, 3H), 7.32 (d, 2H), 7.85 (d, 2H); EI-MS (M$^+$): 134.

Example 2

2-Bromo-1-p-tolyl-1-ethanone

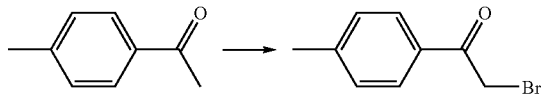

To a solution of 1-p-tolyl-ethanone (0.5 g, 4.16 mmol) in dichloromethane-methanol (50 ml-20 mL) was added tetrabutylammonium tribromide (2.2 g, 4.58 mmol) at room temperature. The mixture was stirred until the orange color faded. The solvent was then distilled under reduced pressure and the resulting precipitate was extracted with ethyl acetate. The organic layer was dried over sodium sulfate and evaporated in vacuo to give a residue which was purified by flash column chromatography to yield the desired product 2-bromo-1-p-tolyl-1-ethanone (0.74 g, 84%). $^1$H NMR (300 MHz, DMSO-$d_6$) δ 2.39 (s, 3H), 4.89 (s, 2H), 7.37 (d, 2H), 7.89 (d, 2H); ESI-MS (MH$^+$): 213 and 215.

Example 3

6-Methyl-2-p-tolyl-imidazo[1,2-a]pyridine

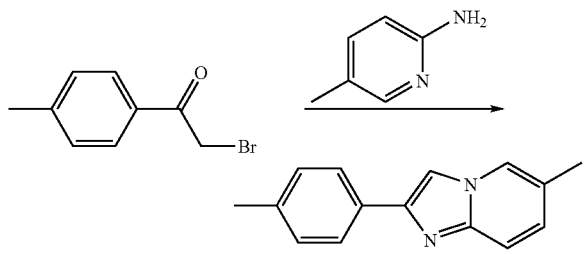

A solution of 2-bromo-1-p-tolyl-ethanone (500 mg, 2.3 mmol) in dimethylformamide (2 mL) was added slowly to a solution of 5-methyl-pyridin-2-yl-amine (249 mg, 2.3 mmol) in dimethylformamide (2 mL). NaHCO$_3$ (386 mg, 4.6 mmol) was added in portions and the mixture was stirred at room temperature for 15 minutes, then at reflux for 1.5 hours. The mixture was cooled and poured into water (5 mL). The solid was collected, washed with water (2 mL) and recrystallized from dimethylformamide (5 mL) to yield the desired product 6-methyl-2-p-tolyl-imidazo[1,2-a]pyridine (360 mg, 70%). $^1$H NMR (300 MHz, DMSO-$d_6$) δ 2.27 (s, 3H), 2.32 (s, 3H), 7.08 (d, 1H), 7.21 (d, 2H), 7.46 (d, 1H), 7.83 (d, 2H), 8.24 (s, 1H), 8.29 (s, 1H); ESI-MS (MH$^+$), 223.

Example 4

$d_{14}$-6-Methyl-2-p-tolyl-imidazo[1,2-a]pyridine

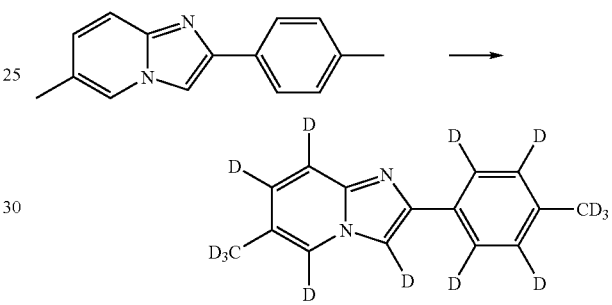

A mixture of 6-methyl-2-p-tolyl-imidazo[1,2-a]pyridine (2 g, 9 mmol), 10% Pd/C (20% weight, 0.4 g), sodium formate (306 mg, 4.5 mmol), D$_2$O and dioxane (20 ml, D$_2$O/dioxane, 8/1, v/v) was degassed by bubbling a steam of nitrogen into the mixture for 2 minutes. The reaction was heated to 160° C. for 30 hours. The reaction was cooled, extracted with methanol, dried, concentrated and purified by flash column chromatography and the process was repeated again to yield the desired product $d_{14}$-6-methyl-2-p-tolyl-imidazo[1,2-a]pyridine (450 mg, 21% yield). The percent incorporation of deuterium was determined by NMR. ESI-MS (MH$^+$) 237.

Example 5

$d_{13}$-2-Hydroxy-N,N-dimethyl-2-(6-methyl-2-p-tolyl-imidazo[1,2-a]pyridin-3-yl)-acetamide

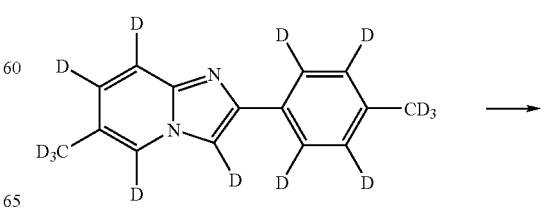

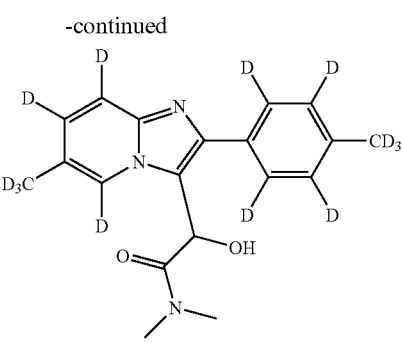

N,N-Dimethyl-2-oxo-acetamide hemihydrate (523 mg) was added to a solution of $d_{14}$-6-methyl-2-p-tolyl-imidazo[1,2-a]pyridine (450 mg, 2 mmol) in 4-methyl-2-pentanone (10 mL) at 60° C. and stirred for 3 hours. The temperature was increased to 80° C. and stirring was maintained for an additional 12 hours. The reaction was cooled and the solvent was removed under reduced pressure. The residue was purified by flash column chromatography to yield the desired product $d_{13}$-2-hydroxy-N,N-dimethyl-2-(6-methyl-2-p-tolyl-imidazo[1,2-a]pyridin-3-yl)-acetamide (400 mg, 60%). $^1$H NMR (300 MHz, CDCl$_3$) δ 7.68 (s, 0.24H), 7.28 (s, 0.30H), 5.73 (s, 1H), 4.92 (br, 1H), 2.87 (s, 3H), 2.36 (s, 3H); ESI-MS (MH)$^+$337.

Example 6

$d_{13}$-N,N-dimethyl-2-(6-methyl-2-p-totyl-imidazo[1,2-α]pyridine-3-yl)-acetamide($d_{13}$-ambien)

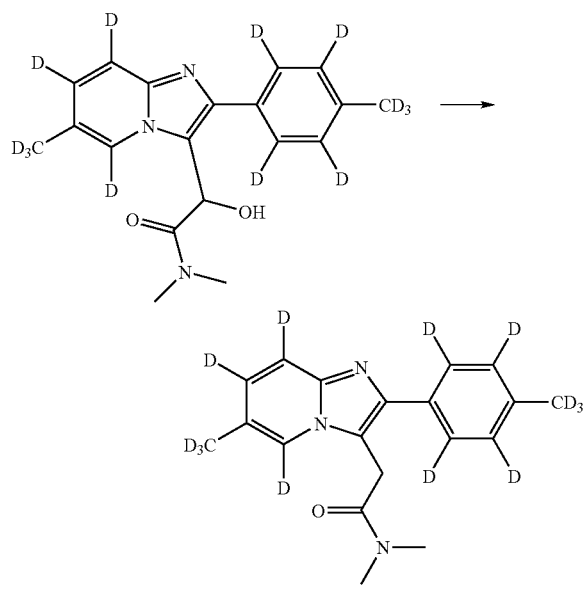

Phosphorus tribromide was added to a solution of $d_{13}$-2-hydroxy-N,N-dimethyl-2-(6-methyl-2-p-tolyl-imidazo[1,2-a]pyridin-3-yl)-acetamide (400 mg, 1.19 mmol) in tetrahydrofuran at 40° C. A white precipitate formed immediately. The mixture was heated at reflux until completion. The mixture was added to a saturated aqueous solution of NaHCO$_3$ (50 mL) and extracted with ethyl acetate. The combined organic layers were dried over sodium sulfate, filtered and concentrated to yield the desired product $d_{13}$-N,N-dimethyl-2-(6-methyl-2-p-tolyl-imidazo[1,2-α]pyridine-3-yl)-acetamide (150 mg, 38%). $^1$H NMR (300 MHz, CDCl$_3$) δ 7.56 (s, 0.27H), 4.11 (s, 2H), 2.96 (s, 3H), 2.90 (s, 3H); ESI-MS (MH+): 321.

Example 7

$d_6$-5-Methyl-pyridin-2-yl-amine

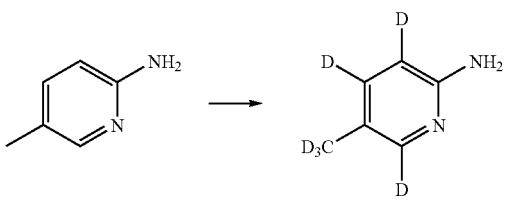

A mixture of 5-methyl-pyridin-2-yl-amine (1 g, 9.2 mmol), 10% Pd/C (20% weight, 0.2 g), sodium formate (312 mg, 4.6 mmol), D$_2$O and dioxane (34 ml, D$_2$O/dioxane, 8/1, v/v) was degassed by bubbling a steam of nitrogen into the mixture for 2 minutes. The reaction was heated to 180° C. for 24 hours. The reaction was cooled, filtered, washed with methanol, concentrated and purified by flash column chromatography to give the desired product $d_6$-5-methyl-pyridin-2-yl-amine (661 mg, 58%). $^1$H NMR (300 MHz, D$_2$O) δ 3.18 (s); ESI-MS (MH$^+$): 115.

Example 8

$d_6$-6-Methyl-2-p-tolyl-imidazo[1,2-a]pyridine

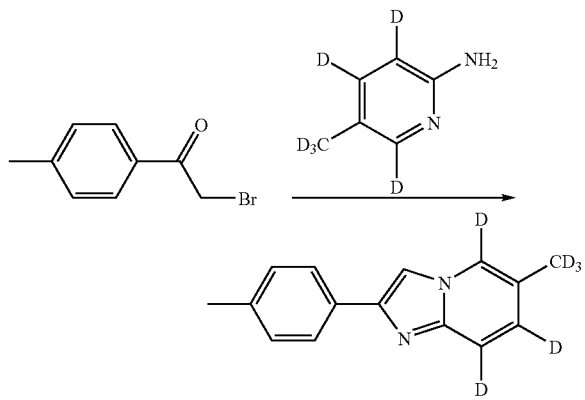

Prepared according to Example 3 by substituting $d_6$-5-methyl-pyridin-2-yl-amine for 5-methyl-pyridin-2-yl-amine. $^1$H NMR (300 MHz, CDCl$_3$) δ 2.38 (s, 3H), 7.24 (d, 2H), 7.74 (s, 1H), 7.83 (d, 2H); ESI-MS (MH$^+$): 229.

Example 9 d$_6$-2-Hydroxy-N,N-dimethyl-2-(6-methyl-2-p-tolyl-imidazo[1,2-a]pyridin-3-yl)-acetamide

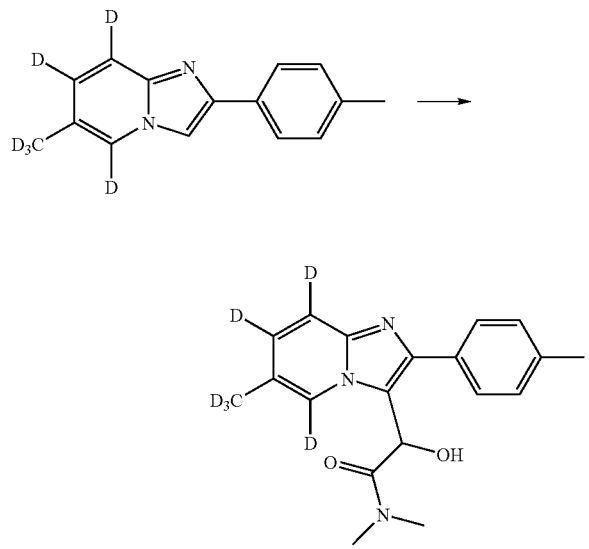

Prepared according to Example 5. $^1$H NMR (300 MHz, CDCl$_3$) δ 7.68 (s, 2H), 7.28 (s, 2H), 5.72 (s, 1H), 4.85 (br, 1H), 2.87 (s, 3H), 2.46 (s, 3H), 2.36 (s, 3H); ESI-MS (MH$^+$): 330.

Example 10 d$_6$-N,N-dimethyl-2-(6-methyl-2-p-tolyl-imidazo[1,2-α]pyridine-3-yl)-acetamide(d$_6$-ambien)

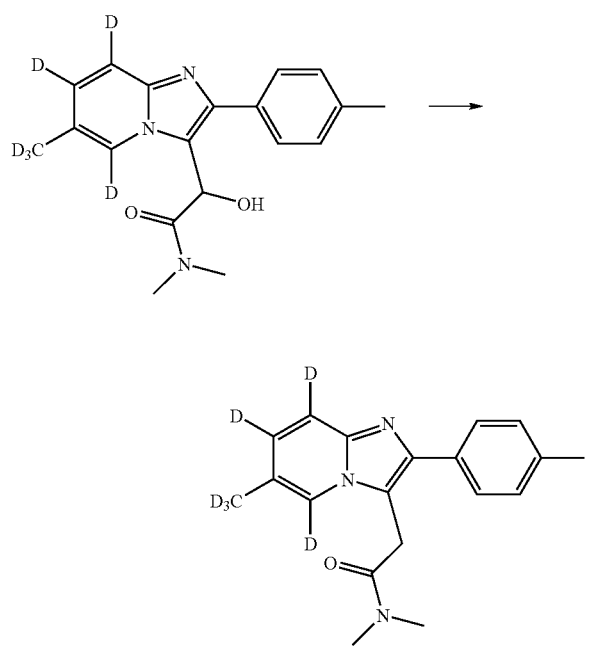

Prepared according to Example 6. $^1$H NMR (300 MHz, CDCl$_3$) δ 7.56 (s, 2H), 7.27 (s, 2H), 4.11 (s, 2H), 2.96 (s, 3H), 2.89 (s, 3H), 2.41 (s, 3H); ESI-MS (MH$^+$): 314.

Example 11 d$_3$-1-p-tolyl-ethanone

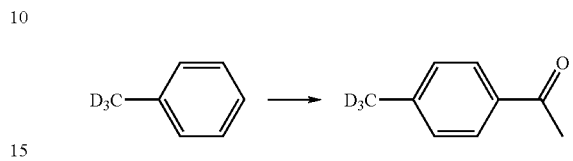

Prepared according to Example 1 by substituting d$_3$-toluene for toluene, $^1$H NMR (300 MHz, CDCl$_3$): δ 7.88 (d, J=8.1 Hz, 2H), 7.27 (d, J=8.1 Hz, 2H), 2.60 (s, 3H); EI-MS m/z=137 (radical cation)

Example 12 d$_3$-2-Bromo-1-p-tolyl-1-ethanone

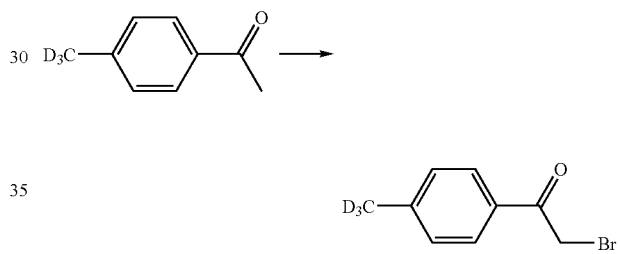

Prepared according to Example 2, $^1$H NMR (300 MHz, CDCl$_3$): δ 7.89 (d, J=7.8 Hz, 2H), 7.28 (d, J=7.8 Hz, 2H), 4.44 (s, 2H);

Example 13 d$_3$-6-Methyl-2-p-tolyl-imidazo[1,2-a]pyridine

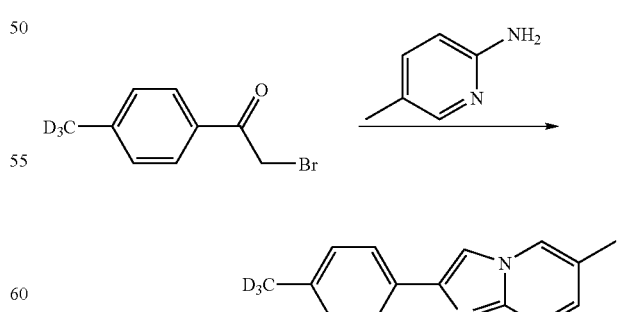

Prepared according to Example 3, $^1$H NMR (300 MHz, CDCl$_3$) δ 7.86 (m, 3H), 7.74 (s, 1H), 7.53 (d, J=9.0 Hz, 2H), 7.25 (d, J=7.8 Hz, 2H), 7.01 (d, J=9.0 Hz, 1H), 2.34 (s, 3H); ESI-MS m/z=226 (MH$^+$)

Example 14 d$_3$-2-Hydroxy-N,N-dimethyl-2-(6-methyl-2-p-tolyl-imidazo[1,2-a]pyridin-3-yl)-acetamide

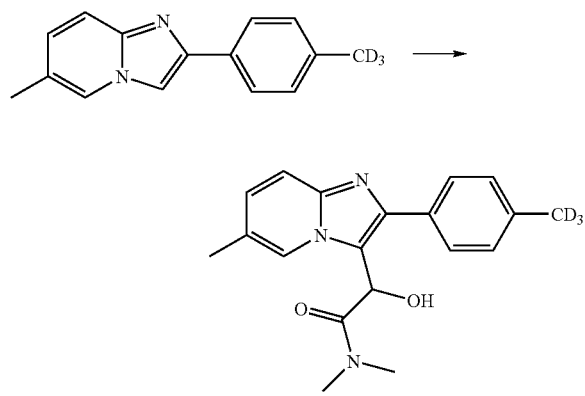

Prepared according to Example 5, $^1$H NMR (300 MHz, CDCl$_3$) δ 7.98 (s, 1H), 7.68 (d, J=8.1 Hz, 2H), 7.59 (d, J=9.0 Hz, 1H), 7.27 (d, J=8.1 Hz, 2H), 7.11 (d, J=9.0 Hz, 1H), 5.72 (s, 1H), 2.96 (s, 3H), 2.39 (s, 3H), 2.34 (s, 3H); ESI-MS m/z=327 (MH$^+$).

Example 15 d$_3$-N,N-dimethyl-2-(6-methyl-2-p-tolyl-imidazo[1,2-α]pyridine-3-yl)-acetamide(d$_3$-ambien)

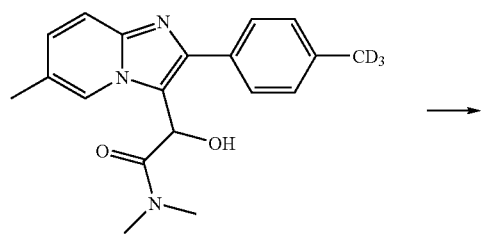

Prepared according to Example 6, $^1$H NMR (300 MHz, CDCl$_3$) δ 8.02 (s, 1H), 7.55 (m, 3H), 7.26 (d, J=8.1 Hz, 2H), 7.05 (d, J=9.0 Hz, 1H), 4.11 (s, 2H), 2.96 (s, 3H), 2.89 (s, 3H), 2.36 (s, 3H); ESI-MS m/z=311 (MH+)

Example 16 d$_6$-2,3-Dihydroxy-N,N,N'N'-tetramethylsuccinamide

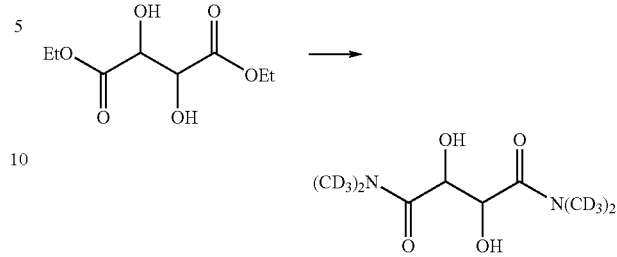

The procedure is carried out according to Seebach et al. *Organic Syntheses* 1990, *Coll. Vol* 7, 41. Into a mixture of 618 g (3 mol) of diethyl tartrate and 600 mL of freshly distilled methanol in a 2-L Erlenmeyer flask is poured at least 450 mL (7 mol) of liquid, anhydrous, cold (−78° C.) d$_6$-dimethylamine. The mixture is swirled briefly and then allowed to stand in a hood for 3 days with a drying tube in place. After seeding and cooling in a refrigerator overnight, the massive crystals are collected by suction filtration. The filtrate is concentrated, seeded, and cooled to yield a second crop. The combined crystals are washed with cold methanol (−30° C.) and dried under reduced pressure at 70-100° C. (oil bath) to give the desired product, d$_6$-2,3-dihydroxy-N,N,N',N'-tetramethylsuccinamide.

Example 17 d$_6$-N,N-Dimethyl glyoxamide

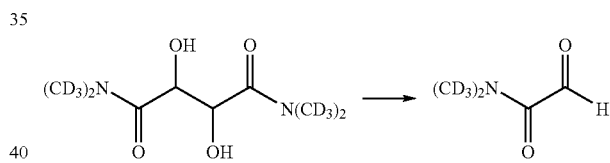

The procedure is carried out according to Trova et al. *Bioorg. Med. Chem.* 2003, 11(13), 2695-2708. A solution of d$_6$-2,3-dihydroxy-N,N,N',N'-tetramethylsuccinamide (9.79 mmol) in dichloromethane (60 mL) is magnetically stirred at 0° C., under dry nitrogen, as periodic acid dihydrate (12.2 mmol) is added. The resulting solution is stirred for 4.5 hours, decanted from the solid precipitate, dried over sodium sulfate, filtered, and the solvent is evaporated under reduced pressure to provide the desired product, d$_6$-N,N-dimethyl glyoxamide, as an oil.

Example 18 d$_{19}$-2-Hydroxy-N,N-dimethyl-2-(6-methyl-2-p-tolyl-imidazo[1,2-a]pyridin-3-yl)-acetamide

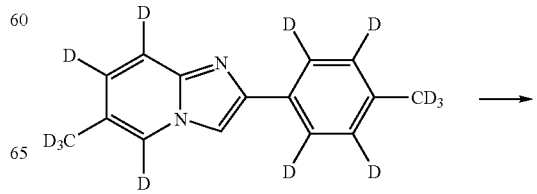

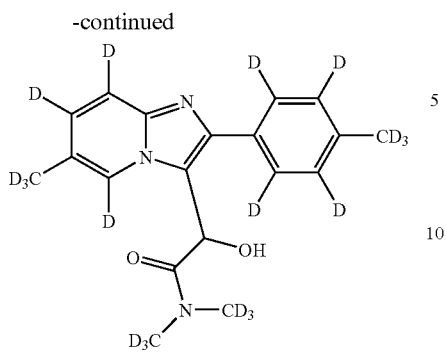

The title compound is prepared according to Example 5 by substituting $d_6$-N,N-dimethyl glyoxamide for N,N-dimethyl glyoxamide.

Example 19

$d_{19}$-N,N-dimethyl-2-(6-methyl-2-p-tolyl-imidazo[1,2-α]pyridine-3-yl)-acetamide($d_{19}$-ambien)

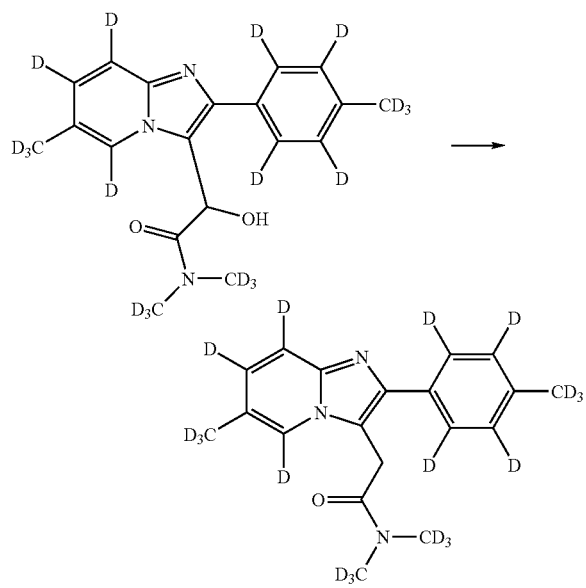

The title compound is prepared according to Example 6.

Example 20

$d_{21}$-N,N-dimethyl-2-(6-methyl-2-p-tolyl-imidazo[1,2-α]pyridine-3-yl)-acetamide($d_{21}$-ambien)

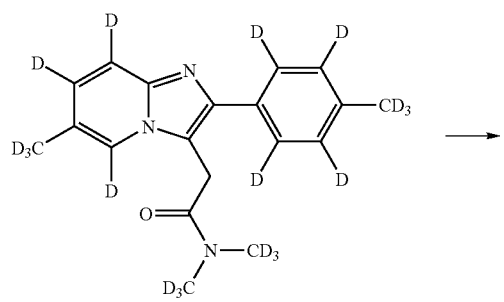

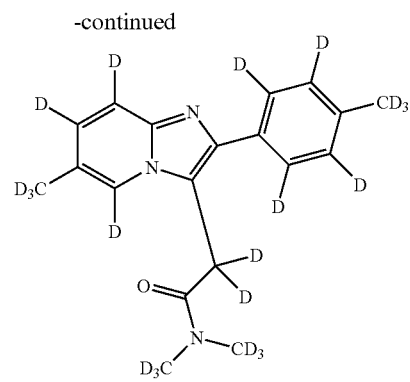

$d_{19}$-Ambien (0.014 mmol) is taken up in 0.5 ml of $d_4$-methanol and added dropwise to a 0.1M solution of sodium carbonate in $D_2O$ (pH=11.4) at ambient temperature; the solution is stirred for 4 days, diluted with dichloromethane, washed with brine and dried over anhydrous magnesium sulfate. The solvent is removed under reduced pressure to yield the desired product, $d_{21}$-ambien.

Example 21

In vitro Liver Microsomal Stability Assay

Liver microsomal stability assays were conducted at 1 mg per mL liver microsome protein with an NADPH-generating system in 2% $NaHCO_3$ (2.2 mM NADPH, 25.6 mM glucose 6-phosphate, 6 units per mL glucose 6-phosphate dehydrogenase and 3.3 mM $MgCl_2$). Test compounds were prepared as solutions in 20% acetonitrile-water and added to the assay mixture (final assay concentration 5 microgram per mL) and incubated at 37° C. Final concentration of acetonitrile in the assay were <1%. Aliquots (50 μL) were taken out at times 0, 15, 30, 45, and 60 minutes, and diluted with ice cold acetonitrile (200 μL) to stop the reactions. Samples were centrifuged at 12000 RPM for 10 minutes to precipitate proteins. Supernatants were transferred to microcentrifuge tubes and stored for LC/MS/MS analysis of the degradation half-life of the test compounds. It has thus been found that the compounds of formula (I) according to the present invention that have been tested in this assay showed an increase of 10% or more in the degradation half-life, as compared to the non-isotopically enriched drug. For example, the degradation half-life of $d_3$-ambien (Example 15), $d_6$-ambien (Example 10) and $d_{13}$-ambien (Example 6) were increased by 15-66% as compared to non-isotopically enriched ambien.

Example 22

In vitro Metabolism Using Human Cytochrome $P_{450}$ enzymes

The cytochrome $P_{450}$ enzymes are expressed from the corresponding human cDNA using a baculovirus expression system (BD Biosciences). A 0.25 milliliter reaction mixture containing 0.8 milligrams per milliliter protein, 1.3 millimolar $NADP^+$, 3.3 millimolar glucose-6-phosphate, 0.4 U/mL glucose-6-phosphate dehydrogenase, 3.3 millimolar magnesium chloride and 0.2 millimolar of a compound of Formula 1, the corresponding non-isotopically enriched compound or standard or control in 100 millimolar potassium phosphate (pH 7.4) is incubated at 37° C. for 20 min. After incubation, the reaction is stopped by the addition of an appropriate solvent (e.g. acetonitrile, 20% trichloroacetic acid, 94% acetonitrile/ 6% glacial acetic acid, 70% perchloric acid, 94% acetonitrile/ 6% glacial acetic acid) and centrifuged (10,000 g) for 3 minutes. The supernatant is analyzed by HPLC/MS/MS.

| Cytochrome $P_{450}$ | Standard |
|---|---|
| CYP1A2 | Phenacetin |
| CYP2A6 | Coumarin |
| CYP2B6 | [$^{13}$C]—(S)-mephenytoin |
| CYP2C8 | Paclitaxel |
| CYP2C9 | Diclofenac |
| CYP2C19 | [$^{13}$C]—(S)-mephenytoin |
| CYP2D6 | (+/−)-Bufuralol |
| CYP2E1 | Chlorzoxazone |
| CYP3A4 | Testosterone |
| CYP4A | [$^{13}$C]-Lauric acid |

Example 23

Pentobarbital-induced Sleep Test in Mice

Male Swiss mice (20-25 g) are randomly divided into groups of 10 and housed in a vivarium with 12 hour light-dark cycle at 24±1° C. The test compounds are dissolved in dimethylsulfoxide as stock solutions of 50 mg/mL. Each group is i.p. injected with the test compounds 30 minutes before intravenous administration of pentobarbital sodium (25 mg/kg). The control group is treated i.p. with dimethylsulfoxide alone to determine the duration of hypnosis. Sleep time in test animals and control animals is determined by measuring the difference between the time of loss and recovery of the righting reflex.

What is claimed is:

1. A compound having a structural formula selected from the group consisting of:

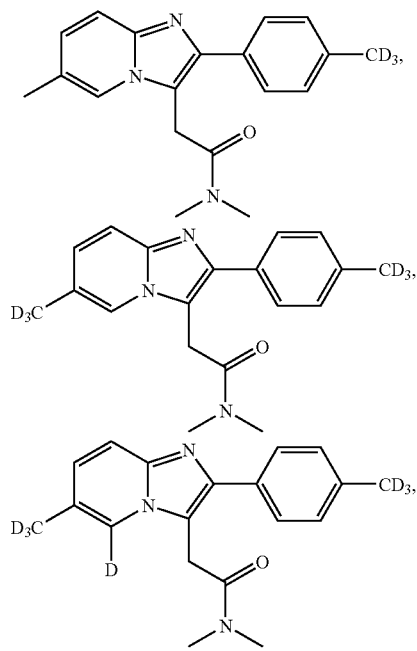

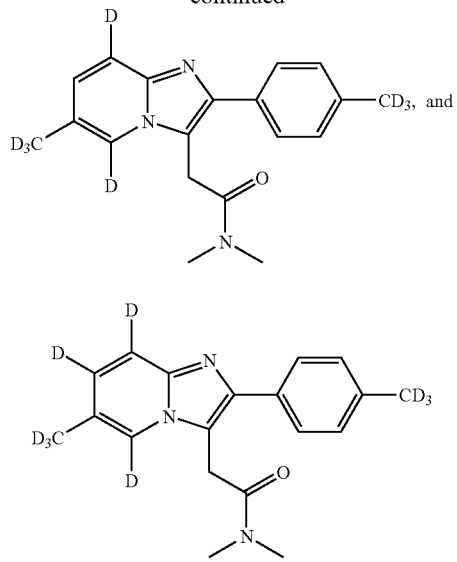

or a pharmaceutically acceptable salt thereof;
wherein each position designated as D has deuterium enrichment of at least 1%.

2. The compound of claim 1 wherein each position designated as D has deuterium enrichment of at least 10%.

3. The compound of claim 1 wherein each position designated as D has deuterium enrichment of at least 20%.

4. The compound of claim 1 wherein each position designated as D has deuterium enrichment of at least 50%.

5. The compound of claim 1 wherein each position designated as D has deuterium enrichment of at least 70%.

6. The compound of claim 1 wherein each position designated as D has deuterium enrichment of at least 80%.

7. The compound of claim 1 wherein each position designated as D has deuterium enrichment of at least 90%.

8. The compound of claim 1 wherein each position designated as D has deuterium enrichment of at least 95%.

9. A pharmaceutical composition comprising a therapeutically effective amount of a compound according to claim 1 together with a pharmaceutically acceptable carrier or excipient.

10. The pharmaceutical composition of claim 9, wherein said composition is suitable for oral, parenteral, or intravenous infusion administration.

11. The pharmaceutical composition of claim 10, wherein said oral administration comprises administering a tablet or a capsule.

12. The pharmaceutical composition of claim 10, wherein said compound of claim 1 is administered in a dose of about 0.1 milligram to about 100 milligram total daily.

13. A compound as recited in claim 1, having the structural formula:

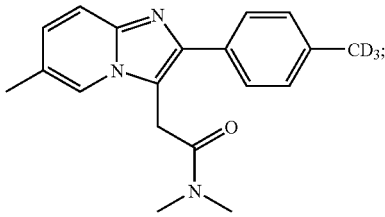

14. A compound as recited in claim 1, having the structural formula:

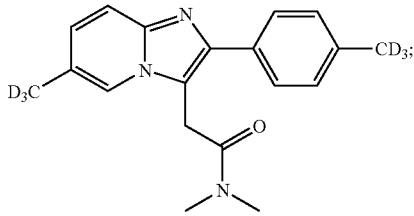

wherein each position designated as D has deuterium enrichment of at least 1%.

15. A compound as recited in claim 1, having the structural formula:

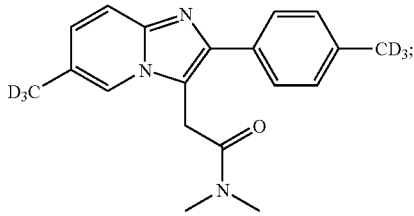

wherein each position designated as D has deuterium enrichment of at least 1%.

16. A compound as recited in claim 1, having the structural formula:

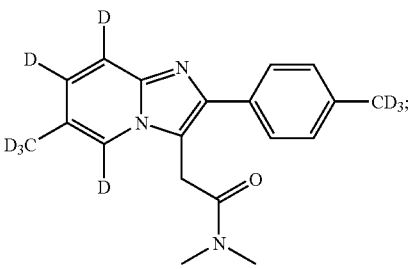

wherein each position designated as D has deuterium enrichment of at least 1%.

17. A compound as recited in claim 1, having the structural formula:

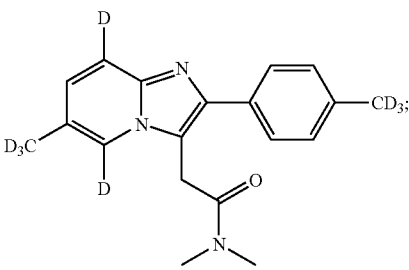

wherein each position designated as D has deuterium enrichment of at least 1%.

* * * * *